US012721912B2

(12) United States Patent
Jalomäki et al.

(10) Patent No.: US 12,721,912 B2
(45) Date of Patent: Sep. 1, 2026

(54) RADIOPHARMACEUTICAL COMPOSITIONS FOR ACTINIUM IN TARGETED RADIONUCLIDE THERAPY

(71) Applicant: Curium US LLC, St. Louis, MO (US)

(72) Inventors: Jarno Jalomäki, Helsinki (FI); Salla Seppänen, Helsinki (FI); Riku Parviainen, Helsinki (FI)

(73) Assignee: Curium US LLC, St. Louis, MO (US)

( * ) Notice: Subject to any disclaimer, the term of this patent is extended or adjusted under 35 U.S.C. 154(b) by 0 days.

(21) Appl. No.: 19/395,958

(22) Filed: Nov. 20, 2025

(65) Prior Publication Data

US 2026/0077075 A1 Mar. 19, 2026

Related U.S. Application Data

(62) Division of application No. 19/204,235, filed on May 9, 2025, now Pat. No. 12,502,441.

(60) Provisional application No. 63/753,208, filed on Feb. 3, 2025, provisional application No. 63/691,082, filed on Sep. 5, 2024, provisional application No. 63/645,572, filed on May 10, 2024, provisional application No. 63/644,943, filed on May 9, 2024.

(51) Int. Cl.

| | |
|---|---|
| ***A61K 51/08*** | (2006.01) |
| ***A61K 9/08*** | (2006.01) |
| ***A61K 47/02*** | (2006.01) |
| ***A61K 47/10*** | (2017.01) |
| ***A61K 47/22*** | (2006.01) |

(52) U.S. Cl.

CPC .............. *A61K 51/088* (2013.01); *A61K 9/08* (2013.01); *A61K 47/02* (2013.01); *A61K 47/10* (2013.01); *A61K 47/22* (2013.01)

(58) Field of Classification Search

CPC ........ A61K 51/088; A61K 9/08; A61K 47/02; A61K 47/10; A61K 47/22; A61K 9/0019; A61K 47/12; A61K 51/0402; A61K 51/121

See application file for complete search history.

(56) References Cited

U.S. PATENT DOCUMENTS

| | | | |
|---|---|---|---|
| 10,398,791 | B2 | 9/2019 | Eder et al. |
| 10,471,160 | B2 | 11/2019 | Eder et al. |
| 10,980,901 | B2 | 4/2021 | Morgenstern et al. |
| 2023/0302163 | A1 | 9/2023 | McCann |

FOREIGN PATENT DOCUMENTS

| | | | |
|---|---|---|---|
| WO | 2018108287 | A1 | 6/2018 |
| WO | 2023015212 | A1 | 2/2023 |
| WO | 2025129334 | A1 | 6/2025 |

OTHER PUBLICATIONS

Hooijman, et al., "Development of [225 Ac] Ac-PSMA-I&T for Targeted Alpha Therapy According to GMP Guidelines for Treatment of mCRPC," Pharmaceutics, 2021, vol. 13, No. 715, 15 pages.

International Search Report and Written Opinion for PCT Application No. PCT/US2025/028745, dated Sep. 10, 2025, 13 pages.

Ling, et al., "Evaluation of the tolerability and safety of [225Ac]Ac-PSMA-I&T in patients with metastatic prostate cancer: a phase I dose escalation study," BCM Cancer, Jan. 29, 2024, vol. 24, No. 146, 8 pages.

Notice of Allowance for U.S. Appl. No. 19/204,235, dated Aug. 20, 2025, 8 pages.

Banerjee S., et al., "Lutetium-177 Therapeutic Radiopharmaceuticals: Linking Chemistry, Radiochemistry, and Practical Applications," Chemical Reviews, Apr. 13, 2015, vol. 115, pp. 2934-2974.

Bjurlin M.A. "Imaging and Evaluation of Patients with High-risk Prostate Cancer," Nature Reviews, Urology, 2015, pp. 1-12.

Chatalic K., et al., "213Bi-labeled PSMA-Targeting Agents for Alpha Radionuclide Therapy of Prostate Cancer," Journal of Nuclear Medicine, May 1, 2016, vol. 57, No. 2, pp. 1-4.

Cheryl D., et al., "Anthropometric Reference Data for Children and Adults: United States, 2015-2018," National Center for Health Statistics, 2015-2018, vol. 3, No. 46, 44 pages.

De Kruijff R.M., et al., "A Critical Review of Alpha Radionuclide Therapy How to Deal with Recoiling Daughters?" Pharmaceuticals, Jun. 10, 2015, vol. 8, pp. 321-336.

Demirci E., et al., "$^{68}$Ga-PSMA PET/CT Imaging of Metastatic Clear Cell Renal Cell Carcinoma," European Journal of Nuclear Medicine and Molecular Imaging, 2014, 2 pages.

Foss C.A., et al., "Radiolabeled Small-molecule Ligands for Prostate-specific Membrane Antigen: in Vivo Imaging in Experimental Models of Prostate Cancer," Clinical Cancer Research, Jun. 1, 2005, vol. 11, No. 11, pp. 4022-4028.

Ghosh A., et al., "Tumor Target Prostate Specific Membrane Antigen (PSMA) and Its Regulation in Prostate Cancer," Journal of Cellular Biochemistry, 2004, vol. 91, pp. 528-539.

Hillier S., et al., "[13II]MIP-135, A Small Molecule Prostate-specific Membrane Antigen (PSMA) Inhibitor for Targeted Therapy of Prostate Cancer (PCa)," Journal of Nuclear Medicine, May 2011, vol. 52, No. 361, 2 pages.

Hillier S., et al., "[13II]MIP-1466, A Small Molecule Prostate-specific Membrane Antigen (PSMA) Inhibitor for Targeted Radiotherapy of Prostate Cancer (PCa)," Journal of Nuclear Medicine, May 2012, vol. 53, No. 170, 2 pages.

Hubenak J.R., et al., "Mechanisms of Injury to Normal Tissue After Radiotherapy: a Review," Plastic and Reconstructive Surgery, Jan. 2014, vol. 133, No. 1, pp. 49e-56e.

(Continued)

*Primary Examiner* — Robert S Cabral

(74) *Attorney, Agent, or Firm* — Polsinelli PC

(57) ABSTRACT

The present disclosure provides a high-energy, low toxicity radiopharmaceutical composition comprising actinium that performs as an anti-tumor agent for targeted radionuclide therapy and has improved shelf-life stability. Specifically, the radiopharmaceutical composition may include $^{225}$Ac-PSMA I&T, sodium ascorbate, and optionally hydrochloric acid. The radiopharmaceutical composition may be suitable for administration to a patient in need thereof, such as for the purpose of treating prostate cancer.

24 Claims, 25 Drawing Sheets
(2 of 25 Drawing Sheet(s) Filed in Color)

(56) References Cited

OTHER PUBLICATIONS

Jurcic J.G., et al., "Phase I Trial of Targeted Alpha-particle Therapy with Actinium-225 (225-Ac)-Lintuzumab and Low-dose Cytarabine (LDAC) in Patients Age 60 or Older with Untreated Acute Myeloid Leukemia (AML)," Blood, Dec. 2, 2016, vol. 128, No. 2, 3 pages.

Kairemo K., et al., "Design of 225Ac-PSMA for Targeted Alpha Therapy in Prostate Cancer," Annals of Translational Medicine, 2024, pp. 1-13, doi: 10.21037/atm-23-1842.

Knight R.D., "Physics for Scientists and Engineers," A Strategic Approach, vol. 5, pp. 1352-1381.

Kratochwil C., et al., "Ac-225-DOTATOC—an Empiric Dose Finding for Alpha Particle Emitter Based Radionuclide Therapy of Neuroendocrine Tumors," Journal of Nuclear Medicine, May 2015, vol. 56, No. 3, 4 pages.

Llhan H., et al., "Response to (225) Ac-PSMA-I&T after failure of long-term (177) Lu-PSMA RLT in mCRPC," European Journal of Nuclear Medicine and Molecular Imaging, Imaging, 2021, vol. 48, 1262-1263.

Mandel S.J., et al., "Superiority of Iodine-123 Compared with Iodine-131 Scanning for Thyroid Remnants in Patients with Differentiated Thyroid Cancer," Clinical Nuclear Medicine, Jan. 2001, vol. 26, No. 1, pp. 6-9.

McDevitt M.R., et al., "Design and Synthesis of $^{225}$AC Radioimmunopharmaceuticals," Applied Radiation and Isotopes, 2002, vol. 57, pp. 841-847.

Miederer M., et al., "Preclinical Evaluation of the alpha-Particle Generator Nuclide 225AC for Somatostatin Receptor Radiotherapy of Neuroendocrine Tumors," Cancer Therapy: Preclinical, Jun. 1, 2008, vol. 14, No. 11, pp. 3555-3561.

Milenic D.E., et al., "Targeting of Radio-isotopes for Cancer Therapy," Cancer Biology & Therapy, Apr. 2004, vol. 3, No. 4, pp. 361-370.

Nomura N., et al., "Prostate Specific Membrane Antigen (PSMA) Expression in Primary Gliomas and Breast Cancer Brain Metastases," Cancer Cell International, 2014, vol. 14, No. 26, pp. 1-8.

Petitioner, *Fusion Pharmaceuticals, Inc*., v. Patent Owner, *Universitat Heidelberg and the European Atomic Energy Community* (*EURATOM*), Represented by the European Commission, Case No. IPR2023-00551, U.S. Pat. No. 10,980,901 B2, Dated, Nov. 21, 2023, 95 pages.

Petitioner *Fusion Pharmaceuticals, Inc*. v. Patent Owner *Universitat Heidelberg*, Case No. IPR2023-00551, U.S. Pat. No. 10,980,901, Dated, Apr. 20, 2021, 55 pages.

Pomper M.G., et al., "$^{11}$C-MCG: Synthesis, Uptake Selectivity, and Primate PET of a Probe for Glutamate Carboxypeptidase II (NAALADase)," Molecular Imaging, Apr. 2002, vol. 1, No. 2, pp. 96-101.

Price E.W., et al., "Matching Chelators to Radiometals for Radiopharmaceuticals," Chemical Society Reviews, Oct. 30, 2013, 31 pages.

Prostate Cancer., "Surveillance, Epidemiology, and End Results Program," National Cancer Institute, 15 pages.

Ross J.S., et al., "Correlation of Primary Tumor Prostate-specific Membrane Antigen Expression with Disease Recurrence in Prostate Cancer," Clinical Cancer Research, Dec. 15, 2003, vol. 9, pp. 6357-6362.

Scheinberg D.A., et al., "Actinium-225 in Targeted Alpha-particle Therapeutic Applications," Current Radiopharmaceuticals, Oct. 2011, vol. 4, No. 4, pp. 306-320.

Sgouros G., et al., "MIRD Pamphlet No. 22 (Abridged): Radiobiology and Dosimetry of alpha-Particle Emitters for Targeted Radionuclide Therapy," Journal of Nuclear Medicine, Feb. 2010, vol. 51, pp. 311-328.

Sharifi N., et al., "Androgen Deprivation Therapy for Prostate Cancer," JAMA, Jul. 13, 2005, vol. 294, No. 2, pp. 238-244.

Silver D.A., et al., "Prostate-specific Membrane Antigen Expression in Normal and Malignant Human Tissues," Clinical Cancer Research, Jan. 1997, vol. 3, pp. 81-85.

Turkbey B., et al., "Multiparametric Prostate Magnetic Resonance Imaging in the Evaluation of Prostate Cancer," Cancer Journal for Clinicians, 2016, vol. 66, pp. 326-336.

Viola-Villegas N., et al., "The Coordination Chemistry of 1,4,7, 10-tetraazacyclododecane-N,N', N", N"m-Tetraacetic Acid (H4DOTA): Structural Overview and Analyses on Structure-stability Relationships," Coordination Chemistry Reviews, 2009, vol. 253, pp. 1906-1925.

Weineisen M., et al., "Synthesis and Preclinical Evaluation of DOTAGA-conjugated PSMA Ligands for Functional Imaging and Endoradiotherapy of Prostate Cancer," European Journal of Nuclear Medicine and Molecular Imaging, 2014, vol. 4, No. 63, pp. 1-15.

Wernicke A.G., et al., "Prostate-specific Membrane Antigen Expression in Tumor-associated Vasculature of Breast Cancers," Acta Pathologica, Microbiologica et Immunologica Scandinavica, 2014, vol. 122, pp. 482-489.

Zhao L., et al., "Clinical Pharmacology Considerations in Biologics Development," Acta Pharmacologica Sinica, 2012, vol. 33, pp. 1339-1347.

Baum, R.P.; Langbein, T.; Singh, A.; Shahinfar, M.; Schuchardt, C.; Volk, G.F.; Kulkarni, H. "Injection of Botulinum Toxin for Preventing Salivary Gland Toxicity after PSMA Radioligand Therapy: An Empirical Proof of a Promising Concept." Nucl. Med. Mol. Imaging 2018, 52, 80-81.

Chatalic, K.L.; Heskamp, S.; Konijnenberg, M.; Molkenboer-Kuenen, J.D.; Franssen, G.M.; Clahsen-van Groningen, M.C.; et al. "Towards Personalized Treatment of Prostate Cancer:PSMA I&T, a Promising Prostate-Specific Membrane Antigen-Targeted Theranostic Agent." Theranostics 2016, 6, 849-861.

Cornford, P.; Bellmunt, J.; Bolla, M.; Briers, E.; De Santis M,.; Gross, T.; et al. "EAU-ESTRO-SIOG Guidelines on Prostate Cancer. Part II: Treatment of Relapsing, Metastatic, and Castration-Resistant Prostate Cancer." Eur Urol. 2017, 71(4), 630-642.

De Medeiros, R.B.; Grigolon, M.V.; Araújo, T.P.; Srougi, M. "Metastatic castration-resistant prostate cancer (mCRPC) treated with 225Ac-PSMA-617. Case report." Braz. J. Oncol. 2019, 15, 1-9.

Delpassand, E.S.; Hashmi, M.J.; Kazakin, J.; Nawaz, O., Garufi G.; Schindler, J.; Nordquist, L. "Preliminary efficacy and safety results from the TATCIST trial: A PSMA-directed targeted alpha therapy with FPI-2265 (225Ac-PSMA-I&T) for the treatment of metastatic castration-resistant prostate cancer." Abstracts the American Association for Cancer Research (AACR) Annual Meeting; Apr. 5-10, 2024; San Diego, CA.

Fendler, W.P.; Rahbar, K.; Herrmann, K.; Kratochwil, C.; Eiber, M. "177Lu-PSMA Radioligand Therapy for Prostate Cancer." J Nucl Med. 2017, 58(8), 1196-1200.

Feuerecker, B.; Tauber, R.; Knorr, K.; Heck, M.; Beheshti, A.; Seidl, C.; et al. "Activity and Adverse Events of Actinium-225-PSMA-617 in Advanced Metastatic Castration-resistant Prostate Cancer After Failure of Lutetium-177-PSMA." Eur. Urol. 2021, 79(3), 343-350.

Gallyamov, M.; Meyrick, D.; Barley, J.; Lenzo, N. "Renal outcomes of radioligand therapy: Experience of 177lutetium—prostate specific membrane antigen ligand therapy in metastatic castrate-resistant prostate cancer." Clin. Kidney J. 2019, 13, 1049-1055.

Gosewisch, A.; Schleske, M.; Gildehaus, F. J.; Berg, I.; Kaiser, L.; Brosch, J.; et al. "Image-based dosimetry for 225Ac-PSMA-I&T therapy using quantitative SPECT." Eur. J. Nucl. Med. Mol. Imaging 2021, 48, 1260-1261.

Graf, F.; Fahrer, J.; Maus, S.; Morgenstern, A.; Bruchertseifer, F.; Venkatachalam, S.; et al. "DNA Double Strand Breaks as Predictor of Efficacy of the Alpha-Particle Emitter Ac-225 and the Electron Emitter Lu-177 for Somatostatin Receptor Targeted Radiotherapy." PLoS One 2014, 9(2), e88239. doi: 10.1371/ journal.pone.008823.

Haberkorn, U.; Eder, M.; Kopka, K.; Babich, J.W.; Eisenhut M. "New Strategies in Prostate Cancer: Prostate-Specific Membrane Antigen (PSMA) Ligands for Diagnosis and Therapy." Clin Cancer Res. 2016, 22(1), 9-15.

Ilhan, H.; Gosewisch, A.; Böning, G.; Völter, F.; Zacherl, M.; Unterrainer, M.; et al. "Response to (225) Ac-PSMA-I&T after failure of long-term (177) Lu-PSMA RLT in mCRPC." Eur. J. Nucl. Med. Mol. Imaging 2021, 48, 1262-1263.

Kairemo, K. "Targeted alpha therapy: a new tool for advanced prostate cancer." thelancet.com/oncology, Feb. 2024, 25(2):148-149.

(56) References Cited

OTHER PUBLICATIONS

Kairemo, K.; Kgatle, M.; Bruchertseifer, F.; Morgenstern, A.; Sathekge, M.M. "Design of 225Ac-PSMA for targeted alpha therapy in prostate cancer." Ann Transl Med 2024. doi: 10.21037/atm-23-1842.
Khreish, F.; Eber,t N.; Ries, M.; Maus, S.; Rosar , F.; Bohnenberge,r H.; et al. "(225) Ac-PSMA-617/ (177) Lu-PSMA-617 tandem therapy of metastatic castration-resistant prostate cancer: Pilot experience." Eur. J. Nucl. Med. Mol. Imaging 2020, 47, 721-728.
Kinoshita, Y.; Kuratsukuri, K.; Landas, S.; Imaida K.; Rovito, P.M.; Wang, C.Y.; Haas G.P. "Expression of prostate-specific membrane antigen in normal and malignant human tissues." World J Surg. 2006, 30(4), 628-636.
Kratochwil, C.; Bruchertseifer, F.; Giesel, F.L.; Weis, M.; Verburg, F.A.; Mottaghy, F.; et al. "225Ac-PSMA-617 for PSMA-Targeted alpha-Radiation Therapy of Metastatic Castration-Resistant Prostate Cancer." J. Nucl. Med. 2016, 57, 1941-1944.
Kratochwil, C.; Bruchertseifer, F.; Rathke, H.; Bronzel, M.; Apostolidis, C.; Weichert, W.; et al. "Targeted alpha-Therapy of Metastatic Castration-Resistant Prostate Cancer with (225) Ac-PSMA-617: Dosimetry Estimate and Empiric Dose Finding." J. Nucl. Med. 2017, 58, 1624-1631.
Kratochwil, C.; Bruchertseifer, F.; Rathke, H.; Hohenfellner, M.; Giesel, F.L.; Haberkorn, U.; Morgenstern, A. "Targeted alpha-Therapy of Metastatic Castration-Resistant Prostate Cancer with (225) Ac-PSMA-617: Swimmer-Plot Analysis Suggests Efficacy Regarding Duration of Tumor Control." J. Nucl. Med. 2018, 59, 795-802.
Kratochwil, C.; Giesel, F.L.; Heussel, C.-P.; Kazdal D.; Endris, E.; Nientiedt, C.; et al. "Patients Resistant Against PSMA-Targeting a-Radiation Therapy Often Harbor Mutations in DNA Damage-Repair-Associated Genes." J Nucl Med 2020, 61, 683-688.
Kratochwil, C.; Giesel, FL.; Eder, M.; Afshar-Oromieh, A.; Benešová, M.; Mier, W.; et al. "[$^{177}$Lu] Lutetium-labelled PSMA ligand-induced remission in a patient with metastatic prostate cancer." Eur J Nucl Med Mol Imaging. 2015, 42 (6), 987-988.
Kratochwil, C.; Schmidt, K.; Afshar-Oromieh, A.; Bruchertseifer, F.; Rathke, H.; Morgenstern, A.; et al. "Targeted alpha therapy of mCRPC: Dosimetry estimate of (213) Bismuth-PSMA-617." Eur. J. Nucl. Med. Mol. Imaging 2018, 45, 31-37.
Langbein, T.; Chausse, G.; Baum, R.P. "Salivary Gland Toxicity of PSMA Radioligand Therapy: Relevance and Preventive Strategies." J. Nucl. Med. 2018, 59, 1172-1173.
Lawal, I.O.; Morgenstern, A.; Vorster, M.; Knoesen, O.; Mahapane, J.; Hlongwa, K.N.; et al. "Hematologic toxicity profile and efficacy of [225Ac]Ac-PSMA-617 $\alpha$-radioligand therapy of patients with extensive skeletal metastases of castration-resistant prostate cancer." Eur J Nucl Med Mol Imaging. 2022, 49(10), 3581-3592. doi: 10.1007/s00259-022-05778-w2022.
Lee, D.Y.; Kim, Y.I. "Effects of 225Ac-Labeled Prostate-Specific Membrane Antigen Radioligand Therapy in Metastatic Castration-Resistant Prostate Cancer: A Meta-Analysis." J Nucl Med. 2022, 63(6), 840-846.
Ma, J.; Li, L.; Liao, T.; Gong, W.; Zhang, C. "Efficacy and Safety of 225Ac-PSMA-617-Targeted Alpha Therapy in Metastatic Castration-Resistant Prostate Cancer: A Systematic Review and Meta-Analysis." Front Oncol. 2022, 3, 12:796657. doi: 10.3389/fonc.2022.796657.
Morgenstern, A.; Apostolidis, C.; Kratochwil, C.; Sathekge, M.; Krolicki, L.; Bruchertseifer, F. "An Overview of Targeted Alpha Therapy with (225)Actinium and (213)Bismuth." Curr Radiopharm. 2018, 11(3), 200-208.
Nonnekens, J.; Chatalic, K.L.; Molkenboer-Kuenen, J.D.; Beerens, C.E.; Bruchertseifer, F.; Morgenstern, A.; et al. "(213) Bi-Labeled Prostate-Specific Membrane Antigen-Targeting Agents Induce DNA Double-Strand Breaks in Prostate Cancer Xenografts." Cancer Biother. Radiopharm. 2017, 32, 67-73.
Parida, G.K.; Panda, R.A.; Bishnoi, K.; Agrawal, K. "Efficacy and Safety of Actinium-225 Prostate-Specific Membrane Antigen Radioligand Therapy in Metastatic Prostate Cancer: A Systematic Review and Metanalysis." Med Princ Pract. 2023, 32(3), 178-191.
Pelletier, K.; Côté, G.; Fallah-Rad, N.; John, R.; Kitchlu, A. "Chronic kidney disease after 225Ac-PSMA617 therapy in patients with metastatic prostate cancer." Kidney Int. Rep. 2021, 6, 853-856.
Puttemans, J.; Lahoutte, T.; D'Huyvetter, M.; Devoogdt, N. "Beyond the Barrier: Targeted Radionuclide Therapy in Brain Tumors and Metastases." Pharmaceutics 2019, 11, 376.
Rathke, H.; Bruchertseifer, F.; Kratochwil, C.; Keller, H.; Giesel, F.L.; Apostolidis, C.; et al. "First patient exceeding 5-year complete remission after 225Ac-PSMA-TAT." European Journal of Nuclear Medicine and Molecular Imaging 2021, 48, 311-312.
Rathke, H.; Kratochwil, C.; Hohenberger, R.; Giesel, F.L.; Bruchertseifer, F.; Flechsig, P.; et al. "Initial clinical experience performing sialendoscopy for salivary gland protection in patients undergoing (225) Ac-PSMA-617 RLT." Eur. J. Nucl. Med. Mol. Imaging 2019, 46, 139-147.
Rosar, F.; Krause, J.; Bartholomä, M.; Maus, S.; Stemler T.; Hierlmeier, I.; et al. "Efficacy and Safety of [225Ac]Ac-PSMA-617 Augmented [177Lu]Lu-PSMA-617 Radioligand Therapy in Patients with Highly Advanced mCRPC with Poor Prognosis." Pharmaceutics. 2021, 13, 722. doi: 10.3390/pharmaceutics13050722.
Ruigrok, E.A.M, Tamborino, G.; de Blois E.; Roobol, S.J.; Verkaik, N.; De Saint-Hubert, M.; et al. "In vitro dose effect relationships of actinium-225- and lutetium-177-labeled PSMA-I&T." Eur J Nucl Med Mol Imaging. 2022, 49, 3627-3638.
Rosar, F.; Krause, J.; Bartholomä, M.; Maus,, S.; Stemler T.; Hierlmeier I.; et al. "Efficacy and Safety of [225Ac]Ac-PSMA-617 Augmented [177Lu]Lu-PSMA-617 Radioligand Therapy in Patients with Highly Advanced mCRPC with Poor Prognosis." Pharmaceutics. 2021, 13, 722, 943-951.
Satapathy, S.; Mittal, B.R.; Sood, A.; Das, C.K.; Singh, S.K.; Mavuduru, R.S.; Bora, G.S. "Health-Related Quality-of-Life Outcomes with Actinium-225-Prostate-Specific Membrane Antigen-617 Therapy in Patients with Heavily Pretreated Metastatic Castration-Resistant Prostate Cancer." Indian J Nucl Med. 2020, 35, 299-304.
Satapathy, S.; Sood, A.; Das, C.K.; Mittal, B.R. "Evolving role of 225Ac-PSMA radioligand therapy in metastatic castration-resistant prostate cancer-a systematic review and meta-analysis." Prostate Cancer Prostatic Dis. 2021, 24 (3), 880-890.
Sathekge, M.; Bruchertseifer, F.; Knoesen, O.; Reyneke, F.; Lawal, I.; Lengana, T.; et al. "(225) Ac-PSMA-617 in chemotherapy-naive patients with advanced prostate cancer: A pilot study." Eur. J. Nucl. Med. Mol. Imaging, 2019, 46, 129-138.
Sathekge, M.; Bruchertseifer, F.; Vorster, M.; Lawal, I.O.; Knoesen, O.; Mahapane, J.; et al. "Predictors of Overall and Disease-Free Survival in Metastatic Castration-Resistant Prostate Cancer Patients Receiving (225) Ac-PSMA-617 Radioligand Therapy." J. Nucl. Med. 2020, 61, 62-69.
Sathekge, M.; Bruchertseifer, F.; Vorster, M.; Lawal, I.O.; Mokoala, K.; Reed, J.; et al. "225Ac-PSMA-617 radioligand therapy of de novo metastatic hormone-sensitive prostate carcinoma (mHSPC): preliminary clinical findings." Eur J Nucl Med Mol Imaging. 2023, 50(7), 2210-2218. doi: 10.1007/s00259-023-06165-9. Epub ahead of print. PMID: 36864360.
Sathekge, M.; Knoesen, O.; Meckel, M.; Modiselle, M.; Vorster, M.; Marx, S. "(213) Bi-PSMA-617 targeted alpha-radionuclide therapy in metastatic castration-resistant prostate cancer." Eur. J. Nucl. Med. Mol. Imaging 2017, 44, 1099-1100.
Sathekge, M.M.; Bruchertseifer, F.; Lawal, I.O.; Vorster, M.; Knoesen, O.; Lengana, T.; et al. "Treatment of brain metastases of castration-resistant prostate cancer with (225)Ac-PSMA-617." Eur. J. Nucl. Med. Mol. Imaging, 2019, 46, 1756-1757.
Sen, I.; Thakral, P.; Tiwari, P.; Pant, V.; Das, S.S.; Manda, D.; Raina, V. "Therapeutic efficacy of 225Ac-PSMA-617 targeted alpha therapy in patients of metastatic castrate resistant prostate cancer after taxane-based chemotherapy." Ann Nucl Med, 2021, 35, 794-810.
Sgouros ,G. "Dosimetry, Radiobiology and Synthetic Lethality: Radiopharmaceutical Therapy (RPT) With Alpha-Particle-Emitters." Semin Nucl Med. 2020, 50(2), 124-132.
Van der Doelen, M.J.; Mehra, N.; van Oort, I.M.; Looijen-Salamon, M.G.; Janssen, M.J.R.; Custers, J.A.; et al. "Clinical outcomes and molecular profiling of advanced metastatic castration-resistant pros-

(56) References Cited

OTHER PUBLICATIONS tate cancer patients treated with 225Ac-PSMA-617 targeted alpha-radiation therapy." Urologic Oncology: Seminars and Original Investigations 2020, 1-10, https://doi.org/10.1016/j.urolonc.2020.12.002.

Vorster, M.; Sathekge, M. "Advances in PSMA Alpha Theragnostics." Semin Nucl Med. 2024, S0001-2998(24), 00029-1. doi: 10.1053/j.semnuclmed.2024.03.004.

Weineisen, M.; Schottelius, M.; Simeček, J.; Baum, R.P.; Yildiz, A.; Beykan, S.; et al. "68Ga- and 177Lu-Labeled PSMA I&T: Optimization of a PSMA-Targeted Theranostic Concept and First Proof-of-Concept Human Studies." J Nucl Med 2015, 56, 1169-1176.

Yadav, M.P.; Ballal, S.; Sahoo, R.K.; Tripathi, M.; Seth, A.; Bal, C. "Efficacy and safety of (225) Ac-PSMA-617 targeted alpha therapy in metastatic castration-resistant Prostate Cancer patients." Theranostics, 2020, 10, 9364-9377.

Zacherl, M.J.; Gildehaus, F.J.; Mittlmeier, L.; Boening, G.; Gosewisch, A.; Wenter, V.; et al. "First clinical results for PSMA targeted alpha therapy using (225) Ac-PSMA-I&T in advanced mCRPC patients." J. Nucl. Med. 2021, 62, 669- 674.

Notice of Allowance for U.S. Appl. No. 19/395,907, dated Apr. 14, 2026, 7 pages.

Swimmer plot showing duration of tumor control in months.

Swimmer plot showing duration of tumor control relative to duration of previous treatment lines.

Waterfall graphs of PSA response. Patients who died before week 8 (red) or discontinued because of xerostomia (yellow) are classified as progression.

Waterfall plot demonstrating percentage change in PSA levels after treatment with 225Ac-PSMA-617 in studied patients (x-axis = number of patients; y-axis = percentage change).

Waterfall plots of PSA, lactate dehydrogenase (LDH), and ALP response after TAT using $^{225}$Ac-PSMA I&T. A and B describe PSA changes after 8 wk and best PSA response after first TAT cycle. C and D describe best LDH and ALP response after median of 2 TAT cycles.

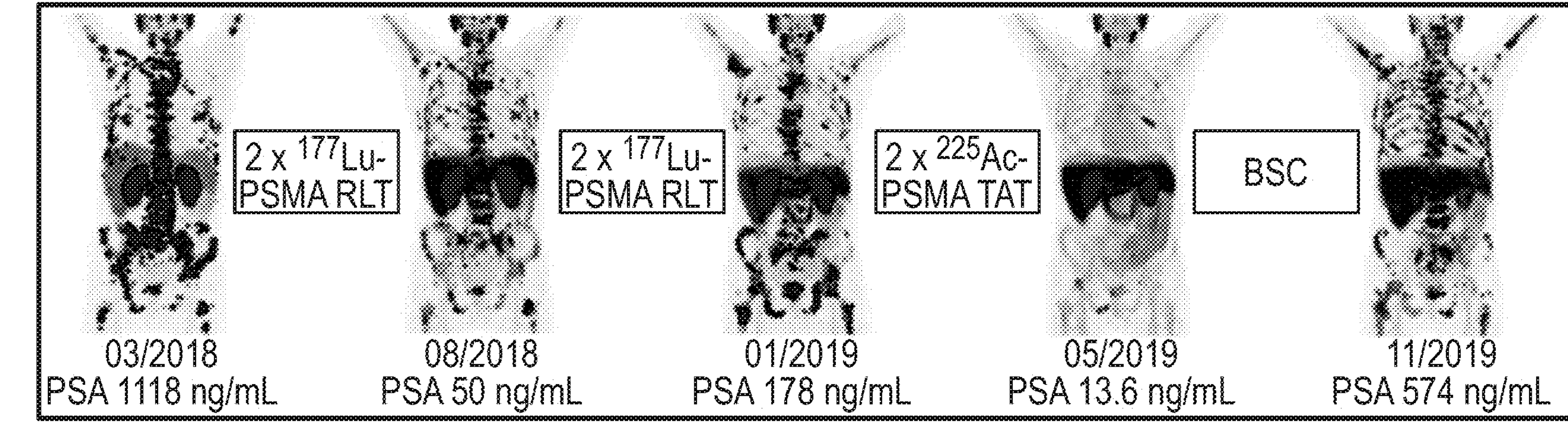

A 79-y-old mCRPC patient (patient 11) with lymphatic and bone metastases. Patient received 2 cycles of $^{177}$Lu-PSMA RLT (cumulative activity, 10.5 GBq) after failure of docetaxel and showed initial response. However, disease progression was observed in January 2019 after 2 additional $^{177}$Lu-PSMA RLT cycles (cumulative activity, 12 Gbq), and patient was admitted for 225Ac-PSMA I&T TAT. PSA follow-up and PSMA PET showed impressive response after 2 cycles (cumulative activity, 13.4 MBq). Unfortunately, patient developed grade 3 leukocytopenia, and TAT could not be continued. Disease progression was observed in November 2019 after best supportive care (SC).

FIG. 9

Patient Characteristics

| Patient no. | PSA (ng/mL) | Location of metastases | Previous pharmacotherapy | Previous radiotherapy | Previous radioactive drugs |
|---|---|---|---|---|---|
| 1 | 227 | LN, bone, liver, adrenal | Abi, Doce, Enza | RTx, bone | $^{177}Lu$ (27.9 GBq) |
| 2 | 239 | Bone, LN, lung, skin | Keto, Estra, Doce, Abi, Trial, Enza | RTx, local and bone | $^{90}Y$ (7.4 GBq) |
| 3 | 697 | LN, bone, adrenal | Abi, Doce, Trial, Cabazi | RTx, pelvic and bone | None |
| 4 | 111 | LN, bone | Abi, Enza, Doce | RTx, pelvic and bone | $^{177}Lu$ (16 GBq) |
| 5 | 481 | Liver | Abi, Enza, Doce, Cabazi | RTx, local and pelvic | None |
| 6 | 759 | LN, bone | Abi, Enza, Doce, Cabazi | RTx, local, pelvic, and bone | $^{177}Lu$ (44.4 GBq) |
| 7 | 1,658 | LN, bone | Abi, Doce, Cabazi, Estra, Enza | RTx, local and pelvic | None |

PSA = prostate-specific antigene; LN = lymph node; Abi = abiraterone; Doce = docetaxel; Enza = enzalutamide; RTx = radiotherapy; Keto = ketoconazole; Estra = estramustine; Trial = Phase-1 trial of BAY2010112 (NCT01723475); Cabazi = cabazitaxel.

FIG. 10

Summary of Observed Gene Defects and Previous Exposure to $^{225}$Ac-PSMA617

| Patient no. | $^{225}$Ac Dose (MBq), cumulative | Probable deleterious mutation | Whole-gene deletion | Low-level amplification | Variants of unknown significance |
|---|---|---|---|---|---|
| 1 | 12 (fractions, 6/6) | ATM | TP53 | — | FAM175A |
| 2 | 14 (fractions, 6/8) | BRCA1, PMS1, x2 TP53 | — | — | ATM, BARD1, 3xERCC2, ERCC4, FANCB, FANCG |
| 3 | 14 (fractions, 6/8) | CHEK2 | FANCB, NBN, ATM | ATR, BRIP1 SLX4 | FANCL, RECQL4 |
| 4 | 22 (fractions, 6/6/6/4) | — | — | — | MSH2 |
| 5 | 20 (fractions, 8/6/6) | PALB2 | — | — | SLX4 |
| 6 | 18 (fractions, 6/6/6) | TP53, CHEK2 | MSH2, MSH6 | — | BRCA1 |
| 7 | 18 (fractions, 8/6/4) | — | BRCA2 | — | ERCC2, SLX4, RAD50 |

FIG. 11

| Toxic effect | Grade I or II | Grade III | Grade IV |
|---|---|---|---|
| Dry mouth | 62 (85) | 0 | 0 |
| Dry eyes | 4 (5) | 0 | 0 |
| Anorexia | 23 (32) | 0 | 0 |
| Nausea | 15 (21) | 0 | 0 |
| Vomiting | 4 (5) | 0 | 0 |
| Constipation | 19 (26) | 0 | 0 |
| Fatigue | 37 (51) | 0 | 0 |
| Weight loss | 28 (38) | 0 | 0 |
| Dyspepsia | 3 (4) | 0 | 0 |
| Dysgeusia | 4 (5) | 0 | 0 |
| Anemia | 22 (30) | 5 (7) | 0 |
| Leukopenia | 7 (10) | 2 (3) | 0 |
| Thrombocytopenia | 6 (8) | 1 (1) | 0 |
| Hypoalbuminemia | 14 (19) | 0 | 0 |
| Renal failure | 18 (25) | 3 (4) | 2 (3) |
| Dysuria | 13 (18) | 0 | 0 |

Data are reported as numbers of patients, with percentages of patients in parentheses.

FIG. 12

Therapy-Related Hematologic and Renal Adverse Events After $^{225}$Ac-PSMA-I&T According to Common Terminology Criteria for Adverse Events, Version 5.0

| Event | Before TAT | | | | After TAT | | | |
|---|---|---|---|---|---|---|---|---|
| | Gr. 1 | Gr. 2 | Gr. 3 | Gr. 4 | Gr. 1 | Gr. 2 | Gr. 3 | Gr. 4 |
| Hematologic | | | | | | | | |
| Anemia | 8 (57%) | 4 (29%) | 2 (14%) | | 3 (21%) | 8 (57%) | 3 (21%) | — |
| Thrombopenia | 3 (21%) | 1 (7%) | — | — | 3 (21%) | 3 (21%) | — | — |
| Leukopenia | 2 (14%) | 1 (7%) | — | — | 4 (28%) | — | 1 (7%) | — |
| Renal | 1 (7%) | — | — | — | 1 (7%) | 1 (7%) | — | — |
| Gastrointestinal | | | | | | | | |
| Xerostomia | 6 (43%) | 2 (14%) | — | ND | 8 (57%) | 5 (36%) | — | ND |
| Dysgeusia | — | — | — | — | 5 (36%) | 1 (7%) | — | — |
| Anorexia | 9 (64%) | — | — | — | 7 (50%) | 2 (14%) | — | — |
| Nausea | — | — | — | — | 4 (29%) | 1 (7%) | — | — |
| General | | | | | | | | |
| Fatigue | 10 (71%) | 1 (7%) | — | — | 6 (43%) | 6 (43%) | — | — |
| Weight loss | NA | NA | NA | NA | 4 (29%) | — | — | — |

Gr. = Grade; ND = not defined; NA = not applicable.
Data are number and percentage.

FIG. 13

| Patient no. | Age (y) | Dose (kBq/kg) | Baseline PSA | Metastasis* | GnRH-A/A | Antiandrogen | Abiraterone | Enzalutamide | Docetaxel | Other systemic therapies |
|---|---|---|---|---|---|---|---|---|---|---|
| 1 | 73 | 50 | 224 | OSS, BRA | x | x | x | x | x | Ketokonazol, vinorelbine, β-PSMA ($^{131}I$) |
| 2 | 71 | 50 | 63 | LYM, OSS, HEP | x | x |  | x | x | Cabazitaxel, estramustine |
| 3 | 67 | 50 | <0.1 | OSS | x | x | x |  |  |  |
| 4 | 60 | 50 | 118 | LYM, OSS | x | x |  | x | x | Cabazitaxel, $^{223}Ra$ |
| 5 | 70 | 100 | 276 | LYM, OSS, PUL | x | x | x | x | x | Curevac, thalidomind, celecoxib, DOTATOC |
| 6 | 53 | 100 | 245 | LYM, OSS | x |  |  |  |  |  |
| 7 | 58 | 100 | 64.7 | LYM, OSS, PUL | x | x | x | x | x | β-PSMA ($^{131}I$) |
| 8 | 78 | 100 | 420 | LYM, OSS | x | x | x | x | x | Cabozantinib |
| 9 | 79 | 150 | 1,153 | LYM, OSS | x | x | x | x |  | Estramustine |
| 10 | 57 | 150 | 744 | OSS, HEP, BRA | x | x |  |  | x | $^{223}Ra$, β-PSMA ($^{177}Lu$) |
| 11 | 68 | 200 | <0.1 | LYM, OSS, PUL, HEP, BRA | x | x | x |  | x |  |
| 12 | 60 | 200 | 1,100 | LYM, OSS, HEP | x | x | x |  | x | Sorafenib, TACE (Irinotecan) |
| 13 | 78 | 200 | 2,841 | LYM, OSS, HEP | x | x | x | x | x | Tasquinimod |
| 14 | 63 | 200 | 2.8 | LYM, OSS, HEP | x | x | x | x |  |  |

*Site of disease according to TNM classification.

GnRH-A/A = previous treatment with gonadotropin-releasing hormone analogs or antagonists; OSS = Osseous; BRA = Brain; LYM = lymphatic; HEP = Hepatic; PUL = lung; TACE = transarterial chemoembolization.

FIG. 14

Dosimetry of Dose-Limiting Organs with Different PSMA Ligands

| Dose-limiting organ | This work | | Zechmann et al. (24) | | Kratochwil et al. (1) | |
|---|---|---|---|---|---|---|
| | $^{225}$Ac-PSMA-617 ($Sv_{RBE5}$/MBq) | $^{225}$Ac-PSMA-617 ($Sv_{RBE5}$/7.4 MBq) | $^{131}$I-MIP-1095 (Gy/GBq) | $^{131}$I-MIP-1095 (Gy/3.7 GBq) | $^{177}$Lu-PSMA-617 (Gy/GBq) | $^{177}$Lu-PSMA-617 (Gy/7.4 GBq) |
| Salivary glands | 2.33 | 17.24 | 4.62 | 17.09 | 1.38 | 10.21 |
| Kidneys | 0.74 | 5.48 | 1.45 | 5.37 | 0.75 | 5.55 |
| Red Marrow | 0.05 | 0.37 | 0.31 | 1.15 | 0.03 | 0.22 |

FIG. 15

| | Dose escalation scheme | PSA response 8 Wk | Toxicity (xerostomia) |
|---|---|---|---|
| 200 GBq'kg BW | | | |
| 150 GBq'kg BW | | | |
| 100 GBq'kg BW | | | |
| 50 GBq'kg BW | | | |

2-mo interval 4-mo interval

Reasonable treatment corridor between insufficient treatment response (red: patient died before reevaluation; orange: PSA progression; green: imaging or PSA response) and in-tolerable toxicity (red: xerophthalmia; orange: xerostomia g2; green: no or only G1 xerostomia). During repeated therapies, insufficient PSA response was observed at 4-mo interval.

FIG. 16

Radiolabeling kinetics of $^{225}$Ac- PSMA I&T in reaction mixtures containing different molar ratios of hydrochloric acid and sodium ascorbate using radio-TLC method.

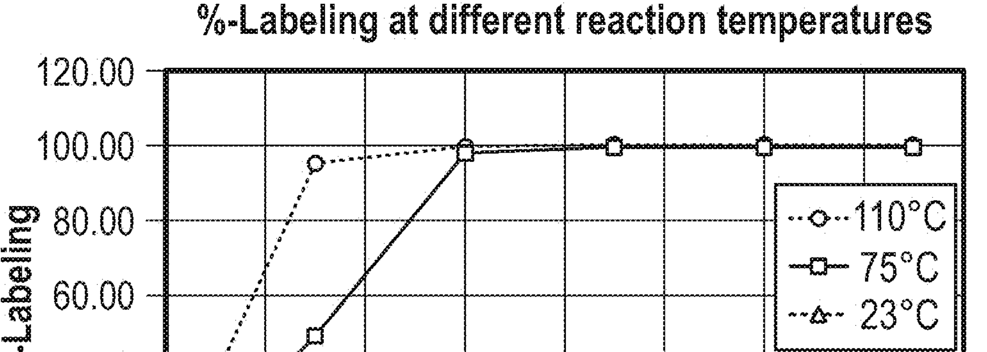
Radiolabeling kinetics of $^{225}$Ac- PSMA I&T at different temperature set points using radio-TLC method.
FIG. 19
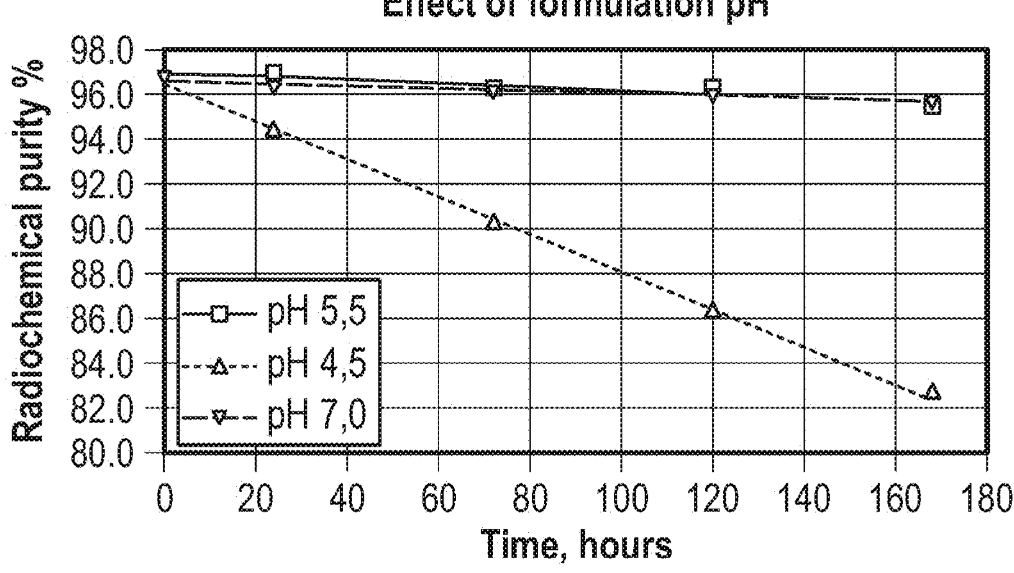
Radiochemical stability of $^{225}$Ac- PSMA I&T at different pH formulations using radio-TLC method.
FIG. 20

Effect of ascorbic acid concentration on radiochemical stability of $^{225}$Ac-PSMA I&T using radio-TLC method.

Stability screening of different formulation compositions at 40°C using radio-TLC method.

More detailed formulation screening of the effect of excipients at 40°C using radio-TLC method.

Radiochemical stability of $^{225}$Ac- PSMA I&T by the radio-TLC method in different DTPA formulations using radio-TLC method.

Radiochemical stability of $^{225}$Ac-PSMA I&T by the radio-TLC method in formulations containing different concentrations of sodium ascorbate.

Effect of sodium ascorbate concentration on the radiochemical purity of $^{225}$Ac-PSMA I&T determined by HPLC fraction collection method.

FIG. 27

Radiochemical purity $^{225}$Ac-PSMA I&T prepared using process A.

Radiochemical purity $^{225}$Ac-PSMA I&T prepared using process B.

Radioactivity of HPLC fractions in process A formulation. Fractions were collected in 1 min intervals and time in x-axis represents the vial number of the HPLC fraction.

Radioactivity of HPLC fractions in process B formulation. Fractions were collected in 1 min intervals and time in x-axis represents the vial number of the HPLC fraction.

RADIOPHARMACEUTICAL COMPOSITIONS FOR ACTINIUM IN TARGETED RADIONUCLIDE THERAPY

CROSS-REFERENCE TO RELATED APPLICATIONS

This application is a divisional of U.S. application Ser. No. 19/204,235 filed May 9, 2025, entitled "RADIOPHARMACEUTICAL COMPOSITIONS FOR LOW TOXICITY ACTINIUM IN TARGETED RADIONUCLIDE THERAPY", which claims priority to U.S. Provisional Application No. 63/644,943 entitled "RADIOPHARMACEUTICAL COMPOSITIONS FOR LOW TOXICITY ACTINIUM IN TARGETED RADIONUCLIDE THERAPY", filed May 9, 2024, U.S. Provisional Application No. 63/645,572 entitled "RADIOPHARMACEUTICAL COMPOSITIONS FOR ACTINIUM IN TARGETED RADIONUCLIDE THERAPY", filed May 10, 2024, U.S. Provisional Application No. 63/691,082 entitled "225Ac-PSMA I&T INJECTION PROCESS AND FORMULATION", filed Sep. 5, 2024, and U.S. Provisional Application No. 63/753,208 entitled "RADIOPHARMACEUTICAL COMPOSITIONS FOR ACTINIUM IN TARGETED RADIONUCLIDE THERAPY", filed Feb. 3, 2025 the entire contents of which are incorporated by reference herein.

FIELD OF THE INVENTION

The present disclosure relates to a high-energy, low toxicity radiopharmaceutical composition comprising actinium that performs as an anti-tumor agent for targeted radionuclide therapy.

BACKGROUND OF THE INVENTION

Prostate cancer (PC) is the most frequent non-cutaneous cancer and the second most frequent cause of cancer deaths for adult men. A worldwide estimate of PC in 2008 implied 899,000 new cases and 258,000 PC deaths. Most deaths related to prostate cancer are due to advanced disease, which results from any combination of lymphatic, blood, or contiguous local spread. Most patients with PC who die, die of metastatic PC.

Targeted radionuclide therapy has become an attractive and quickly developing therapy option for many different cancers, such as lymphoma, melanoma, and neuroendocrine tumors.

During the last decade, six new drugs have been found to increase overall survival for patients with metastatic castration-resistant prostate cancer (mCRPC). Patients with symptomatic mCRPC have initially been treated with docetaxel. Abiraterone, enzalutamide, cabazitaxel, sipuleucel, and radium-223 increase overall survival for patients who had failed treatment with docetaxel. However, randomized trials have not evaluated the drugs for patients with failure in response to second-line treatment following recurrence after docetaxel. Therefore, international organizations such as European Association of Urology (EAU)/European Society of Radiotherapy and Oncology (ESTRO) have guidelines but no recommendations for third-line treatment of mCRPC.

Due to unmet needs, the St. Gallen Advanced Prostate Cancer Consensus Conference (APCCC) 2017 favored third-line treatment with cabazitaxel and with androgen receptor (AR) and AR signaling inhibitors. Of PC, poorly differentiated, metastatic, and hormone refractory adenocarcinomas of the prostate express prostate specific membrane antigen (PSMA) and $^{68}$Ga-PSMA HBED-CC PET/CT detects sites of cancer lesions for most patients with mCRPC. Patients with a positive $^{68}$Ga-PSMA HBED-CC PET/CT might be treated with PSMA radioligand therapy (RLT).

In PC, after unsuccessful therapy with $^{90}$Y-CYT-356 monoclonal antibody (mAb), which binds to the intracellular domain of PSMA, Phase 1 and 2 clinical trials utilizing the PSMA mAb J591, radiolabelled with $^{177}$Lu or $^{90}$Y, showed promising results; however, there were higher rates of hematological toxicity. Of 47 patients treated with $^{177}$Lu-PSMA mAb J591, grade 4 thrombocytopenia in 46.8% (29.8% received platelet transfusions) was reported and a total of 25.5% experienced grade 4 neutropenia. Monoclonal antibodies are large molecules and therefore show poor permeability in solid tumors. This characteristic along with slow clearance from the circulation is the probable cause of grade 4 hematotoxicity.

Due to the side effects, there is a significant disadvantage in using Lu-J591. It is therefore prudent to consider small molecule inhibitors of PSMA instead of mAb. $^{177}$Lu-PSMA-617 and $^{177}$Lu-PSMA I&T are small-molecule inhibitors of PSMA that are extremely desirable for targeted radionuclide therapy due to their low hematotoxicity and nephrotoxicity profiles, providing better effects and fewer adverse effects than $^{177}$Lu-J591.

Despite this, there are cases where patients fail to be affected by $^{177}$Lu-PRLT treatment. In these instances, clinical application of $^{225}$Ac-PSMA targeted alpha therapy (TAT) as last line of therapy in patients with mCRPC has demonstrated an excellent response, e.g., chemotherapy naive patients, although most clinical studies report it as third-line therapy or after a failure of $^{177}$Lu-PRLT.

Widespread application of $^{225}$Ac-PSMA TAT is hampered by its salivary gland toxicity. Therefore, there exists a clinical need for an effective treatment for mCRPC with lower rates of toxicity.

SUMMARY OF THE INVENTION

Among the various aspects of the present disclosure is a radiopharmaceutical composition comprising actinium that performs as an anti-tumor agent for targeted radionuclide therapy and having improved shelf-life stability. The composition, when administered to a subject, results in low toxicity profiles, providing better effects and fewer adverse effects than monoclonal antibody treatments and other comparable third-line treatments.

Another aspect of the present disclosure is a pharmaceutical composition comprising an $^{225}$Ac-PSMA I&T solution for injection containing actinium, ascorbic acid (or sodium ascorbate), optionally an acid (e.g., hydrochloric acid), and optionally ethanol. $^{225}$Ac-PSMA-617 and $^{225}$Ac-PSMA I&T are new and promising therapy options for patients with mCRPC which contain the advantages of the aforementioned previous methods of treatments with low rates of toxicity. Another aspect of the present disclosure is $^{225}$Ac-PSMA I&T pharmaceutical composition comprising radioactive purity of at least 95.0%, at least 97.5%, at least 98.0%, at least 98.5%, at least 99.0%, at least 99.5%, or greater for at least 72-hours, 96-hours, or 120-hours after production, wherein the composition is suitable for administration (e.g., injection) to a human patient in need thereof.

In some aspects, the techniques described herein relate to a radiopharmaceutical composition including: $^{225}$Ac-PSMA I&T in an amount that provides a radioactivity concentration of about 250 kBq/mL to about 1100 kBq/mL; and sodium ascorbate in an amount of about of about 0.1 mg/mL to about 100 mg/mL; and, optionally hydrochloric acid; wherein the composition has a radiochemical purity of about 90% to about 100%; and wherein the composition has a radiochemical stability of greater than 72-hours from production when stored at about 5° C. to about 40° C.

In further aspects, the techniques described herein relate to a radiopharmaceutical composition, further including ethanol in an amount of about 1% to about 20% (v/v).

In further aspects, the techniques described herein relate to a radiopharmaceutical composition, wherein pH of the composition is from about 5.5 to about 7.5.

In further aspects, the techniques described herein relate to a radiopharmaceutical composition, wherein the composition has no metal scavengers.

In further aspects, the techniques described herein relate to a radiopharmaceutical composition, wherein the sodium ascorbate is present at 11.3 mg/mL±15%.

In further aspects, the techniques described herein relate to a radiopharmaceutical composition, wherein the composition has a radiochemical stability of greater than 120-hours at about 5° C. to about 40° C.

In further aspects, the techniques described herein relate to a radiopharmaceutical composition, wherein the radioactivity concentration is about 500 kBq/mL to about 600 kBq/mL.

In further aspects, the techniques described herein relate to a radiopharmaceutical composition, wherein the molar ratio of hydrochloric acid to sodium ascorbate is between 1:1 to 1:500.

In further aspects, the techniques described herein relate to a radiopharmaceutical composition, wherein the molar ratio of the PSMA I&T to $^{225}$Ac is from 1,000:1.0 to 5,000:1.0.

In further aspects, the techniques described herein relate to a radiopharmaceutical composition, wherein the composition has a relative biological effectiveness (RBE) of ≥4.0 for $^{225}$Ac compared to $^{177}$Lu.

In further aspects, the techniques described herein relate to a radiopharmaceutical composition, wherein the composition has a Fe, Cu, Zn, and Pb metal content of ≤0.05 μg/GBq below the detectable limit.

In another aspect, the techniques described herein relate to a method of administering a radiopharmaceutical composition, the method including injecting the composition into a patient in need thereof, the composition including $^{225}$Ac-PSMA I&T and sodium acetate in a solution having a pH of 5.5 to 7.5, wherein the solution has a radiochemical purity of more than 90% when administered.

In further aspects, the techniques described herein relate to a method, wherein the composition has a total administered dose between about 10 to about 50 mL.

In further aspects, the techniques described herein relate to a method, wherein the composition has a radiochemical purity of about 90% to about 100%, at 120-hours after storage at a temperature of 5° C. to 40° C.

In further aspects, the techniques described herein relate to a method, wherein the composition further includes hydrochloric acid and wherein the molar ratio of hydrochloric acid to sodium ascorbate of 1:0 to 1:500.

In further aspects, the techniques described herein relate to a method, wherein the composition is administered to the patient for 1 to about 6 treatment cycles.

In further aspects, the techniques described herein relate to a radiopharmaceutical composition including $^{225}$Ac-PSMA I&T, wherein the molar ratio of the PSMA I&T to $^{225}$Ac is from 1,000:1.0 to 5,000:1.0, and the composition is suitable for administration to a human patient in need thereof.

In yet another aspect, the techniques described herein relate to a radiopharmaceutical composition, wherein the composition has a molar ratio of PSMA I&T to $^{225}$Ac of about 3,225:1.0±25%.

In further aspects, the techniques described herein relate to a radiopharmaceutical composition, wherein the composition includes about 4 μg/mL to about 6 μg/mL PSMA I&T.

In further aspects, the techniques described herein relate to a radiopharmaceutical composition, wherein the composition has a radiochemical purity of about 90% to about 100%, at 120-hours after storage at a temperature of 5° C. to 40° C.

Other features and aspects of the disclosure are described in detail below.

BRIEF DESCRIPTION OF THE DRAWINGS

The patent or application file contains at least one drawing executed in color. Copies of this patent or patent application publication with color drawing(s) will be provided by the Office by request and payment of the necessary fee.

FIG. 9 depicts a patient treated with $^{225}$Ac-PSMA I&T.

FIG. 10 depicts patient characteristics with poor response to $^{225}$Ac-PSMA-617.

FIG. 11 depicts gene defects by NGS in patients with poor response to $^{225}$Ac-PSMA-617.

FIG. 12 depicts toxicities in 73 patients after $^{225}$Ac-PSMA.

FIG. 13 depicts Hematologic and kidney adverse events after $^{225}$Ac-PSMA I&T.

FIG. 14 depicts patient characteristics of the dose finding study of $^{225}$Ac-PSMA-617.

FIG. 15 depicts the dosimetry in critical organs with $^{225}$Ac-PSMA-617 and other PSMA-radionuclide therapies.

FIG. 16 depicts a summary of the outcome of the dose finding of $^{225}$Ac-PSMA.

FIG. 19 depicts radiolabeling kinetics of $^{225}$Ac-PSMA I&T at different temperature set points.

FIG. 20 depicts a summary of the radiochemical stability study of $^{225}$Ac-PSMA I&T at different pH formulations.

FIG. 27 depicts a flowchart of two $^{225}$Ac-PSMA I&T manufacturing processes.

DETAILED DESCRIPTION OF THE INVENTION

Figures 1, 2:
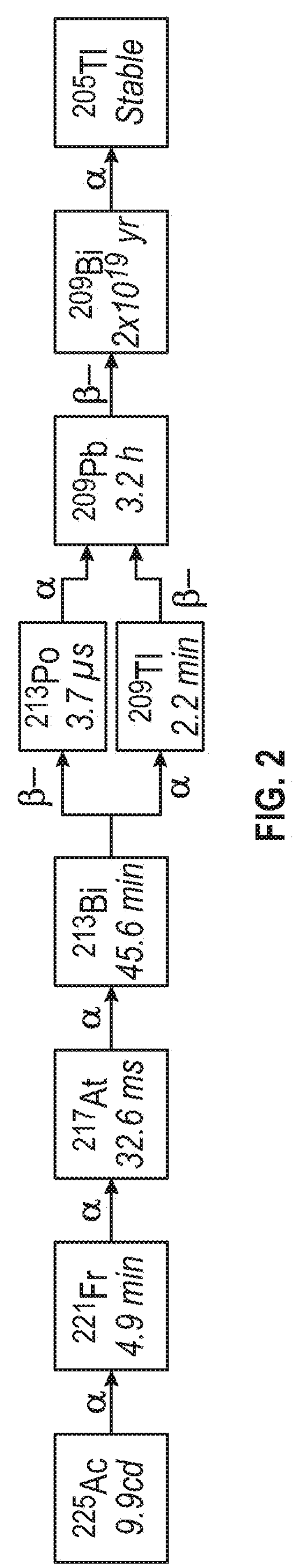
FIG. 1 presents the structural formula of the $^{225}$Ac-PSMA I&T.
FIG. 2 shows the $^{225}$Ac decay scheme.

Disclosed herein is a small molecular inhibitor of PSMA that has the desirable attributes of large monoclonal antibodies with reduced negative aspects, e.g., poor permeability and toxicity. The radiopharmaceutical composition disclosed herein comprises actinium-225 ($^{225}$Ac). $^{225}$Ac-PSMA I&T is a short-lived radiolabelled substance from which the product is formulated immediately after synthesis is finished.

Headings included herein are simply for ease of reference and are not intended to limit the disclosure in any way.

I. Definitions

Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the various embodiment(s) of the present disclosure, the articles "a", "an", "the" and "said" are intended to mean that there are one or more of the elements. The terms "comprising", "including" and "having" are intended to be inclusive and mean that there may be additional elements other than the listed elements.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, unless otherwise indicated herein, and each separate value is incorporated into the specification as if it were individually recited herein.

The term "CRPC," as used herein, refers to castrate serum testosterone <50 μg/l or 1.7 nmol/l plus one of the following types of progression: biochemical progression or radiologic progression, as defined below.

The term "biochemical progression," as used herein, refers to three consecutive rises in PSA one week apart, resulting in two 50% increases over the nadir, and PSA >2 μg/l.

The term "radiologic progression," as used herein, refers to the appearance of new lesions; either two or more new bone lesions on bone scan or a soft tissue lesion using the Response Evaluation Criteria in Solid Tumors (RECIST).

The term "PSMA," as used herein, refers to prostate-specific membrane antigen (PSMA), also known as folate hydrolase I or glutamate carboxypeptidase II, and is a type II transmembrane protein, which is anchored in the cell membrane of prostate epithelial cells. PSMA is highly expressed on prostate epithelial cells and strongly up-regulated in prostate cancer. The PSMA expression levels are directly correlated to androgen independence, metastasis, and prostate cancer progression. Thus, PSMA is a promising molecular target for diagnosis and therapy of metastatic prostate cancer at present.

The term "actinium-225 ($^{225}$Ac)," as used herein, refers to actinium-225 ($^{225}$Ac), an alpha emitter, which has been labelled to PSMA ligands as $^{225}$Ac-PSMA for targeted alpha therapy (TAT). $^{225}$Ac has a radioactive half-life of 9.9 days and decays to produce four α-particles with an energy of 5.8-8.4 MeV, with a tissue range of up to 85 μm. Alpha particles are attractive anti-tumor agents as they have a high linear energy transfer (LET) and relatively short tissue length and are able to produce double-strand DNA damage whilst minimizing toxicity to adjacent tissue, this is a far more favorable cytotoxic agent as compared to β particle emission which mainly results in single strand DNA breaks and a relatively long tissue path length which contributes to its toxicity profile.

The term "PSMA-617," as used herein, refers to a DOTA derivative of the Glu-urea-Lys motif that has been developed in the German Cancer Research Center (DKFZ) Heidelberg, Germany, for the treatment of patients with metastatic prostate cancer.

The term "PSMA I&T," as used herein, refers to $^{225}$Ac-PSMA for imaging and therapy (I&T), a third-generation derivative of PSMA-compounds which has been used here. PSMA I&T is a synonym for DOTAGA-(1-y)fk(Sub-KuE) better known as zadavotide guraxetan.

The term "(P)RLT," as used herein, refers to (Prostate) radioligand therapy, which in this context involves the systemic intravenous administration of a specific radiopharmaceutical composed of α-emitting or β-emitting radionuclide chelated to a small molecule for the purpose of delivering cytotoxic radiation to cancer cells.

The term "relative biological effectiveness (RBE)," as used herein, refers to the ratio of biological effectiveness of one type of ionizing radiation relative to another, given the same amount of absorbed energy: here β- and α-emission, between the $^{177}$Lu and $^{225}$Ac (as—biological consequence of different ionization-densities along a particle-tract). The RBE is an empirical value that varies depending on the type of ionizing radiation, the energies involved, the biological effects being considered such as cell death, and the oxygen concentration etc. RBE was 5 (for $^{225}$Ac/$^{177}$Lu) in an experimental neuroendocrine tumor model.

The term "half-life" as used herein, refers to the time required for a drug's blood or plasma concentration to decrease by one half. This decrease in drug concentration is a reflection of its excretion or elimination after absorption is complete and distribution has reached an equilibrium or quasi equilibrium state. The half-life of a drug in the blood may be determined graphically off of a pharmacokinetic plot of a drug's blood-concentration time plot, typically after intravenous administration to a sample population. The half-life can also be determined using mathematical calculations that are well known in the art. Further, as used herein the term "half-life" also includes the "apparent half-life" of a drug. The apparent half-life may be a composite number that accounts for contributions from other processes besides elimination, such as absorption, reuptake, or enterohepatic recycling.

The term "active agent" or "drug," as used herein, refers to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The terms "subject" or "patient" are used interchangeably herein and refer to a vertebrate, preferably a mammal. Mammals include, but are not limited to, humans.

II. Radiopharmaceutical Compositions Comprising Actinium $^{225}$Ac-PSMA I&T is also known by its synonyms: [$^{225}$Ac]Ac-PSMA I&T, $^{225}$Ac-PSMA-I&T, PSMA I&T AC-225, or $^{225}$Ac-DOTAGA-(I-y)fk(Sub-KuE) and has a computed IUPAC name: (25)-2-[[(1S)-1-carboxylato-5-[[8-[[(5R)-5-carboxylato-5-[[(2R)-2-[[(2R)-2-[[(4R)-4-carboxylato-4-[4,7,10-tris(carboxylatomethyl)-1,4,7,10-tetrazacyclododec-1-yl]butanoyl]amino]-3-(4-hydroxy-3-iodophenyl)propanoyl]amino]-3-phenylpropanoyl]amino]pentyl]amino]-8-oxooctanoyl]amino]pentyl]carbamoylamino]pentanedioate; hydron; actinium-225(3+); The molecular formula $C_{63}H_{88}IAcN_{11}O_{23}$ has a relative molecular mass of 1719.4 g/mol.

The labelled-substance; $^{225}$Ac-PSMA I&T is labelled with actinium-225 ($T_{1/2}$=9.9d) solution. The synthetized $^{225}$Ac-PSMA I&T solution is formulated in an injection grade water solution containing stabilizing agents. The solution is sterilized by aseptic filtration through a 0.22 μm filter prior to dispensing in multidose vials (e.g., single use vials and/or single dose vials). Administration of the formulated solution may occur within 120 h of the end of the synthesis (EOS) after quality control and batch release of the drug product. In other embodiments, administration of the formulated solution may occur later than 120 h of the end of the synthesis after quality control and batch release of the drug product.

The presently disclosed radiopharmaceutical composition has a shelf life at temperatures ranging from 5° C.±3° C. to 40° C.±2° C. In some embodiments, the presently disclosed radiopharmaceutical composition has a shelf life ≥24 hours, ≥48 hours, ≥72 hours, ≥96 hours, or ≥120 hours when stored at temperatures ranging from 5° C.±3° C. to 40° C.±2° C. In another embodiment, the radiopharmaceutical composition has a shelf life at temperatures ranging from 2° C.-25° C. In some embodiments, the presently disclosed radiopharmaceutical composition has a shelf life ≥24 hours, ≥48 hours, ≥72 hours, ≥96 hours, or ≥120 hours when stored at temperatures ranging from 2° C.-25° C. The radiopharmaceutical composition also meets the requirements for sterility and bacterial endotoxins according to the European pharmacopoeia confirming an acceptable manufacturing process from a microbial point of view.

Due to the highly atypical properties of the $^{225}$Ac-labelled molecule (short half-life and picomolar quantities synthesized), an indirect approach for structural confirmation of $^{225}$Ac-PSMA I&T is used. As actinium does not have a stable form, a Lu-labelled peptide has been used to verify the structure of the labelled precursor. As lutetium labelled PSMA I&T has very similar chemical characteristics to actinium labelled PSMA I&T, in both a stable and a radioactive form, it can be used as a reference standard in combination with unlabelled PSMA I&T for the identification method.

Immediately after production, a sample of $^{225}$Ac-PSMA I&T solution is spotted onto a TLC plate, which is then developed and analysed using a High Purity Germanium (HPGe) Radiation Detector. A sample of $^{225}$Ac-PSMA I&T solution is also analysed using analytical high-performance liquid chromatography (HPLC). A $^{nat}$Lu-PSMA I&T and unlabelled PSMA I&T are used as reference standards in the method.

In a first embodiment, the presently disclosed medicinal product is a sterile filtered radiopharmaceutical solution containing a micro dose of $^{225}$Ac-PSMA I&T solution in a 42.5 mg/ml aqueous ascorbic acid solution containing 59 mg/ml ethanol. The product is diluted to a standard concentration and therefore the final volume of the bulk product varies depending on the starting activity introduced. The composition of the medicinal product in this embodiment is depicted below in Table 1:

TABLE 1

Composition of medicinal product of a first embodiment*

| Component | Quantity | Function |
|---|---|---|
| $^{225}$Ac-PSMA I&T | q.s.** | API |
| Ethanol | 59 mg | Vehicle/Stabilizing agent (radiolysis) |
| Ascorbic acid | 42.5 mg | Stabilizing agent (radiolysis) |
| Disodium EDTA | 21 μg | Metal ion chelator |
| Sodium bicarbonate | q.s. | pH adjuster |
| Sodium hydroxide | q.s. | pH adjuster |
| Water for Injection | ad 1 ml | Vehicle |

*Max volume per vial is 10 ml

**sufficient amount of radioactivity for intended use.

In some embodiments, the radioactivity of the composition may be about 1 MBq to about 2 MBq, about 2 MBq to about 3 MBq, about 3 MBq to about 4 MBq, about 4 MBq to about 5 MBq, about 5 MBq to about 6 MBq, about 6 MBq to about 7 MBq, about 7 MBq to about 8 MBq, about 8 MBq to about 9 MBq, about 9 MBq to about 10 MBq, about 11 MBq to about 12 MBq, about 12 MBq to about 13 MBq, about 13 MBq to about 14 MBq, about 14 MBq to about 15 MBq, about 15 MBq to about 16 MBq, about 16 MBq to about 17 MBq, about 17 MBq to about 18 MBq, about 18 MBq to about 19 MBq, about 19 MBq to about 20 MBq, about 20 MBq to about 21 MBq, about 21 MBq to about 22 MBq, about 22 MBq to about 23 MBq, about 23 MBq to about 24 MBq, or about 24 MBq to about 25 MBq.

In another embodiment, the presently disclosed medicinal product is a sterile filtered radiopharmaceutical solution containing a microdose of $^{225}$Ac-PSMA I&T solution in an aqueous ascorbic acid solution. The composition of the medicinal product in this embodiment is depicted below in Table 2:

TABLE 2

Composition of $^{225}$Ac-PSMA I&T injection of a second embodiment

| Component | Quantity per ml | Quantity per 20 ml* | Function |
|---|---|---|---|
| $^{225}$Ac-PSMA I&T | 0.5-0.6 MBq (13.5-16.2 μCi) | 6-9 MBq (0.16-0.24 mCi) | Radioactive pharmaceutical ingredient (exact activity/volume adjusted according to dose strength) |
| $^{225}$Ac-PSMA I&T, PSMA I&T and M-PSMA I&T** compounds | ≤7.5 μg/ml | ≤0.1 mg | Mass of pharmaceutical ingredient |
| Sodium Ascorbate | 11.2 mg/ml | 224 mg | Radiolysis stabilizer |
| Hydrochloric Acid (HCl)‡ | 5.4 mg | 108 mg | Vehicle ($^{225}Ac^{3+}$) |
| Sodium Hydroxide (NaOH)§ | 5.3 mg | 106 mg | Adjust pH |
| Water for Injection | Sufficient to make 1 ml | Sufficient to make 20 ml | Vehicle |

*Depending on the actual size of the dose and the radioactive strength of each batch, the volume dispensed into the 20 ml vial may vary between 10-20 ml.

**M-PSMA I&T is metal-PSMA I&T, where metal M can be any metal such as Zn, Fe, Ni, Pb, or Cu, including $^{225}$Ac.

‡Hydrochloric acid is used for dissolving $^{225}Ac^{3+}$.

§Sodium hydroxide has been added as a pH adjuster to ensure a pH between 5.5 and 7.0.

In some embodiments, the radioactivity of the composition per mL may be about 0.1 MBq/ml to about 0.2 MBq/ml, about 0.2 MBq/ml to about 0.3 MBq/ml, about 0.3 MBq/ml to about 0.4 MBq/ml, about 0.4 MBq/ml to about 0.5 MBq/ml, about 0.5 MBq/ml to about 0.6 MBq/ml, about 0.6 MBq/ml to about 0.7 MBq/ml, about 0.7 MBq/ml to about 0.8 MBq/ml, about 0.8 MBq/ml to about 0.9 MBq/ml, about 0.9 MBq/ml to about 1.0 MBq/ml, about 1.0 MBq/ml to about 1.1 MBq/ml, about 1.1 MBq/ml to about 1.2 MBq/ml, about 1.2 MBq/ml to about 1.3 MBq/ml, about 1.3 MBq/ml to about 1.4 MBq/ml, about 1.4 MBq/ml to about 1.5 MBq/ml, about 1.5 MBq/ml to about 1.6 MBq/ml, about 1.6 MBq/ml to about 1.7 MBq/ml, about 1.7 MBq/ml to about 1.8 MBq/ml, about 1.8 MBq/ml to about 1.9 MBq/ml, about 1.9 MBq/ml to about 2.0 MBq/ml, about 2.0 MBq/ml to about 2.1 MBq/ml, about 2.1 MBq/ml to about 2.2 MBq/ml, about 2.2 MBq/ml to about 2.3 MBq/ml, about 2.3 MBq/ml to about 2.4 MBq/ml, about 2.4 MBq/ml to about 2.5 MBq/ml, about 2.5 MBq/ml to about 2.6 MBq/ml, about 2.6 MBq/ml to about 2.7 MBq/ml, about 2.7 MBq/ml to about 2.8 MBq/ml, about 2.8 MBq/ml to about 2.9 MBq/ml, about 2.9 MBq/ml to about 3.0 MBq/ml, about 3.0 MBq/ml to about 3.1 MBq/ml, about 3.1 MBq/ml to about 3.2 MBq/ml, about 3.2 MBq/ml to about 3.3 MBq/ml, about 3.3 MBq/ml to about 3.4 MBq/ml, about 3.4 MBq/ml to about 3.5 MBq/ml, about 3.5 MBq/ml to about 3.6 MBq/ml, about 3.6 MBq/ml to about 3.7 MBq/ml, about 3.7 MBq/ml to about 3.8 MBq/ml, about 3.8 MBq/ml to about 3.9 MBq/ml, or about 3.9 MBq/ml to about 4.0 MBq/ml.

In some embodiments, the radiopharmaceutical composition may have a specific activity from about 0.005 MBq/nmol to about 0.010 MBq/nmol, from about 0.010 MBq/nmol to about 0.015 MBq/nmol, from about 0.015 MBq/nmol to about 0.020 MBq/nmol, from about 0.020 MBq/nmol to about 0.025 MBq/nmol, from about 0.025 MBq/nmol to about 0.030 MBq/nmol, from about 0.030 MBq/nmol to about 0.035 MBq/nmol, from about 0.035 MBq/nmol to about 0.040 MBq/nmol, from about 0.040 MBq/nmol to about 0.045 MBq/nmol, from about 0.045 MBq/nmol to about 0.050 MBq/nmol, from about 0.050 MBq/nmol to about 0.055 MBq/nmol, from about 0.055 MBq/nmol to about 0.060 MBq/nmol, from about 0.060 MBq/nmol to about 0.065 MBq/nmol, from about 0.065 MBq/nmol to about 0.070 MBq/nmol, from about 0.070 MBq/nmol to about 0.075 MBq/nmol, from about 0.075 MBq/nmol to about 0.080 MBq/nmol, from about 0.080 MBq/nmol to about 0.085 MBq/nmol, from about 0.085 MBq/nmol to about 0.090 MBq/nmol, from about 0.090 MBq/nmol to about 0.095 MBq/nmol, from about 0.095 MBq/nmol to about 0.100 MBq/nmol, from about 0.100 MBq/nmol to about 0.105 MBq/nmol, from about 0.105 MBq/nmol to about 0.110 MBq/nmol, from about 0.110 MBq/nmol to about 0.115 MBq/nmol, from about 0.115 MBq/nmol to about 0.120 MBq/nmol, from about 0.120 MBq/nmol to about 0.125 MBq/nmol, from about 0.125 MBq/nmol to about 0.130 MBq/nmol, from about 0.130 MBq/nmol to about 0.135 MBq/nmol, from about 0.135 MBq/nmol to about 0.140 MBq/nmol, from about 0.140 MBq/nmol to about 0.145 MBq/nmol, from about 0.145 MBq/nmol to about 0.150 MBq/nmol, from about 0.150 MBq/nmol to about 0.155 MBq/nmol, from about 0.155 MBq/nmol to about 0.160 MBq/nmol, from about 0.160 MBq/nmol to about 0.165 MBq/nmol, from about 0.165 MBq/nmol to about 0.170 MBq/nmol, or from about 0.170 MBq/nmol to about 0.175 MBq/nmol.

In some embodiments, the radiopharmaceutical composition may comprise from about 0.0010 nmol to about 0.0020 nmol of $^{225}$Ac, from about 0.0020 nmol to about 0.0030 nmol of $^{225}$Ac, from about 0.0030 nmol to about 0.0040 nmol of $^{225}$Ac, from about 0.0040 nmol to about 0.0050 nmol of $^{225}$Ac, from about 0.0050 nmol to about 0.0060 nmol of $^{225}$Ac, from about 0.0060 nmol to about 0.0070 nmol of $^{225}$Ac, from about 0.0070 nmol to about 0.0080 nmol of $^{225}$Ac, from about 0.0080 nmol to about 0.0090 nmol of $^{225}$Ac, from about 0.0090 nmol to about 0.0100 nmol of $^{225}$Ac, from about 0.0100 nmol to about 0.0110 nmol of $^{225}$Ac, from about 0.0110 nmol to about 0.0120 nmol of $^{225}$Ac, from about 0.0120 nmol to about 0.0130 nmol of $^{225}$Ac, from about 0.0130 nmol to about 0.0140 nmol of $^{225}$Ac, from about 0.0140 nmol to about 0.0150 nmol of $^{225}$Ac, from about 0.0150 nmol to about 0.0160 nmol of $^{225}$Ac, from about 0.0160 nmol to about 0.0170 nmol of $^{225}$Ac, from about 0.0170 nmol to about 0.0180 nmol of $^{225}$Ac, from about 0.0180 nmol to about 0.0190 nmol of $^{225}$Ac, from about 0.0190 nmol to about 0.0200 nmol of $^{225}$Ac, from about 0.0200 nmol to about 0.0210 nmol of $^{225}$Ac, from about 0.0210 nmol to about 0.0220 nmol of $^{225}$Ac, from about 0.0220 nmol to about 0.0230 nmol of $^{225}$Ac, from about 0.0230 nmol to about 0.0240 nmol of $^{225}$Ac, from about 0.0240 nmol to about 0.0250 nmol of $^{225}$Ac, from about 0.0250 nmol to about 0.0260 nmol of $^{225}$Ac, from about 0.0260 nmol to about 0.0270 nmol of $^{225}$Ac, from about 0.0270 nmol to about 0.0280 nmol of $^{225}$Ac, from about 0.0280 nmol to about 0.0290 nmol of $^{225}$Ac, from about 0.0290 nmol to about 0.0300 nmol of $^{225}$Ac, from about 0.0300 nmol to about 0.0310 nmol of $^{225}$Ac, from about 0.0310 nmol to about 0.0320 nmol of $^{225}$Ac, from about 0.0320 nmol to about 0.0330 nmol of $^{225}$Ac, from about 0.0330 nmol to about 0.0340 nmol of $^{225}$Ac, from about 0.0340 nmol to about 0.0350 nmol of $^{225}$Ac, from about 0.0350 nmol to about 0.0360 nmol of $^{225}$Ac, from about 0.0360 nmol to about 0.0370 nmol of $^{225}$Ac, from about 0.0370 nmol to about 0.0380 nmol of $^{225}$Ac, from about 0.0380 nmol to about 0.0390 nmol of $^{225}$Ac, or from about 0.0390 nmol to about 0.0400 nmol of $^{225}$Ac.

In other embodiments, the total amount of $^{225}$Ac-PSMA I&T present in the radiopharmaceutical composition can and will vary. In some embodiments, the total amount of $^{225}$Ac-PSMA I&T present in the radiopharmaceutical composition may range from about 9 μg/ml to 20 μg/ml, 10 μg/ml to 20 μg/ml, 11 μg/ml to 20 μg/ml, 11 μg/ml to 15 μg/ml, 11 μg/ml to 14 μg/ml, or 11 μg/ml to 13 μg/ml. In another embodiment, the total amount of $^{225}$Ac-PSMA I&T in the radiopharmaceutical composition may range from about 5 μg/ml to about 15 μg/ml. In another embodiment, the total amount of $^{225}$Ac-PSMA I&T in the radiopharmaceutical composition may be less than or equal to about 7.5 μg/ml. In various embodiments, the total amount of $^{225}$Ac-PSMA I&T present in the radiopharmaceutical composition may be about 1.0 μg/ml, about 1.5 μg/ml, about 2.0 μg/ml, about 2.5 μg/ml, about 3.0 μg/ml, about 3.5 μg/ml, about 4.0 μg/ml, about 4.5 μg/ml, about 5.0 μg/ml, about 5.5 μg/ml, about 6.0 μg/ml, about 6.5 μg/ml, about 7.0 μg/ml, about 7.5 μg/ml, about 8.0 μg/ml, about 8.5 μg/ml, about 9.0 μg/ml, about 9.5 μg/ml, about 10.0 μg/ml, about 10.5 μg/ml, about 11.0 μg/ml, about 11.5 μg/ml, about 12.0 μg/ml, about 12.5 μg/ml, about 13.0 μg/ml, about 13.5 μg/ml, about 14.0 μg/ml, about 14.5 μg/ml, about 15.0 μg/ml, about 15.5 μg/ml, about 16.0 μg/ml, about 16.5 μg/ml, about 17.0 μg/ml, about 17.5 μg/ml, or about 18.0 μg/ml. In other various embodiments, the total amount of $^{225}$Ac-PSMA I&T present in the radiopharmaceutical composition may be about 1.0 μg/ml to about 1.5 μg/ml, about 1.5 μg/ml to about 2.0 μg/ml, about 2.0 μg/ml to about 2.5 μg/ml, about 2.5 μg/ml to about 3.0 μg/ml, about 3.0 μg/ml to about 3.5 μg/ml, about 3.5 μg/ml to about 4.0 μg/ml, about 4.0 μg/ml to about 4.5 μg/ml, about 4.5 μg/ml to about 5.0 μg/ml, about 5.0 μg/ml to about 5.5 μg/ml, about 5.5 μg/ml to about 6.0 μg/ml, about 6.0 μg/ml to about 6.5 μg/ml, about 6.5 μg/ml to about 7.0 μg/ml, about 7.0 μg/ml to about 7.5 μg/ml, about 7.5 μg/ml to about 8.0 μg/ml, about 8.0 μg/ml to about 8.5 μg/ml, about 8.5 μg/ml to about 9.0 μg/ml, about 9.0 μg/ml to about 9.5 μg/ml, about 9.5 μg/ml to about 10.0 μg/ml, about 10.0 μg/ml to about 10.5 μg/ml, about 10.5 μg/ml to about 11.0 μg/ml, about 11.0 μg/ml to about 11.5 g/ml, about 11.5 μg/ml to about 12.0 μg/ml, about 12.0 μg/ml to about 12.5 μg/ml, about 12.5 μg/ml to about 13.0 μg/ml, about 13.0 μg/ml to about 13.5 μg/ml, about 13.5 μg/ml to about 14.0 μg/ml, about 14.0 μg/ml to about 14.5 μg/ml, about 14.5 μg/ml to about 15.0 μg/ml, about 15.0 μg/ml to about 15.5 μg/ml, about 15.5 μg/ml to about 16.0 μg/ml, about 16.0 μg/ml to about 16.5 μg/ml, about 16.5 μg/ml to about 17.0 μg/ml, about 17.0 μg/ml to about 17.5 μg/ml, or about 17.5 μg/ml to about 18.0 μg/ml.

In another embodiment, the total amount of PSMA I&T present in the radiopharmaceutical composition can and will vary. In some embodiments, the total amount of PSMA I&T present in the radiopharmaceutical composition may be ≤12.0 μg/ml, ≤11.9 μg/ml, ≤11.8 μg/ml, ≤11.7 μg/ml, ≤11.6 μg/ml, ≤11.5 μg/ml, ≤11.4 μg/ml, ≤11.3 μg/ml, ≤11.2 μg/ml, ≤11.1 μg/ml, ≤11.0 μg/ml, ≤10.9 μg/ml, ≤10.8 μg/ml, ≤10.7 μg/ml, ≤10.6 μg/ml, ≤10.5 μg/ml, ≤10.4 μg/ml, ≤10.3 μg/ml, ≤10.2 μg/ml, ≤10.1 μg/ml, ≤10.0 μg/ml, ≤9.9 μg/ml, ≤9.8 μg/ml, ≤9.7 μg/ml, ≤9.6 μg/ml, ≤9.5 μg/ml, ≤9.4 μg/ml, ≤9.3 μg/ml, ≤9.2 μg/ml, ≤9.1 μg/ml, ≤9.0 μg/ml, ≤8.9 μg/ml, ≤8.8 μg/ml, ≤8.7 μg/ml, ≤8.6 μg/ml, ≤8.5 μg/ml, ≤8.4 μg/ml, ≤8.3 μg/ml, ≤8.2 μg/ml, ≤8.1 μg/ml, ≤8.0 μg/ml, ≤7.9 μg/ml, ≤7.8 μg/ml, ≤7.7 μg/ml, ≤7.6 μg/ml, ≤7.5 μg/ml, ≤7.4 μg/ml, ≤7.3 μg/ml, ≤7.2 μg/ml, ≤7.1 μg/ml, ≤7.0 μg/ml, ≤6.9 μg/ml, ≤6.8 μg/ml, ≤6.7 μg/ml, ≤6.6 μg/ml, ≤6.5 μg/ml, ≤6.4 μg/ml, ≤6.3 μg/ml, ≤6.2 μg/ml, ≤6.1 μg/ml, ≤6.0 μg/ml, ≤5.9 μg/ml, ≤5.8 μg/ml, ≤5.7 μg/ml, ≤5.6 μg/ml, ≤5.5 μg/ml, ≤5.4 μg/ml, ≤5.3 μg/ml, ≤5.2 μg/ml, ≤5.1 μg/ml, ≤5.0 μg/ml, ≤4.9 μg/ml, ≤4.8 μg/ml, ≤4.7 μg/ml, ≤4.6 μg/ml, ≤4.5 μg/ml, ≤4.4 μg/ml, ≤4.3 μg/ml, ≤4.2 μg/ml, ≤4.1 μg/ml, ≤4.0 μg/ml, ≤3.9 μg/ml, ≤3.8 μg/ml, ≤3.7 μg/ml, ≤3.6 μg/ml, ≤3.5 μg/ml, ≤3.4 μg/ml, ≤3.3 μg/ml, ≤3.2 μg/ml, ≤3.1 μg/ml, ≤3.0 μg/ml, ≤2.9 μg/ml, ≤2.8 μg/ml, ≤2.7 μg/ml, ≤2.6 μg/ml, ≤2.5 μg/ml, ≤2.4 μg/ml, ≤2.3 μg/ml, ≤2.2 μg/ml, ≤2.1 μg/ml, ≤2.0 μg/ml, ≤1.9 μg/ml, ≤1.8 μg/ml, ≤1.7 μg/ml, ≤1.6 μg/ml, ≤1.5 μg/ml, ≤1.4 μg/ml, ≤1.3 μg/ml, ≤1.2 μg/ml, ≤1.1 μg/ml, or ≤1.0 μg/ml.

In another embodiment, the total amount of other impurities present in the radiopharmaceutical composition can and will vary. In some embodiments, the total amount of other impurities present in the radiopharmaceutical composition may be ≤12.0 μg/ml, ≤11.9 μg/ml, ≤11.8 μg/ml, ≤11.7 μg/ml, ≤11.6 μg/ml, ≤11.5 μg/ml, ≤11.4 μg/ml, ≤11.3 μg/ml, ≤11.2 μg/ml, ≤11.1 μg/ml, ≤11.0 μg/ml, ≤10.9 μg/ml, ≤10.8 μg/ml, ≤10.7 μg/ml, ≤10.6 μg/ml, ≤10.5 μg/ml, ≤10.4 μg/ml, ≤10.3 μg/ml, ≤10.2 μg/ml, ≤10.1 μg/ml, ≤10.0 μg/ml, ≤9.9 μg/ml, ≤9.8 μg/ml, ≤9.7 μg/ml, ≤9.6 μg/ml, ≤9.5 μg/ml, ≤9.4 μg/ml, ≤9.3 μg/ml, ≤9.2 μg/ml, ≤9.1 μg/ml, ≤9.0 μg/ml, ≤8.9 μg/ml, ≤8.8 μg/ml, ≤8.7 μg/ml, ≤8.6 μg/ml, ≤8.5 μg/ml, ≤8.4 μg/ml, ≤8.3 μg/ml, ≤8.2 μg/ml, ≤8.1 μg/ml, ≤8.0 μg/ml, ≤7.9 μg/ml, ≤7.8 μg/ml, ≤7.7 μg/ml, ≤7.6 μg/ml, ≤7.5 μg/ml, ≤7.4 μg/ml, ≤7.3 μg/ml, ≤7.2 μg/ml, ≤7.1 μg/ml, ≤7.0 μg/ml, ≤6.9 μg/ml, ≤6.8 μg/ml, ≤6.7 μg/ml, ≤6.6 μg/ml, ≤6.5 μg/ml, ≤6.4 μg/ml, ≤6.3 μg/ml, ≤6.2 μg/ml, <6.1 μg/ml, ≤6.0 μg/ml, ≤5.9 μg/ml, ≤5.8 μg/ml, ≤5.7 μg/ml, ≤5.6 μg/ml, ≤5.5 μg/ml, ≤5.4 μg/ml, ≤5.3 μg/ml, ≤5.2 μg/ml, ≤5.1 μg/ml, ≤5.0 μg/ml, ≤4.9 μg/ml, ≤4.8 μg/ml, ≤4.7 μg/ml, ≤4.6 μg/ml, ≤4.5 μg/ml, ≤4.4 μg/ml, ≤4.3 μg/ml, ≤4.2 μg/ml, ≤4.1 μg/ml, ≤4.0 μg/ml, ≤3.9 μg/ml, ≤3.8 μg/ml, ≤3.7 μg/ml, ≤3.6 μg/ml, ≤3.5 μg/ml, ≤3.4 μg/ml, ≤3.3 μg/ml, ≤3.2 μg/ml, ≤3.1 μg/ml, ≤3.0 μg/ml, ≤2.9 μg/ml, ≤2.8 μg/ml, ≤2.7 μg/ml, ≤2.6 μg/ml, ≤2.5 μg/ml, ≤2.4 μg/ml, ≤2.3 μg/ml, ≤2.2 μg/ml, ≤2.1 μg/ml, ≤2.0 μg/ml, ≤1.9 μg/ml, ≤1.8 μg/ml, ≤1.7 μg/ml, ≤1.6 μg/ml, ≤1.5 μg/ml, ≤1.4 μg/ml, ≤1.3 μg/ml, ≤1.2 μg/ml, ≤1.1 μg/ml, or ≤1.0 μg/ml.

In other embodiments, the total amount of $^{225}$Ac-PSMA I&T present in the radiopharmaceutical composition can and will vary. In some embodiments, the total amount of $^{225}$Ac-PSMA I&T present in the radiopharmaceutical composition may range from about 9 μg/ml to 20 μg/ml, 10 μg/ml to 20 μg/ml, 11 μg/ml to 20 μg/ml, 11 μg/ml to 15 μg/ml, 11 μg/ml to 14 μg/ml, or 11 μg/ml to 13 μg/ml. In another embodiment, the total amount of $^{225}$Ac-PSMA I&T in the radiopharmaceutical composition may range from about 5 μg/ml to about 15 μg/ml. In another embodiment, the total amount of $^{225}$Ac-PSMA I&T in the radiopharmaceutical composition may be less than or equal to about 7.5 μg/ml. In various embodiments, the total amount of $^{225}$Ac-PSMA I&T present in the radiopharmaceutical composition may be about 1.0 μg/ml, about 1.5 μg/ml, about 2.0 μg/ml, about 2.5 μg/ml, about 3.0 μg/ml, about 3.5 μg/ml, about 4.0 μg/ml, about 4.5 μg/ml, about 5.0 μg/ml, about 5.5 μg/ml, about 6.0 μg/ml, about 6.5 μg/ml, about 7.0 μg/ml, about 7.5 μg/ml, about 8.0 μg/ml, about 8.5 μg/ml, about 9.0 μg/ml, about 9.5 μg/ml, about 10.0 μg/ml, about 10.5 g/ml, about 11.0 μg/ml, about 11.5 μg/ml, about 12.0 μg/ml, about 12.5 μg/ml, about 13.0 μg/ml, about 13.5 μg/ml, about 14.0 μg/ml, about 14.5 μg/ml, about 15.0 μg/ml, about 15.5 μg/ml, about 16.0 μg/ml, about 16.5 μg/ml, about 17.0 μg/ml, about 17.5 μg/ml, or about 18.0 μg/ml. In other various embodiments, the total amount of $^{225}$Ac-PSMA I&T present in the radiopharmaceutical composition may be about 1.0 μg/ml to about 1.5 μg/ml, about 1.5 μg/ml to about 2.0 μg/ml, about 2.0 μg/ml to about 2.5 μg/ml, about 2.5 μg/ml to about 3.0 μg/ml, about 3.0 μg/ml to about 3.5 μg/ml, about 3.5 μg/ml to about 4.0 μg/ml, about 4.0 μg/ml to about 4.5 μg/ml, about 4.5 μg/ml to about 5.0 μg/ml, about 5.0 μg/ml to about 5.5 μg/ml, about 5.5 μg/ml to about 6.0 μg/ml, about 6.0 μg/ml to about 6.5 μg/ml, about 6.5 μg/ml to about 7.0 μg/ml, about 7.0 μg/ml to about 7.5 μg/ml, about 7.5 μg/ml to about 8.0 μg/ml, about 8.0 μg/ml to about 8.5 μg/ml, about 8.5 μg/ml to about 9.0 μg/ml, about 9.0 μg/ml to about 9.5 μg/ml, about 9.5 μg/ml to about 10.0 μg/ml, about 10.0 μg/ml to about 10.5 μg/ml, about 10.5 μg/ml to about 11.0 μg/ml, about 11.0 μg/ml to about 11.5 μg/ml, about 11.5 μg/ml to about 12.0 μg/ml, about 12.0 μg/ml to about 12.5 μg/ml, about 12.5 g/ml to about 13.0 μg/ml, about 13.0 μg/ml to about 13.5 μg/ml, about 13.5 μg/ml to about 14.0 μg/ml, about 14.0 μg/ml to about 14.5 μg/ml, about 14.5 μg/ml to about 15.0 μg/ml, about 15.0 μg/ml to about 15.5 μg/ml, about 15.5 μg/ml to about 16.0 μg/ml, about 16.0 μg/ml to about 16.5 μg/ml, about 16.5 μg/ml to about 17.0 μg/ml, about 17.0 μg/ml to about 17.5 μg/ml, or about 17.5 μg/ml to about 18.0 μg/ml.

The total amount of ethanol present in the radiopharmaceutical composition can and will vary. In some embodiments, the total amount of ethanol present in the radiopharmaceutical composition may range from about 0 mg to 120 mg, 40 mg to 120 mg, about 50 to 90 mg, about 50 to 80 mg, or about 60 to 80 mg. In another embodiment, the total amount of ethanol in the radiopharmaceutical composition may range from about 65 mg to about 80 mg. In various embodiments, the total amount of ethanol present in the radiopharmaceutical composition may be about 40 mg, 45 mg, 50 mg, 55 mg, 60 mg, 65 mg, 70 mg, 71 mg, 72 mg, 73 mg, 74 mg, 75 mg, 76 mg, 77, mg, 78, mg, 79 mg, 80 mg, 85 mg, 90 mg, 95 mg, 100 mg, 105 mg, 110 mg, 115 mg, or 120 mg. In one embodiment, the total amount of ethanol in the radiopharmaceutical composition may be about 52 mg. In another embodiment, the total amount of ethanol in the radiopharmaceutical composition may be about 59 mg. In yet another embodiment, the total amount of ethanol in the radiopharmaceutical composition may be about 68 mg. In a further embodiment, the ratio of ethanol in the radiopharmaceutical composition may be about 53 mg per 10 ml. In another embodiment, the ratio of ethanol in the radiopharmaceutical composition may be about 59 mg per 10 ml. In still another embodiment, the ratio of ethanol in the radiopharmaceutical composition may be about 61 mg per 10 ml. In various embodiments, ethanol may be present in the radiopharmaceutical composition in an amount of about 5 mg/ml to about 100 mg/ml, about 10 mg/ml to about 100 mg/ml, about 15 mg/ml to about 100 mg/ml, about 20 mg/ml to about 100 mg/ml, about 25 mg/ml to about 100 mg/ml, about 30 mg/ml to about 100 mg/ml, about 35 mg/ml to about 100 mg/ml, about 40 mg/ml to about 100 mg/ml, about 45 mg/ml to about 100 mg/ml, about 50 mg/ml to about 100 mg/ml, about 55 mg/ml to about 100 mg/ml, about 60 mg/ml to about 100 mg/ml, about 65 mg/ml to about 100 mg/ml, or about 70 mg/ml to about 100 mg/ml. In yet another embodiment, the amount of ethanol present in the radiopharmaceutical composition may be at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, or at least 70 mg/ml.

The total amount of ascorbic acid (or ascorbate salt such as sodium ascorbate) in the radiopharmaceutical composition can and will vary. In some embodiments, the total amount of ascorbic acid present in the radiopharmaceutical composition may range from about 20 mg to 90 mg, about 20 to 80 mg, about 20 to 70 mg, about 20 to 60 mg, about 20 to 50 mg, about 25 to 50 mg, about 30 to 50 mg or about 35 to 45 mg. In another embodiment, the total amount of ascorbic acid in the radiopharmaceutical composition may range from about 5 mg to about 50 mg. In various embodiments, the total amount of ascorbic acid present in the radiopharmaceutical composition may be about 5 mg, 10 mg, 15 mg, 20 mg, 25 mg, 30 mg, 35 mg, 36 mg, 37 mg, 38 mg, 39 mg, 40 mg, 40.5 mg, 41 mg, 41.5 mg, 42 mg, 42.5 mg, 43 mg, 43.5 mg, 44 mg, 44.5 mg, 45 mg, 50 mg, 55 mg, 60 mg, 65 mg, 70 mg, 75 mg, 80 mg, 85 mg, or 90 mg. In one embodiment, the total amount of ascorbic acid in the radiopharmaceutical composition may be about 41.5 mg. In another embodiment, the total amount of ascorbic acid in the radiopharmaceutical composition may be about 40.5 mg. In yet another embodiment, the total amount of ascorbic acid in the radiopharmaceutical composition may be about 44.5 mg. In a further embodiment, the ratio of ascorbic acid in the radiopharmaceutical composition may be about 40.5 mg per 10 ml. In another embodiment, the ratio of ascorbic acid in the radiopharmaceutical composition may be about 42.5 mg per 10 ml. In still another embodiment, the ratio of ascorbic acid in the radiopharmaceutical composition may be about 44.5 mg per 10 ml. In yet another embodiment, the percentage of ascorbic acid concentration in the radiopharmaceutical composition may be about 5 to about 70 mg/ml, about 5 to about 10 mg/ml, about 5 to about 15 mg/ml, about 5 to about 20 mg/ml, about 5 to about 25 mg/ml, about 10 to about 80 mg/ml, about 10 to about 75 mg/ml, about 10 to about 70 mg/ml, about 15 to about 80 mg/ml, about 15 to about 75 mg/ml, about 15 to about 70 mg/ml, about 20 to about 80 mg/ml, about 20 to about 75 mg/ml, about 20 to about 70 mg/ml, about 25 mg/ml to about 70 mg/ml, or about 30 to about 70 mg/ml. In various embodiments, the amount of ascorbic acid in the radiopharmaceutical composition may be at least 5 mg/ml, at least 10 mg/ml, at least 15 mg/ml, at least 20 mg/ml, at least 25 mg/ml, at least 30 mg/ml, at least 35 mg/ml, at least 40 mg/ml. In various embodiments, the amount of ascorbic acid (or ascorbate salt such as sodium ascorbate) in the radiopharmaceutical composition may be around 5.7 mg/ml±15%, around 11.3 mg/ml±15%, or around 17 mg/ml=15%.

The total amount of acid (e.g., hydrochloric acid or any other suitable acid) in the radiopharmaceutical composition can and will vary. The molar ratio of acid to ascorbic acid may generally range between hydrochloric acid to sodium ascorbate of 1:0 to 1:500, 1:1 to 1:400, 1:1 to 1:300, 1:1 to 1:150, 1:1 to 1:200, 1:1 to 1:100, 1:1 to 1:75, 1:1 to 1:50, 1:1 to 1:30, 1:1 to 1:20, 1:1 to 1:15, 1:1 to 1:10, or 1:1 to 1:5. For example, the molar ratio of hydrochloric acid to sodium ascorbate may generally range between hydrochloric acid to sodium ascorbate of 1:0 to 1:500, 1:1 to 1:400, 1:1 to 1:300, 1:1 to 1:150, 1:1 to 1:200, 1:1 to 1:100, 1:1 to 1:75, 1:1 to 1:50, 1:1 to 1:30, 1:1 to 1:20, 1:1 to 1:15, 1:1 to 1:10, or 1:1 to 1:5.

One aspect of the present disclosure provides for heating the pharmaceutical composition to a temperature of about 75° C. or greater, 80° C. or greater, 85° C. or greater, 90° C. or greater, 95° C. or greater, 100° C. or greater, 105° C. or greater, 110° C. or greater, or greater 115° C., or 120° C. or greater. In one embodiment, the pharmaceutical composition is heated for at least 5 minutes, 9 minutes, or 15 minutes. In a further embodiment, the pharmaceutical composition may be heated in the presence of a base, including, by non-limiting example, NaOH. In yet another embodiment, the pharmaceutical composition is heated to a temperature of about 110° C. for at least 15 minutes in the presence of NaOH.

In some embodiments, the disclosure provides for a radiopharmaceutical composition with a micro dose of $^{225}$Ac-PSMA I&T solution and at least metal ion chelator. A suitable chelating agent may include ethylenediamine tetraacetic acid (EDTA) and its salts, N-(hydroxy-ethyl)ethylenediaminetriacetic acid, nitrilotriacetic acid (NIA), ethylene-bis(oxyethylene-nitrilo)tetraacetic acid, 1,4,7,10-tetraazacyclodo-decane-N,N',N",N'"-tetraacetic acid, 1,4,7,10-tetraaza-cyclododecane-N,N',N"-triacetic acid, 1,4,7-tris (carboxymethyl)-10-(2'-hydroxypropyl)-1,4,7,10-tetraazocyclodecane, 1,4,7-triazacyclonane-N,N',N"-triacetic acid, 1,4,8,11-tetraazacyclotetra-decane-N,N',N", N'"-tetraacetic acid; diethylenetriamine-pentaacetic acid (DTPA), ethylenedicysteine, bis(aminoethanethiol) carboxylic acid, triethylenetetraamine-hexaacetic acid, and 1,2-diaminocyclohexane-N,N,N',N'-tetraacetic acid. In one embodiment, the chelating agent may be the sodium salt of EDTA. The amount of chelating agent present in the radiopharmaceutical composition may range from about 5 μg to 50 μg. In some embodiments, the amount of chelating agent present may be about 5 μg, 6 μg, 7 μg, 8 μg, 9 μg, 10 μg, 11 μg, 12 μg, 13 μg, 14 μg, 15 μg, 16 μg, 17 μg, 18 μg, 19 μg, 20 μg, 21 μg, 22 μg, 23 μg, 24 μg, 25 μg, 26 μg, 27 μg, 28 μg, 29 μg, 30 μg, 31 μg, 32 μg, 33 μg, 34 μg, 35 μg, 40 μg, 45 μg, or 50 μg. In another embodiment, the amount of chelating agent present may be from about 0.0001% to about 0.0020% (w/w) of such radiopharmaceutical composition. In some embodiments, the amount of chelating agent present in a radiopharmaceutical composition may be about 0.0001%, 0.0002%, 0.0003%, 0.0004%, 0.0005%, 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, or 0.0015% (w/w) of the total weight of the radiopharmaceutical composition. In another embodiment, the amount of chelating agent present in the radiopharmaceutical composition may range from about 5 μg/ml to about 70 μg/ml. In some embodiments, the amount of chelating agent present in a radiopharmaceutical composition may range from about 10 μg/ml to about 70 μg/ml, 15 μg/ml to about 70 μg/ml, or about 20 μg/ml to about 70 μg/ml. In other embodiments the amount of chelating agent present in the radiopharmaceutical composition may be at least 5 g/ml, at least 10 μg/ml, at least 15 μg/ml, or at least 20 μg/ml. In some embodiments, no chelating agent is present in the radiopharmaceutical composition (e.g., the composition is free of chelating agent or there is a complete absence of chelating agent).

In some embodiments, it is beneficial for the total Fe, Cu, Zn, and/or Pb metal content of the radiopharmaceutical composition to be ≤0.05 μg/GBq, ≤0.03 μg/GBq, ≤0.01 μg/GBq, or below the detectable limit.

One aspect of the disclosure provides for a radiopharmaceutical composition with a pH of about 1 to 13, 2 to 10, 3 to 9, 4 to 9, 5 to 9, 3 to 8, 4 to 8, 5 to 8, 5 to 7.5, 5 to 7, 5 to 6, 5 to 5.5, 5.5 to 7, 3.5 to 8, 3.5 to 7.5, 3.5 to 7, 3.5 to 6, 3.5 to 5.5, 3.5 to 5, or 3.5 to 4.5. The pH of the radiopharmaceutical composition may be about 4, 4.5, 4.6. 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2. 7.3, 7.4. 7.5, 7.6. 7.7, 7.8, 7.9, 8.0, 8.1, 8.2, 8.3, 8.4, 8.5, or 9. As an example, the pH of the radiopharmaceutical composition may be about 5.5 to about 7.5.

Another aspect of the disclosure provides for a radioactive content of about 70% to 130%. The radioactive content of the radiopharmaceutical composition may be about 70% to 125%, 70% to 120%, 70% to 115%, 70% to 110%, 80% to 130%, 85% to 130%, 90% to 130%, 95% to 130%, 75% to 125%, 75% to 120%, 75% to 115%, 75% to 110%, 80% to 125%, 80% to 120%, 80% to 115%, 80% to 110%, 85% to 125%, 85% to 120%, 85% to 115%, 85% to 110%, 90% to 125%, 90% to 120%, 90% to 115%, or 90% to 110%.

Another aspect of the disclosure provides for a radioactive purity of the compositions disclosed herein at the time of production of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100%. The radiopharmaceutical compositions disclosed herein can be stored at temperatures of about 5° C. to about 40° C.

Another aspect of the disclosure provides for a radioactive purity of the radiopharmaceutical compositions disclosed herein at 48 hours after production of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100%.

Another aspect of the disclosure provides for a radioactive purity of the compositions disclosed herein at 72 hours after production of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100%.

Another aspect of the disclosure provides for a radioactive purity of the compositions disclosed herein at 96 hours after production of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100%.

Another aspect of the disclosure provides for a radioactive purity of the compositions disclosed herein at 120 hours after production of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100%.

Another aspect of the disclosure provides for a radiochemical purity of the compositions disclosed herein of 95% or greater for at least 72 hours after formulation, at least 84 hours after formulation, at least 96 hours after formulation, at least 108 hours after formulation, or at least 120 hours after formulation when stored at about 5° C. to about 40° C.

Another aspect of the disclosure provides for a radiochemical purity of the compositions disclosed herein of 97.5% or greater for at least 72 hours after formulation, at least 84 hours after formulation, at least 96 hours after formulation, at least 108 hours after formulation, or at least 120 hours after formulation when stored at about 5° C. to about 40° C.

Another aspect of the disclosure provides for a radiochemical purity of the compositions disclosed herein of 98% or greater for at least 72 hours after formulation, at least 84 hours after formulation, at least 96 hours after formulation, at least 108 hours after formulation, or at least 120 hours after formulation when stored at about 5° C. to about 40° C.

Another aspect of the disclosure provides for a radiochemical purity of the compositions disclosed herein of 99% or greater for at least 72 hours after formulation, at least 84 hours after formulation, at least 96 hours after formulation, at least 108 hours after formulation, or at least 120 hours after formulation when stored at about 5° C. to about 40° C.

The synthesis of the radiopharmaceutical composition may include a one-step labeling process with injection grade water or combination of injection grade ethanol and water used as the only solvents; therefore, no other residual solvents are present. Radiochemical impurities are quantified by chromatographical methods (TLC/HPLC). Radiochemical purity of the radiopharmaceutical composition may not be less than 95.0% in total. Chemical impurities are quantified by chromatographical methods (HPLC).

$^{225}$Ac-PSMA I&T is a relatively short-lived radiolabelled substance from which the product is formulated immediately after finished synthesis. Therefore, there are no specifications or batch analysis results for the labelled drug substance. Controls are performed on the labelled drug product.

A precursor standard manufactured by piCHEM Forschungs-und Entwicklungs GmbH (piCHEM) is used for quantification of the unlabelled/unreacted PSMA I&T precursor and non-radioactive metal chelates of PSMA I&T. The UV-absorption of metal chelates of PSMA I&T is very similar to that of the unlabelled precursor at the UV-wavelength used (280 nm) and is therefore considered suitable for quantification of trace amounts of metal chelates of PSMA I&T that may be co-produced during the heated complexation reaction of $^{225}$Ac and PSMA I&T.

A stable reference standard for $^{nat}$Lu-PSMA I&T manufactured by piCHEM is used for verifying HPLC system suitability prior to $^{225}$Ac-PSMA I&T sample analysis.

The formulation solution is prepared from an injection grade solution containing ascorbic acid (Ascor L) or sodium ascorbate and injection grade water.

Specifications for the $^{225}$Ac-PSMA I&T injection drug product are presented in Table 3a below. The specifications listed are used as release parameters except for radionuclidic purity and sterility which are tested post-release.

TABLE 3a

Specifications for $^{225}$Ac-PSMA I&T injection

| Test | Analytical Method | Acceptance Requirements |
|---|---|---|
| Appearance | Visual Inspection | Clear and colorless to yellow solution; no visible particles |
| pH | pH indicator paper | 5.5-7.0 |
| Ascorbic Acid | Strip test | 5-15 mg/ml |
| Radionuclidic Identification[¥] | Gamma Spectrometry (HPGe) | Energy from $^{225}$Ac daughter nuclide main peaks: $^{221}$Fr: 218.19 ± 4.36 keV (±2%, HPGe) $^{213}$Bi: 440.46 ± 8.81 keV (±2%, HPGe) |
| Radiochemical Identity | HPLC | The highest amount of radioactivity elutes in the same fraction with $^{nat}$Lu-PSMA I&T and PSMA I&T. The sample run is fractionated into at least four fractions of equal size. |
| Chemical Purity | HPLC | Sum of PSMA I&T and Metal-PSMA I&T complexes ≤7.5 μg/ml |
| Radiochemical Purity by HPLC Method | HPLC | ≥95.0% $^{225}$Ac-PSMA I&T |
| Radiochemical Purity by TLC Method | TLC | ≥95.0% $^{225}$Ac-PSMA I&T |
| $^{225}$Ac-PSMA I&T Specific Activity | Calculated from sum of PSMA I&T and M-PSMA I&T mass concentration and radioactivity concentration | Reported (no specification set) |
| Radionuclidic Purity** | Gamma spectrometry (HPGe) | ≥99.9% of the total activity of $^{225}$Ac at the end of the production |
| Endotoxin | Endotoxin Test | <175 EU/20 ml vial* (≤8.75 EU/ml) |
| Sterile Filter Integrity | Bubble Point Test | ≥3.32 bar (Pall, Mini Kleenpak) |
| Radioactivity Content | Gamma spectrometry (HPGe) | 90-110% at the date and time stated on the label |
| Sterility | Sterility Test | Sterile |

*Maximum volume to be administered per dose is defined as 20 ml.

† The sterility test samples are initiated post-release.

**This test is performed post-release due to the length of time required to perform the test.

¥Test is performed after sufficient decay-time to attain equilibrium between the daughter radionuclides.

In some alternative embodiments, the Sum of PSMA I&T and Metal-PSMA I&T complexes may be ≤7.5 µg/ml, ≤7.4 µg/ml, ≤7.3 µg/ml, ≤7.2 µg/ml, ≤7.1 µg/ml, ≤7.0 µg/ml, ≤6.9 µg/ml, ≤6.8 µg/ml, ≤6.7 µg/ml, ≤6.6 µg/ml, ≤6.5 µg/ml, ≤6.4 µg/ml, ≤6.3 µg/ml, ≤6.2 µg/ml, ≤6.1 µg/ml, ≤6.0 µg/ml, ≤5.9 µg/ml, ≤5.8 µg/ml, ≤5.7 µg/ml, ≤5.6 µg/ml, ≤5.5 µg/ml, ≤5.4 µg/ml, ≤5.3 µg/ml, ≤5.2 µg/ml, ≤5.1 µg/ml, ≤5.0 µg/ml, ≤4.9 µg/ml, ≤4.8 µg/ml, ≤4.7 µg/ml, ≤4.6 µg/ml, ≤4.5 µg/ml, ≤4.4 µg/ml, ≤4.3 µg/ml, ≤4.2 µg/ml, ≤4.1 µg/ml, ≤4.0 µg/ml, ≤3.9 µg/ml, ≤3.8 µg/ml, ≤3.7 µg/ml, ≤3.6 µg/ml, ≤3.5 µg/ml, ≤3.4 µg/ml, ≤3.3 µg/ml, ≤3.2 µg/ml, <3.1 µg/ml, <3.0 µg/ml, ≤2.9 µg/ml, ≤2.8 µg/ml, ≤2.7 µg/ml, ≤2.6 µg/ml, ≤2.5 µg/ml, ≤2.4 µg/ml, ≤2.3 µg/ml, ≤2.2 µg/ml, ≤2.1 µg/ml, or ≤2.0 µg/ml.

In some alternative embodiments, the endotoxin content is ≤175 EU/20 ml vial, ≤150 EU/20 ml vial, ≤125 EU/20 ml vial, ≤100 EU/20 ml vial, ≤75 EU/20 ml vial, ≤50 EU/20 ml vial, or ≤25 EU/20 ml vial.

In some alternative embodiments, the total stabilizer content may be ≤50.0% (v/v), ≤30.0% (v/v), ≤20.0% (v/v), ≤15.0% (v/v), ≤10.0% (v/v), ≤7.5% (v/v), ≤7.4% (v/v), ≤7.3% (v/v), ≤7.2% (v/v), ≤7.1% (v/v), ≤7.0% (v/v), ≤6.9% (v/v), ≤6.8% (v/v), ≤6.7% (v/v), ≤6.6% (v/v), ≤6.5% (v/v), ≤6.4% (v/v), ≤6.3% (v/v), ≤6.2% (v/v), ≤6.1% (v/v), ≤6.0% (v/v), ≤5.9% (v/v), ≤5.8% (v/v), ≤5.7% (v/v), ≤5.6% (v/v), ≤5.5% (v/v), ≤5.4% (v/v), ≤5.3% (v/v), ≤5.2% (v/v), ≤5.1% (v/v), ≤5.0% (v/v), ≤4.9% (v/v), ≤4.8% (v/v), ≤4.7% (v/v), ≤4.6% (v/v), ≤4.5% (v/v), ≤4.4% (v/v), ≤4.3% (v/v), ≤4.2% (v/v), ≤4.1% (v/v), ≤4.0% (v/v), ≤3.9% (v/v), ≤3.8% (v/v), ≤3.7% (v/v), ≤3.6% (v/v), ≤3.5% (v/v), ≤3.4% (v/v), ≤3.3% (v/v), ≤3.2% (v/v), ≤3.1% (v/v), ≤3.0% (v/v), ≤2.9% (v/v), ≤2.8% (v/v), ≤2.7% (v/v), ≤2.6% (v/v), ≤2.5% (v/v), ≤2.4% (v/v), ≤2.3% (v/v), ≤2.2% (v/v), ≤2.1% (v/v), ≤2.0% (v/v), ≤1.9% (v/v), ≤1.8% (v/v), ≤1.7% (v/v), ≤1.6% (v/v), ≤1.5% (v/v), ≤1.4% (v/v), ≤1.3% (v/v), ≤1.2% (v/v), ≤1.1% (v/v), ≤1.0% (v/v), ≤0.9% (v/v), ≤0.8% (v/v), ≤0.7% (v/v), ≤0.6% (v/v), ≤0.5% (v/v), ≤0.4% (v/v), ≤0.3% (v/v), ≤0.2% (v/v), ≤0.1% (v/v), or 0.0% (v/v).

In some alternative embodiments, the ethanol content may be ≤30.0% (v/v), ≤20.0% (v/v), ≤15.0% (v/v), ≤10.0% (v/v), ≤7.5% (v/v), ≤7.4% (v/v), ≤7.3% (v/v), ≤7.2% (v/v), ≤7.1% (v/v), ≤7.0% (v/v), ≤6.9% (v/v), ≤6.8% (v/v), ≤6.7% (v/v), ≤6.6% (v/v), ≤6.5% (v/v), ≤6.4% (v/v), ≤6.3% (v/v), ≤6.2% (v/v), ≤6.1% (v/v), ≤6.0% (v/v), ≤5.9% (v/v), ≤5.8% (v/v), ≤5.7% (v/v), ≤5.6% (v/v), ≤5.5% (v/v), ≤5.4% (v/v), ≤5.3% (v/v), ≤5.2% (v/v), ≤5.1% (v/v), ≤5.0% (v/v), ≤4.9% (v/v), ≤4.8% (v/v), ≤4.7% (v/v), ≤4.6% (v/v), ≤4.5% (v/v), ≤4.4% (v/v), ≤4.3% (v/v), ≤4.2% (v/v), ≤4.1% (v/v), ≤4.0% (v/v), ≤3.9% (v/v), ≤3.8% (v/v), ≤3.7% (v/v), ≤3.6% (v/v), ≤3.5% (v/v), ≤3.4% (v/v), ≤3.3% (v/v), ≤3.2% (v/v), ≤3.1% (v/v), ≤3.0% (v/v), ≤2.9% (v/v), ≤2.8% (v/v), ≤2.7% (v/v), ≤2.6% (v/v), ≤2.5% (v/v), ≤2.4% (v/v), ≤2.3% (v/v), ≤2.2% (v/v), ≤2.1% (v/v), ≤2.0% (v/v), ≤1.9% (v/v), ≤1.8% (v/v), ≤1.7% (v/v), ≤1.6% (v/v), ≤1.5% (v/v), ≤1.4% (v/v), ≤1.3% (v/v), ≤1.2% (v/v), ≤1.1% (v/v), ≤1.0% (v/v), ≤0.9% (v/v), ≤0.8% (v/v), ≤0.7% (v/v), ≤0.6% (v/v), ≤0.5% (v/v), ≤0.4% (v/v), ≤0.3% (v/v), ≤0.2% (v/v), ≤0.1% (v/v), or 0.0% (v/v).

In some alternative embodiments, the gentisic acid content may be ≤30.0% (v/v), ≤20.0% (v/v), ≤15.0% (v/v), ≤10.0% (v/v), ≤7.5% (v/v), ≤7.4% (v/v), ≤7.3% (v/v), ≤7.2% (v/v), ≤7.1% (v/v), ≤7.0% (v/v), ≤6.9% (v/v), ≤6.8% (v/v), ≤6.7% (v/v), ≤6.6% (v/v), ≤6.5% (v/v), ≤6.4% (v/v), ≤6.3% (v/v), ≤6.2% (v/v), ≤6.1% (v/v), ≤6.0% (v/v), ≤5.9% (v/v), ≤5.8% (v/v), ≤5.7% (v/v), ≤5.6% (v/v), ≤5.5% (v/v), ≤5.4% (v/v), ≤5.3% (v/v), ≤5.2% (v/v), ≤5.1% (v/v), ≤5.0% (v/v), ≤4.9% (v/v), ≤4.8% (v/v), ≤4.7% (v/v), ≤4.6% (v/v), ≤4.5% (v/v), ≤4.4% (v/v), ≤4.3% (v/v), ≤4.2% (v/v), ≤4.1% (v/v), ≤4.0% (v/v), ≤3.9% (v/v), ≤3.8% (v/v), ≤3.7% (v/v), ≤3.6% (v/v), ≤3.5% (v/v), ≤3.4% (v/v), ≤3.3% (v/v), ≤3.2% (v/v), ≤3.1% (v/v), ≤3.0% (v/v), ≤2.9% (v/v), ≤2.8% (v/v), ≤2.7% (v/v), ≤2.6% (v/v), ≤2.5% (v/v), ≤2.4% (v/v), ≤2.3% (v/v), ≤2.2% (v/v), ≤2.1% (v/v), ≤2.0% (v/v), ≤1.9% (v/v), ≤1.8% (v/v), ≤1.7% (v/v), ≤1.6% (v/v), ≤1.5% (v/v), ≤1.4% (v/v), ≤1.3% (v/v), ≤1.2% (v/v), ≤1.1% (v/v), ≤1.0% (v/v), ≤0.9% (v/v), ≤0.8% (v/v), ≤0.7% (v/v), ≤0.6% (v/v), ≤0.5% (v/v), ≤0.4% (v/v), ≤0.3% (v/v), ≤0.2% (v/v), ≤0.1% (v/v), or 0.0% (v/v).

In some embodiments, the RBE of the $^{225}$Ac present in the radiopharmaceutical composition is ≥4.2, ≥4.3, ≥4.4, ≥4.5, ≥4.6, ≥4.7, ≥4.8, ≥4.9, ≥5.0, ≥5.1, ≥5.2, ≥5.3, ≥5.4, ≥5.5, ≥5.6, ≥5.7, ≥5.8, ≥5.9, or ≥6.0 compared to $^{177}$Lu. In yet another embodiment, the relative biological effectiveness (RBE) of the $^{225}$Ac present in the radiopharmaceutical composition is around 5.0 compared to $^{177}$Lu. This results in a much lower radioactivity used for $^{225}$Ac-PSMA I&T compared to that used for $^{177}$Lu-PSMA I&T. While this lower radioactivity may make post-therapeutic SPECT imaging difficult, the $^{225}$Ac daughter nuclides $^{221}$Fr and $^{213}$Bi produce sufficient gamma emission to enable such imaging. Calculation of RBE is discussed within "In vitro dose effect relationships of actinium-225- and lutetium-177-labelled PSMA-I&T," (Ruigrok 2022 et al.) which is incorporated by reference in its entirety. In vitro data presented in Ruigrok 2022 et al. demonstrates the similar binding characteristics and uptake between $^{225}$Ac-PSMA I&T and $^{177}$Lu-PSMA I&T, allowing for the total mass amount of the PSMA I&T per dose of the radiopharmaceutical composition to be adjusted such that it is the same as is used with $^{177}$Lu. A comparison of the characteristics of $^{177}$Lu-PSMA I&T and $^{225}$Ac-PSMA I&T is found in Table 3b below.

TABLE 3b

| CHARACTERISTICS (PER DOSE) | $^{177}$Lu-PSMA I&T | $^{225}$Ac-PSMA I&T | NOTES |
|---|---|---|---|
| Radioactivity | 7400 MBq (200 mCi) | 8 MBq (0.216 mCi) | Relative biological effectiveness (RBE) of around 5 is assumed for $^{225}$Ac compared to $^{177}$Lu. This results in much lower (~8 MBq) activity used for $^{225}$Ac-PSMA I&T compared to the 7400 MBq for $^{177}$Lu-PSMA I&T. Low activity makes post-therapeutic SPECT imaging difficult, although $^{225}$Ac daughter nuclides $^{221}$Fr and $^{213}$Bi have sufficient gamma emission. |
| No. of Atoms | 10.3 nmol | 0.0166 nmol | No. of atoms (in nmol) is determined from the radioactivity. |
| Total PSMA I&T content | ~80 µg | ~80 µg | Total amount of PSMA I&T and M-PSMA I&T compounds in the finished dose. PSMA content in $^{225}$Ac-PSMA I&T |

TABLE 3b-continued

| CHARACTERISTICS (PER DOSE) | $^{177}$Lu-PSMA I&T | $^{225}$Ac-PSMA I&T | NOTES |
|---|---|---|---|
| | | | formulation is adjusted to match $^{177}$Lu-PSMA I&T formulation (~5 μg/ml or ~80 μg per dose) |
| No. of molecules of PSMA I&T | 53.4 nmol | 53.4 nmol | PSMA I&T molecular weight used in the calculation 1498 g/mol. |
| Ratio of PSMA I&T to $^{177}$Lu or $^{225}$Ac atoms | 5.2:1 | 3225:1 | Due to the much lower activity of $^{225}$Ac, the molar ratio is a whole different order of magnitude. |

The total mass of the PSMA I&T present within the radiopharmaceutical composition may be 95 μg/dose±15%, ±10%, or ±5%, 90 μg/dose±15%, ±10%, or ±5%, 85 μg/dose±15%, ±10%, or ±5%, 80 μg/dose±15%, ±10%, or ±5%, 75 μg/dose±15%, ±10%, or ±5%, 70 μg/dose±15%, ±10%, or ±5%, 60 μg/dose±15%, ±10%, or ±5%, 55 μg/dose±15%, ±10%, or ±5%, 50 μg/dose±15%, ±10%, or ±5%, 45 μg/dose±15%, ±10%, or ±5%, or 40 μg/dose±15%, ±10%. The total mass of the PSMA I&T and M-PSMA I&T, where M stands for any metal such as Zn, Ni, Pb or Cu and includes $^{225}$Ac, present within the radiopharmaceutical composition may also be 95 μg/dose±15%, ±10%, or ±5%, 90 μg/dose±15%, ±10%, or ±5%, 85 μg/dose±15%, ±10%, or ±5%, 80 μg/dose±15%, ±10%, or ±5%, 75 μg/dose±15%, ±10%, or ±5%, 70 μg/dose±15%, ±10%, or ±5%, 60 μg/dose±15%, ±10%, or ±5%, 55 μg/dose±15%, ±10%, or ±5%, 50 μg/dose±15%, ±10%, or ±5%, 45 μg/dose±15%, ±10%, or ±5%, or 40 μg/dose±15%, ±10%. In another embodiment, the total mass of PSMA I&T and M-PSMA I&T present within the radiopharmaceutical composition may be about 80 μg/dose.

The administered dose of the radiopharmaceutical composition may vary since the radioactivity delivered to the human patient via the radiopharmaceutical composition depends on both the dosage volume and the quantity of activity given in the treatment dose. Generally, the lower the radioactivity concentration (RAC) in the dose, the higher the stability of the product. Accordingly, in one embodiment, the administered dose of radiopharmaceutical composition may range from about 10 ml to about 50 ml. In various embodiments, the administered dose of radiopharmaceutical composition may range from about 10 ml to about 20 ml, about 10 ml to about 30 ml, about 10 ml to about 40 ml, about 20 ml, to about 30 ml, about 20 ml to about 40 ml, about 20 ml to about 50 ml or about 25 ml to about 26 ml.

In some embodiments of the presently disclosed radiopharmaceutical composition, PSMA I&T may be present in an amount ranging from about 2 μg/ml to about 12 μg/ml PSMA I&T, about 4 μg/ml to about 12 μg/ml PSMA I&T, about 6 μg/ml to about 12 μg/ml PSMA I&T, about 4 μg/ml to about 6 μg/ml PSMA I&T, about 8 μg/ml PSMA I&T to about 12 μg/ml PSMA I&T, or about 10 μg/ml to about 12 μg/ml PSMA I&T. In another embodiment, the radiopharmaceutical composition may have a PSMA I&T content of about 5 μg/ml.

Due to the higher RBE of $^{225}$Ac compared to $^{177}$Lu, $^{225}$Ac-PSMA I&T may be present within the composition in an amount of 8.0±25% MBq, 8.0±20% MBq, 8.0±15% MBq, 8.0±10% MBq, or 8.0±5% MBq. In other embodiments the $^{225}$Ac-PSMA I&T may be present within the composition in an amount of 0.395 MBq/ml±25%, 0.495 MBq/ml±25%, 0.595 MBq/ml±25% of 0.695 MBq/ml±25%, 0.795 MBq/ml±25%, 0.895 MBq/ml±25%, 0.995 MBq/ml±25%, 1.095 MBq/ml±25%, 1.195 MBq/ml±25%, 1.295 MBq/ml±25%, 1.395 MBq/ml±25%, or 1.495 MBq/ml±25%. In further embodiments, the $^{225}$Ac-PSMA I&T may be present within the composition in an amount of 0.216±25% mCi, 0.216±20% mCi, 0.216±15% mCi, 0.216±10% mCi, or 0.216±5% mCi.

The molar ratio of PSMA I&T to $^{225}$Ac within the presently disclosed radiopharmaceutical composition may be adjusted to account for the higher RBE of $^{225}$Ac compared to $^{177}$Lu. Due to higher RBE of $^{225}$Ac, lower activity is recommended for RLT using $^{225}$Ac compared to $^{177}$Lu. Lower activity means fewer atoms are undergoing radioactive decay per unit time, and because molar amount is directly proportional to the number of atoms, a lower activity corresponds to a smaller molar amount of radioactive isotope. In comparison—a therapeutic dose of $^{177}$Lu-PSMA I&T may be 7400 MBq which corresponds to around 10.3 nmol of $^{177}$Lu isotope. Similarly, a therapeutic dose of $^{225}$Ac-PSMA I&T may be 8 MBq which corresponds to 0.0166 nmol of $^{225}$Ac, as shown in Table 3b above. It means that the molar amount of $^{225}$Ac-PSMA I&T is only 0.16% of the amount of $^{177}$Lu-PSMA I&T in a dose.

The molar ratio of PSMA I&T to $^{177}$Lu or $^{225}$Ac considers the proportion of all PSMA I&T molecules in a dose to the amount of radioisotope. In addition to the radiolabelled form, a dose may contain PSMA I&T in other forms such as unlabelled PSMA I&T and M-PSMA I&T which are included in the ratio. The trace amount of metal contaminants present in the raw materials used to manufacture the drug substance are quantitatively well in excess of $^{225}$Ac. Therefore, for $^{225}$Ac, adjusting the total amount of PSMA I&T to match the ratio of PSMA I&T to $^{177}$Lu is not feasible and consequently, the molar ratio of PSMA I&T to $^{225}$Ac is adjusted.

In some embodiments, the molar ratio of PSMA I&T to $^{225}$Ac may be ≥1,000:1.0, ≥2,000:1.0, ≥3,000:1.0, or ≥4,000:1.0 in a dose of the radiopharmaceutical composition. In some embodiments, the molar ratio of PSMA I&T to $^{225}$Ac may range from 1,000:1.0 to 5,000:1.0, 2,000:1.0 to 4,000:1.0, 2,500:1.0 to 3,500:1.0, 3,000:1.0 to 3,500:1.0, 3,050:1.0 to 3,450:1.0, 3,100:1.0 to 3,400:1.0, 3,150:1.0 to 3,350:1.0, or 3,200:1.0 to 3,300:1.0. In some embodiments, the molar ratio of PSMA I&T to $^{225}$Ac may be 3,225:1.0±25%, 3,225:1.0±20%, 3,225:1.0±15%, 3,225:1.0±10%, or 3,225:1.0±5%. In yet another embodiment, the molar ratio of PSMA I&T to $^{225}$Ac may be about 3225:1.0 in a dose of the radiopharmaceutical composition.

In another embodiment, the radiopharmaceutical composition may have a specific activity of 0.112 MBq/nmol±0.025 MBq/nmol, 0.112 MBq/nmol=0.020 MBq/nmol, 0.112 MBq/nmol±0.015 MBq/nmol, 0.112 MBq/nmol±0.010 MBq/nmol, or 0.112 MBq/nmol±0.005 MBq/nmol.

In another embodiment, $^{177}$Lu-PSMA I&T may potentially be used in place of $^{225}$Ac-PSMA I&T according to $^{177}$Lu-PSMA I&T dosimetry to determine the distribution of $^{225}$Ac-PSMA I&T in a patient (e.g., human patient).

One aspect of the present disclosure provides for the administration of the radiopharmaceutical composition to a human in need thereof. Accordingly, the composition may be formulated to be suitable for human administration. In some embodiments, the radiopharmaceutical composition is suitable for human administration for 1, 3, 5, 6, 7, 9, 10, 12, 14, 15, 20, 21, 25, 28, 30, 35, or 40 or more cycles of treatment. In another embodiment, the radiopharmaceutical composition is suitable for human administration for 1 to about 6 cycles of treatment.

In some embodiments, the radiopharmaceutical composition may be part of a radiopharmaceutical kit suitable for administration to a human in need thereof.

The administration of $^{225}$Ac-PSMA I&T may be described as a mathematical formula to ensure that the total cumulative dose to the patient's kidneys after all treatments remains below 7 Gy, below 6.9 Gy, below 6.8 Gy, below 6.7 Gy, below 6.6 Gy, below 6.5 Gy, below 6.4 Gy, below 6.3 Gy, below 6.2 Gy, below 6.2 Gy, below 6.1 Gy, below 6 Gy, below 5.9 Gy, below 5.8 Gy, below 5.7 Gy, below 5.6 Gy, below 5.5 Gy, below 5.4 Gy, below 5.3 Gy, below 5.2 Gy, below 5.2 Gy, below 5.1 Gy, below 5 Gy, below 4.9 Gy, below 4.8 Gy, below 4.7 Gy, below 4.6 Gy, or below 4.5 Gy. An example formula is shown below to determine the number of cycles allowable (using 7 Gy).

$$X = \frac{7}{Y * Z} \qquad \text{Eq. 1}$$

where X is the total number of cycles allowable at a given activity of $^{225}$Ac-PSMA I&T, Y is the activity of each dose of the $^{225}$Ac-PSMA I&T, Y is the absorbed dose of radiation in Gy per GBq of the administered $^{225}$Ac-PSMA I&T, and Z is the activity of the of the administered $^{225}$Ac-PSMA I&T in GBq.

In various embodiments, the present disclosure is related to a radiopharmaceutical kit, comprising a vial containing at least a single dose of a $^{255}$Ac-PSMA I&T solution for injection to a human patient in need thereof, wherein $^{255}$Ac-PSMA I&T treatment with 1, 2, 3, 4, 5, 6, or 7 cycles at the dose is possible without the risk of kidney toxicities and/or wherein $^{255}$Ac-PSMA I&T treatment with 1, 2, 3, 4, 5, 6, or 7 cycles provides a mean projected dose that is below a cumulative absorbed dose to the kidney of 7 Gy, below 6.9 Gy, below 6.8 Gy, below 6.7 Gy, below 6.6 Gy, below 6.5 Gy, below 6.4 Gy, below 6.3 Gy, below 6.2 Gy, below 6.2 Gy, below 6.1 Gy, below 6 Gy, below 5.9 Gy, below 5.8 Gy, below 5.7 Gy, below 5.6 Gy, below 5.5 Gy, below 5.4 Gy, below 5.3 Gy, below 5.2 Gy, below 5.2 Gy, below 5.1 Gy, below 5 Gy, below 4.9 Gy, below 4.8 Gy, below 4.7 Gy, below 4.6 Gy, or below 4.5 Gy and/or the projected or actual cumulative absorbed dose to the kidneys at 1, 2, 3, 4, 5, 6, or 7 cycles is less than 7 Gy, 6.9 Gy, 6.8 Gy, 6.7 Gy, 6.6 Gy, 6.5 Gy, 6.4 Gy, 6.3 Gy, 6.2 Gy, 6.2 Gy, 6.1 Gy, 6 Gy, 5.9 Gy, 5.8 Gy, 5.7 Gy, 5.6 Gy, 5.5 Gy, 5.4 Gy, 5.3 Gy, 5.2 Gy, 5.2 Gy, 5.1 Gy, 5 Gy, 4.9 Gy, 4.8 Gy, 4.7 Gy, 4.6 Gy, or 4.5 Gy and no renal toxicities are observed. The vials may comprise 0.1-0.5 mL, 0.5-1 mL, 1-5 mL, 5-10 mL, 5-15 mL, 5-20 mL, 5-50 mL, 5-100 mL, 10-15 mL, 10-20 mL, 10-50 mL, 10-100 mL, 15-20 mL, 15-50 mL, 15-100 mL, 20-50 mL, 20-100, mL, or 50-100 mL of solution (e.g., aqueous solution).

The present disclosure further provides for a method of administration of the presently disclosed radiopharmaceutical composition. In one embodiment, the method includes the determination of a total absorbed radiation dose via SPECT imaging, planar imaging, or a combination of the two. Other imaging methods may also be suitable for determining the total absorbed radiation dose.

a. Analytical Procedures

The product is identified by subsequent injection of reference solution of Lu-PSMA I&T and PSMA I&T, and formulated solution to a liquid chromatography system.

Radio nuclidic identity is determined by gamma ray energy detection.

pH is estimated by pH paper.

Ascorbic acid content is determined using test strips.

Radioactivity is measured in a HPGe gamma spectrometer.

Radiochemical and chemical purity is determined by liquid chromatography with a fraction collector and thin layer chromatography both combined with HPGe gamma spectrometer measurement.

The amount of $^{225}$Ac-PSMA I&T in the dose is calculated from the radioactivity measurement.

Bacterial endotoxin content is determined for each batch before release.

Sterility is determined by means of post release sterility testing.

The analytical procedures used for the drug product—e.g., specificity, linearity, and reproducibility—were investigated by using a known amount of reference standards for the un-labelled precursor. All analytical procedures were found suitable for their intended use.

An acceptance criterion for the amount of radioactivity in the formulation is not set since this will vary depending on the individual clinical need assessed by the health care professional responsible for administering the formulation. The radioactive content must be within 90%-110% of the stated value at the date and time stated on the label.

b. Stability Data for the Radiopharmaceutical Composition

The radiopharmaceutical composition is immediately formulated as a step in the automated synthesis process.

The radiochemical purity and chemical properties of the formulated radiopharmaceutical composition (pH, impurities, visual properties) were tested on at least three batches over a time span of 48 hours or 120 hours from the end-of-synthesis time. Stability samples of minimum and maximum dose volume (10 ml-20 ml) were stored inverted in a container closer system specific for the $^{225}$Ac-PSMA I&T injection at different temperature conditions.

Stability study data for an embodiment stable at 48 hours for the prepared radiopharmaceutical composition is provided in Table 4.

Stability study data for an embodiment stable at 120 hours for the prepared radiopharmaceutical composition is provided in Tables 5a, 5b and 5c.

All stability samples for the embodiment stable at 120 hours met the pre-determined acceptance criteria. Radiochemical purities were well above the specifications of ≥95.0% in all the samples analysed after 120 hours of storage. Based on the obtained stability results, the $^{225}$Ac-PSMA I&T injection was not found to be sensitive to storage conditions tested at temperatures of 5° C.±3° C., 22.5° C.±2° C., 32.5° C.±2° C., 40° C.±2° C.

Based on these results a shelf life of 120 hours is considered justified.

TABLE 4

Stability Data (embodiment stable at 48 hours): Chemical quality at 48 h post end of synthesis

| Stability criteria | | | Stability data at 48 h after end of synthesis | | |
|---|---|---|---|---|---|
| Test | Specification | ACMI21148-1 | ACM12115D-1, +5° C. | ACMI2115D-1, +22.5° C. | ACMI2115D-1, +40° C. |
| Visual inspection | Clear, colorless or slightly yellow liquid, no visible particles | Pass | Pass | Pass | Pass |
| pH | 5.0-8.0 | 5.5 | 6.0 | 5.0 | 5.0 |
| $^{221}$Fr and $^{213}$Bi main peak gammaenergy | $^{221}$Fr: 218 ± 2 keV $^{213}$Bi: 440 ± 4 kev (HPGe-detecter) | $^{221}$Fr: 218 keV $^{213}$Bi: 441 keV | $^{221}$Fr: 218 keV $^{213}$Bi: 441 keV | $^{221}$Fr: 218 keV $^{213}$Bi: 441 keV | $^{221}$Fr: 218 keV $^{213}$Bi: 441 keV |
| Radioactivity concentration (MBq/ml) | No specification set | 0.820 MBq/ml 8 Apr. 2021 10:19 | 1.000 MBq/ml 17 Apr. 2021 10:10 | 1.009 MBq/ml 17 Apr. 2021 9:51 | 0.996 MBq/ml 17 Apr. 2021 10:25 |
| Radiochemical purity % (TLC/HPGe) | $^{225}$Ac-PSMA I&T radioactivity ≥95% from total radioactivity | 96.1% | 95.2% | 94.7% | 89.6% |
| Chemical purity PSMA I&T | <12.0 μg/ml | 2.0 μg/ml | 8.1 μg/ml | 6.4 μg/mt | 6.3 μg/ml |
| Chemical purity Oder impurities | <12.0 μg/ml | 8.7 μg/ml | 6.3 μg/ml | 6.4 μg/ml | 8.4 μg/ml |
| Specific activity | No specification set | 0.115 MBq/nmol | 0.104 MBq/nmol | 0.118 MBq/nmol | 0.101 MBq/nmol |
| Ascorbic acid | 20-70 mg/ml | 30 mg/ml | 30 mg/ml | 30 mg/ml | 30 mg/ml |

| Stability criteria | | Stability data at 48 h after end of synthesis | | |
|---|---|---|---|---|
| Test | Specification | ACMI2115D-2 | ACMI2119B-1 | ACMI2119E-1 |
| Visual inspection | Clear, colorless or slightly yellow liquid, no visible particles | Pass | Pass | Pass |
| pH | 5.0-8.0 | 5.5 | 5.5 | 5.5 |
| $^{221}$Fr and $^{213}$Bi main peak gammaenergy | $^{221}$Fr: 218 ± 2 keV $^{213}$Bi: 440 ± 4 kev (HPGe-detecter) | $^{221}$Fr: 218 keV $^{213}$Bi: 441 keV | $^{221}$Fr: 218 keV $^{213}$Bi: 441 keV | $^{221}$Fr: 218 keV $^{213}$Bi: 441 keV |
| Radioactivity concentration (MBq/ml) | No specification set | 0.957 MBq/ml 17 Apr. 2021 10:38 | 0.901 MBq/ml 13 May 2021 11:15 | 0.915 MBq/ml 16 May 2021 9:19 |
| Radiochemical purity % (TLC/HPGe) | $^{225}$Ac-PSMA I&T radioactivity ≥95% from total radioactivity | 95.7% | 94.8% | 95.2% |
| Chemical purity PSMA I&T | <12.0 μg/ml | 5.6 μg/ml | 5.1 μg/ml | 4.6 μg/ml |
| Chemical purity Oder impurities | <12.0 μg/ml | 6.4 μg/ml | 7.8 μg/ml | 7.7 μg/ml |
| Specific activity | No specification set | 0.119 MBq/nmol | 0.105 MBq/nmol | 0.112 MBq/nmol |
| Ascorbic acid | 20-70 mg/ml | 50 mg/ml | 30 mg/ml | 30 mg/ml |

TABLE 5a

Stability Data (embodiment stable at 120 hours): Chemical quality at 120 h post end of synthesis

| ACMI2409C-1 | 120 h post End of Synthesis | | | |
|---|---|---|---|---|
| VIAL No. | 2 | 3 | 4 | 5 |
| Radioactivity * | 5.40 MBq at 28 Feb. 2024 | 5.23 MBq at 28 Feb. 2024 | 5.61 MBq at 28 Feb. 2024 | 10.36 MBq at 28 Feb. 2024 |
| Fill Volume | 10.00 ml | 10.00 ml | 10.00 ml | 18.05 ml |
| Storage Condition | 40° C. ± 2° C. | 32.5° C. ± 2° C. | 22.5° C. ± 2° C. | 5° C. ± 3° C. |
| Sample taken at | 4 Mar. 2024 12:44 | 4 Mar. 2024 12:24 | 4 Mar. 2024 12:12 | 4 Mar. 2024 11:56 |

QC TESTING (STABILITY CRITERIA)

| Test | Specification | Results | | | |
|---|---|---|---|---|---|
| Appearance | Clear, colorless to yellow solution, no visible particles | Pass | Pass | Pass | Pass |
| pH | 5.5-7.0 | 6.0 | 6.0 | 6.0 | 6.0 |
| Ascorbic Acid | 5-15 mg/ml | 10 mg/ml | 10 mg/ml | 10 mg/ml | 10 mg/ml |

TABLE 5a-continued

| Stability Data (embodiment stable at 120 hours): Chemical quality at 120 h post end of synthesis | | | | | |
|---|---|---|---|---|---|
| Radionuclidic Identification | Energy from $^{225}$Ac daughter nuclide main peaks: $^{221}$Fr: 218.19 ± 4.36 keV (±2%, HPGe) $^{213}$Bi: 440.46 ± 8.81 keV (±2%, HPGe) | 218 keV and 441 keV | 218 keV and 441 keV | 218 keV and 441 keV | 218 keV and 441 keV |
| Radiochemical Identity | The highest amount of radioactivity elutes in the same fraction with $^{nat}$Lu-PSMA I&T and PSMA I&T. The HPLC fraction is collected between 13-18 minutes | Pass | Pass | Pass | Pass |
| Chemical Purity | Sum of PSMA I&T and M-PSMA I&T complexes ≤7.5 μg/ml | 3.8 μg/ml | 3.9 μg/ml | 5.1 μg/ml | 4.0 μg/ml |
| Radiochemical Purity by HPLC Method | ≥95.0% $^{225}$Ac-PSMA I&T | 97.3% Data Acquired 4 Mar. 2024 14:22:46 | 97.3% Data Acquired 4 Mar. 2024 13:48:34 | 97.4% Data Acquired 4 Mar. 2024 13:09:08 | 98.1% Data Acquired 4 Mar. 2024 12:29:02 |
| Radiochemical Purity by TLC Method | ≥95.0% $^{225}$Ac-PSMA I&T | 98.6% | 99.1% | 99.1% | 99.7% |
| $^{225}$Ac-PSMA I&T Specific Activity | Reported | 0.149 MBq/nmol | 0.141 MBq/nmol | 0.118 MBq/nmol | 0.151 MBq/nmol |
| Radionuclidic Purity | ≥99.9% of the total activity of $^{225}$Ac at the end of production | N/A | N/A | N/A | N/A |
| Endotoxin | <175 EU/20 ml vial (<8.75 (EU/ml)) | N/A | N/A | N/A | N/A |
| Sterile Filter Integrity | ≥3.32 bar tested with water (Pall, Mini Kleenpak) | N/A | N/A | N/A | N/A |
| Radioactivity Content † | 90-110% at the date and time stated on the label | Pass | Pass | Pass | Pass |
| Sterility | Sterile | N/A | N/A | N/A | N/A |

TABLE 5b

| Stability Data (embodiment stable at 120 hours): Chemical quality at 120 h post end of synthesis | | | | |
|---|---|---|---|---|
| ACMI2409C-2 | 120 h post End of Synthesis | | | |
| VIAL No. | 2 | 3 | 4 | 5 |
| Radioactivity * | 5.88 MBq at 28 Feb. 2024 | 5.82 MBq at 28 Feb. 2024 | 5.64 MBq at 28 Feb. 2024 | 10.61 MBq at 28 Feb. 2024 |
| Fill Volume | 9.99 ml | 9.99 ml | 9.99 ml | 18.08 ml |
| Storage Condition | 40° C. ± 2° C. | 32.5° C. ± 2° C. | 22.5° C. ± 2° C. | 5° C. ± 3° C. |
| Sample taken at | 4 Mar. 2024 12:53 | 4 Mar. 2024 12:53 | 4 Mar. 2024 12:53 | 4 Mar. 2024 12:53 |

| QC TESTING (STABILITY CRITERIA) | | | | | |
|---|---|---|---|---|---|
| Test | Specification | Results | | | |
| Appearance | Clear, colorless to yellow solution, no visible particles | Pass | Pass | Pass | Pass |
| pH | 5.5-7.0 | 5.5 | 5.5 | 5.5 | 5.5 |
| Ascorbic Acid | 5-15 mg/ml | 10 mg/ml | 10 mg/ml | 10 mg/ml | 10 mg/ml |
| Radionuclidic Identification | Energy from $^{225}$Ac daughter nuclide main peaks: $^{221}$Fr: 218.19 ± 4.36 keV (±2%, HPGe) $^{213}$Bi: 440.46 ± 8.81 keV (±2%, HPGe) | 218 keV and 440 keV | 218 keV and 440 keV | 218 keV and 440 keV | 218 keV and 440 keV |
| Radiochemical Identity | The highest amount of radioactivity elutes in the same fraction with $^{nat}$Lu-PSMA I&T and PSMA I&T. The HPLC fraction is collected between 13-18 minutes | Pass | Pass | Pass | Pass |

TABLE 5b-continued

| Stability Data (embodiment stable at 120 hours): Chemical quality at 120 h post end of synthesis | | | | | |
|---|---|---|---|---|---|
| Chemical Purity | Sum of PSMA I&T and Metal-PSMA I&T complexes ≤7.5 μg/ml | 3.2 μg/ml | 4.1 μg/ml | 4.2 μg/ml | 3.7 μg/ml |
| Radiochemical Purity by HPLC Method | ≥95.0% $^{225}$Ac-PSMA I&T | 97.1% Data Acquired 4 Mar. 2024 15:02:42 | 97.% Data Acquired 4 Mar. 2024 15:40:54 | 97.2% Data Acquired 4 Mar. 2024 16:19:16 | 97.5% Data Acquired 4 Mar. 2024 16:53:17 |
| Radiochemical Purity by TLC Method | ≥95.0% $^{225}$Ac-PSMA I&T | 98.7% | 98.9% | 99.4% | 99.6% |
| $^{225}$Ac-PSMA I&T Specific Activity | Reported | 0.198 MBq/nmol | 0.150 MBq/nmol | 0.142 MBq/nmol | 0.170 MBq/nmol |
| Radionuclidic Purity | ≥99.9% of the total activity of $^{225}$Ac at the end of production | N/A | N/A | N/A | N/A |
| Endotoxin | <175 EU/20 ml vial (<8.75 (EU/ml)) | N/A | N/A | N/A | N/A |
| Sterile Filter Integrity | ≥3.32 bar tested with water (Pall, Mini Kleenpak) | N/A | N/A | N/A | N/A |
| Radioactivity Content † | 90-110% at the date and time stated on the label | Pass | Pass | Pass | Pass |
| Sterility | Sterile | N/A | N/A | N/A | N/A |

TABLE 5c

| Stability Data (embodiment stable at 120 hours): Chemical quality at 120 h post end of synthesis | | | | | |
|---|---|---|---|---|---|
| ACMI2411C-1 | 120 h post End of Synthesis | | | | |
| VIAL | | 2 | 3 | 4 | 5 |
| Radioactivity * | | 6.24 MBq at 13 Mar. 2024 | 6.01 MBq at 13 Mar. 2024 | 6.15 MBq at 13 Mar. 2024 | 10.34 MBq at 13 Mar. 2024 |
| Fill Volume | | 10.00 ml | 9.99 ml | 10.00 ml | 16.96 ml |
| Storage Condition | | 5° C. ± 3° C. | 22.5° C. ± 2° C. | 32.5° C. ± 2° C. | 40° C. ± 2° C. |
| Sample taken at | | 18 Mar. 2024 17:18 | 18 Mar. 2024 17:18 | 18 Mar. 2024 17:18 | 18 Mar. 2024 17:18 |
| QC TESTING (STABILITY CRITERIA) | | | | | |
| Test | Specification | Results | | | |
| Appearance | Clear, colorless to yellow solution, no visible particles | Pass | Pass | Pass | Pass |
| pH | 5.5-7.0 | 5.5 | 5.5 | 5.5 | 5.5 |
| Ascorbic Acid | 5-15 mg/ml | 10 mg/ml | 10 mg/ml | 10 mg/ml | 10 mg/ml |
| Radionuclidic Identification | Energy from $^{225}$Ac daughter nuclide main peaks: $^{221}$Fr: 218.19 ± 4.36 keV (±2%, HPGe) $^{213}$Bi: 440.46 ± 8.81 keV (±2%, HPGe) | 218 keV and 441 keV | 218 keV and 441 keV | 218 keV and 441 keV | 218 keV and 441 keV |
| Radiochemical Identity | The highest amount of radioactivity elutes in the same fraction with $^{nat}$Lu-PSMA I&T and PSMA I&T. The HPLC fraction is collected between 13-18 minutes | Pass | Pass | Pass | Pass |
| Chemical Purity | Sum of PSMA I&T and Metal-PSMA I&T complexes ≤7.5 μg/ml | 3.6 μg/ml | 3.6 μg/ml | 3.6 μg/ml | 3.7 μg/ml |
| Radiochemical Purity by HPLC Method | ≥95.0% $^{225}$Ac-PSMA I&T | 97.2% Data Acquired 18 Mar. 2024 17:20:26 | 97.0% Data Acquired 18 Mar. 2024 17:54:32 | 96.5% Data Acquired 18 Mar. 2024 18:28:33 | 96.6% Data Acquired 18 Mar. 2024 19:04:33 |
| Radiochemical Purity by TLC Method | ≥95.0% $^{225}$Ac-PSMA I&T | 99.4% | 99.4% | 98.8% | 99.3% |
| $^{225}$Ac-PSMA I&T Specific Activity | Reported | 0.179 MBq/nmol | 0.173 MBq/nmol | 0.172 MBq/nmol | 0.168 MBq/nmol |
| Radionuclidic Purity | ≥99.9% of the total activity of $^{225}$Ac at the end of production | N/A | N/A | N/A | N/A |
| Endotoxin | <175 EU/20 ml vial (<8.75 (EU/ml)) | N/A | N/A | N/A | N/A |

TABLE 5c-continued

| Stability Data (embodiment stable at 120 hours): Chemical quality at 120 h post end of synthesis | | | | | |
|---|---|---|---|---|---|
| Sterile Filter Integrity | ≥3.32 bar tested with water (Pall, Mini Kleenpak) | N/A | N/A | N/A | N/A |
| Radioactivity Content † | 90-110% at the date and time stated on the label | Pass | Pass | Pass | Pass |
| Sterility | Sterile | N/A | N/A | N/A | N/A |

c. Process Validation

All validation batches for the embodiment of the composition stable at 48 hours were tested and confirmed to be sterile. The sterility test was validated on batches ACMI2119E-1, ACMI2119E-2, ACMI2123E-1, ACMI2123E-2 and ACMI2123E-3. Two sets of validation were performed from batch ACMI2119E-2. Batches ACMI2123E-1, ACMI2123E-2 and ACMI2123E-3 were produced as additional batches to confirm growth of a control microbe (*Candida albicans*) that did not show any growth in one of the control samples from batch ACMI2119E-2. Based on the results, no microbial inhibition was observed on any tested microbe and the observation for *C. albicans* on one sample was assessed to have been caused by a laboratory error.

The integrity of sterile filters was tested on all validation batches and all results conformed to specifications.

All validation batches were tested for endotoxins and conformed to specifications.

The process bioburden was tested at three batches and none showed microbiological growth over the detection limit. Bioburden sample was produced from batches ACMI2120E-1, ACMI2121A-1 and ACMI2121A-2 by removing the 0.22 μm filter from the dispensing process. The test was validated using the same batches. All three bioburden batches were also tested for chemical quality and complied to all specifications.

Altogether, it is concluded that the manufacturing process reliably produces $^{225}$Ac-PSMA I&T solution in satisfactory amounts and quality for clinical use under supervision of qualified healthcare professionals. Based on the results from the stability study provided in Tables 6a and 6b, the product needs to be stored at 5° C.-25° C. to maintain stability of 48 h.

TABLE 6a

| Chemical quality of validation batches (embodiment stable at 48 hours) | | | | |
|---|---|---|---|---|
| SYNTHESIS INFORMATION BATCH ID | | ACMI2114B-1 | ACMI2115D-1 | ACMI2115D-2 |
| Ac-225 | | Order No. 11045881 | Order No. 11046459 | Order No. 11046460 |
| Ac-225 Activity (MBq) | | 21 MBq 31 Mar. 2021 12:00 * | 19 MBq 12 Apr. 2021 12:00 | 19 MBq 12 Apr. 2021 12:00 * |
| Start of synthesis | | 6 Apr. 2021 09:22:24 | 15 Apr. 2021 08:13:15 | 15 Apr. 2021 09:02:38 |
| End of synthesis | | 6 Apr. 2021 09:49:21 | 15 Apr. 2021 08:40:13 | 15 Apr. 2021 09:29:35 |
| QC TESTING | | | | |
| Validation criteria Test | Specification | | | |
| Visual inspection | Clear, colorless or slightly yellow liquid, no visible particles | Pass | Pass | Pass |
| pH | 5.0-8.0 | 5.5 | 6.0 | 6.0 |
| $^{221}$Fr ja $^{213}$Bi main peaks gammaenergy | $^{221}$Fr: 218 ± 2 keV $^{213}$Bi: 440 ± 4 keV (HPGe-detector) | $^{221}$Fr: 218 keV $^{213}$Bi: 441 keV | $^{221}$Fr: 218 keV $^{213}$Bi: 440 keV | $^{221}$Fr: 218 keV $^{213}$Bi: 440 keV |
| Radioactivity concentration (MBq/ml) | No specification set | 0.895 MBq/ml 7 Apr. 2021 07:47 | 1.041 MBq/ml 16 Apr. 2021 09:00 | 1.121 MBq/ml 16 Apr. 2021 13:32 |
| Radiochemical purity % (TLC/HPGe) | $^{225}$Ac-PSMA I&T radioactivity ≥95% from total radioactivity | 96.5% | 95.3% | 96.6% |
| Chemical purity PSMA I&T | <12.0 μg/ml | 3.2 μg/ml | 7.5 μg/ml | 7.7 μg/ml |
| Chemical purity Other impurities | <12.0 μg/ml | 9.1 μg/ml | 6.1 μg/ml | 6.5 μg/ml |
| Specific activity | No specification set | 0.109 MBq/nmol | 0.114 MBq/nmol | 0.118 MBq/nmol |
| Radionuclidic purity | ≥99.9% | ≥99.9% | ≥99.9% | ≥99.9% |

TABLE 6a-continued

| Chemical quality of validation batches (embodiment stable at 48 hours) | | | | |
|---|---|---|---|---|
| Ascorbic acid | 20-70 mg/ml | 50 mg/ml | 50 mg/ml | 50 mg/ml |
| Bacterial endotoxins | <17.5 (EU/ml) | <5.00 | <5.00 | <5.00 |
| Filter integrity test | Bubble point >3.45 bar (water) | 3.87 | 4.16 | 3.97 |
| Sterility | Sterile | Sterile | Sterile | Sterile |

TABLE 6b

| Chemical quality of validation batches (embodiment stable at 48 hours) | | | | |
|---|---|---|---|---|
| SYNTHESIS INFORMATION BATCH ID | | ACMI2119B-1 | ACMI2119E-1 | ACMI2119E-2 |
| Ac-225 | | Order No. 11047251 | Order No. 11047252 | Order No. 11047253 |
| Ac-225 Activity (MBq) | | 16 MBq 10 May 2021 12:00 * | 17 MBq 12 May 2021 12:00 * | 10 MBq 12 May 2021 12:00 * |
| Start of synthesis | | 11 May 2021 08:14:40 | 14 May 2021 08:22:06 | 14 May 2021 09:02:00 |
| End of synthesis | | 11 May 2021 08:42:04 | 14 May 2021 08:49:30 | 14 May 2021 09:29:25 |
| QC TESTING | | | | |
| Validation criteria Test | Specification | | | |
| Visual inspection | Clear, colorless or slightly yellow liquid, no visible particles | Pass | Pass | Pass |
| pH | 5.0-8.0 | 5.5 | 5.5 | 5.5 |
| $^{221}$Fr ja $^{213}$Bi main peaks gammaenergy | $^{221}$Fr: 218 ± 2 keV $^{213}$Bi: 440 ± 4 keV (HPGe-detector) | $^{221}$Fr: 218 keV $^{213}$Bi: 441 keV | $^{221}$Fr: 218 keV $^{213}$Bi: 440 keV | $^{221}$Fr: 218 keV $^{213}$Bi: 440 keV |
| Radioactivity concentration (MBq/ml) | No specification set | 0.935 MBq/ml 12 May 2021 08:58 | 0.917 MBq/ml 16 May 2021 07:54 | 0.561 MBq/ml 16 May 2021 08:09 |
| Radiochemical purity % (TLC/HPGe) | $^{225}$Ac-PSMA I&T radioactivity ≥95% from total radioactivity | 95.5% | 96.1% | 96.2% |
| Chemical purity PSMA I&T | <12.0 μg/ml | 7.1 μg/ml | 6.6 μg/ml | 6.6 μg/ml |
| Chemical purity Other impurities | <12.0 μg/ml | 4.3 μg/ml | 6.3 μg/ml | 5.7 μg/ml |
| Specific activity | No specification set | 0.122 MBq/nmol | 0.107 MBq/nmol | 0.068 MBq/nmol |
| Radionuclidic purity | ≥99.9% | ≥99.9% | ≥99.9% | ≥99.9% |
| Ascorbic acid | 20-70 mg/ml | 30 mg/ml | 30 mg/ml | 30 mg/ml |
| Bacterial endotoxins | <17.5 (EU/ml) | <5.00 | <5.00 | <5.00 |
| Filter integrity test | Bubble point >3.45 bar (water) | 3.87 | 3.99 | 3.96 |
| Sterility | Sterile | Sterile | Sterile | Sterile |

The $^{225}$Ac-PSMA I&T manufacturing process for the 120 hour stable $^{225}$Ac-PSMA I&T composition was similarly evaluated by manufacture and testing of three (3) separate process validation/stability batches. Validation data for the 120 hour stable composition is depicted in Table 7. Batches were showing consistent results, and as previously indicated, the stability of the product has been evaluated over the assigned shelf life at storage temperatures ranging from 5° C.±3° C. to 40° C.±2° C. (See Tables 5a, 5b and 5c). Microbial bioburden studies were similarly performed on the three process validation batches.

Bioburden testing was also performed on the three (3) process validation batches to evaluate typical pre-sterilization bioburden challenge to the validated 0.22 μm sterilizing filter in the manufacturing process. None of the three batches showed microbial growth over the detection limit.

The results showed that the process met all pharmaceutical requirements for sterility and bacterial endotoxins according to the European pharmacopoeia, and all established quality and 120-hour stability results confirming an acceptable process from a manufacturing quality and pharmaceutical quality perspective.

TABLE 7

Chemical quality of process validation batches (embodiment stable at 120 hours)

PRODUCTION INFORMATION

| BATCH ID | ACMI2409C-1 | ACMI2409C-2 | ACMI2411C-1 |
|---|---|---|---|
| $^{225}$Ac $(NO_3)_3$ | No. 04/24-Ac 03763 | No. 04/24-Ac 03764 | No. 05/24-Ac 03765 |
| $^{1225}$Ac $(NO_3)_3$ Radioactivity, mCi (MBq) * | 1 mCi (37 MBq) 28 Feb. 2024 | 1 mCi (37 MBq) 28 Feb. 2024 | 1 mCi (37 MBq) 13 Mar. 2024 |
| Start of Synthesis | 09:33:18 28 Feb. 2024 | 10:07:32 28 Feb. 2024 | 15:58:26 13 Mar. 2024 |
| End of Synthesis | 09:57:32 28 Feb. 2024 | 10:31:46 28 Feb. 2024 | 16:22:41 13 Mar. 2024 |
| Bulk Product Volume | 54.6 ml | 54.6 ml | 53.4 ml |
| Radioactivity Concentration (MBq/ml) | 0.538 MBq/ml<br>10:06 29 Feb. 2024 | 0.537 MBq/ml<br>10:18 29 Feb. 2024 | 0.596 MBq/ml<br>07:11 14 Mar. 2024 |

QC TESTING (VALIDATION CRITERIA)

| Test | Specification | Results | | |
|---|---|---|---|---|
| Appearance | Clear, colorless to yellow solution, no visible particles | Pass | Pass | Pass |
| pH | 5.5-7.0 | 6.0 | 6.0 | 6.0 |
| Ascorbic Acid | 5-15 mg/ml | 10 mg/ml | 10 mg/ml | 10 mg/ml |
| Radionuclidie Identification | Energy from $^{225}$Ac daughter nuclide main peaks: $^{221}$Fr: 218.19 ± 4.36 keV (±2%, HPGe) $^{213}$Bi: 440.46 ± 8.81 keV (±2%, HPGe) | 218 keV and 441 keV | 218 keV and 441 keV | 218 keV and 441 keV |
| Radiochemical Identity | The highest amount of radioactivity elutes in the same fraction with $^{nat}$Lu-PSMA I&T and PSMA I&T. The HPLC fraction is collected between 13-18 minutes | Pass | Pass | Pass |
| Chemical Purity | Sum of PSMA I&T and M-PSMA I&T complexes ≤7.5 μg/ml | 4.0 μg/ml | 4.2 μg/ml | 4.5 μg/ml |
| Radiochemical Purity by HPLC Method | ≥95.0% 225 Ac-PSMA I&T | 98.8%<br>Data Acquired<br>28 Feb. 2024 12:45:09 | 98.8%<br>Data Acquired<br>28 Feb. 2024 13:22:09 | 98.7%<br>Data Acquired<br>13 Mar. 2024 17:07:14 |
| Radiochemical Purity by TLC Method | ≥95.0% 225 Ac-PSMA I&T | 99.8% | 99.7% | 99.5% |
| 225 Ac-PSMA I&T Specific Activity | Reported | 0.202 MBq/nmol | 0.193 MBq/nmol | 0.198 MBq/nmol |
| Radionuclidic Purity | ≥99.9% of the total activity of $^{225}$Ac at the end of production | >99.9% | >99.9% | >99.9% |
| Endotoxin | <175 EU/20 ml vial (<8.75 (EU/ml)) | <5.00 EU/ml | <5.00 EU/ml | <5.00 EU/ml |
| Sterile Filter Integrity | ≥3.32 bar tested with water (Pall, Mini Kleenpak) | 3.96 bar | 4.09 bar | 3.80 bar |
| Radioactivity Content | 90-110% at the date and time stated on the label | N/A | N/A | N/A |
| Sterility | Sterile | Sterile | Sterile | Sterile |

d. Clinical Experience in $^{225}$Ac-PSMA

Bismuth-213 (213Bi) for PSMA-targeted α-therapy (TAT) is a mixed α- and β-emitter with a radioactive half-life of 45.6 min and it is produced from Ac-225 decay (FIG. 2). Small molecule PSMA I&T induced more double-strand breaks than the nanobody in nonclinical studies, where targeted α-therapy with 213Bi labelled antibody (J591), small molecule inhibitor PSMA I&T or nanobody (JVZ-008) were compared; they demonstrated tumor targeting and tumor growth inhibition in nude mice with PSMA-overexpressing xenografts. Dosimetry calculations with 213Bi-PSMA-617 and $^{225}$Ac-PSMA-617 demonstrated the superiority of $^{225}$Ac as compared to short-lived 213Bi as the radionuclide label for PSMA-617. Probably therefore, there is only one single patient case reported to date on the use of 213Bi-PSMA-617. The patient was treated with two cycles of 213Bi-PSMA-617 with a cumulative activity of 592 MBq. The serum PSA concentration decreased from 237 μg/l down to 43 μg/l as a sign of biochemical response. Also, the short radioactive half-life of 213Bi makes this radionuclide less suitable for routine clinical therapeutic applications.

TABLE 8

Clinical trials of Actinium-225-PSMA-targeted alpha therapy.

| | Number of patients | Activity per cycle/MBq | Biochemical response $PSA_{50}$ | PFS/OS [mo] | Major toxicity | First author |
|---|---|---|---|---|---|---|
| PSMA-617 | 2 | 100 kBq/kg | 100% (2/2) | | xerostomia | Kratochwil 2016 |

TABLE 8-continued

Clinical trials of Actinium-225-PSMA-targeted alpha therapy.

| | Number of patients | Activity per cycle/MBq | Biochemical response $PSA_{50}$ | PFS/OS [mo] | Major toxicity | First author |
|---|---|---|---|---|---|---|
| PSMA-617 | 14 | 50-200 kBq/kg | 44% (4/9) | na/8.5 | xerostomia | Kratochwil 2017 |
| PSMA-617 | 40 | 100 kBq/kg | 63% (24/38) | na/>12 | xerostomia | Kratochwil 2018 |
| PSMA-617 | 1 | 8 | 100% (1/1) | | | Sathekge 2019a |
| PSMA-617 | 17 | 4-8 | 88% (15/17) | | xerostomia | Sathekge 2019b |
| PSMA-617 | 1 | 6-8 | 100% (1/1) | | xerostomia xerophtalmia | De Medeiros 2019 |
| PSMA-617 | 73 | 4-8 | 70% (51/73) | 15.2/18.0 | | Sathekge 2020 |
| PSMA-617 | 26 | 4-8 | 65% (17/26) | 3.5/7.7 | xerostomia Hb↓, WBC↓, plt↓ | Feuerecker 2020 |
| PSMA-617 | 28 | 100 kBq/kg | 39% (11/28) | 12/17 | xerostomia fatigue | Yadav 2020 |
| PSMA-617 | 13 | 6-8 | 69% (9/13) | na/8.5 | xerostomia | van der Doelen 2020 |
| PSMA I&T | 1 | 8 | 100% (1/1) | | xerostomia | Ilhan 2020 |
| PSMA I&T | 14 | 7.8 | 50% (7/14) | | xerostomia | Zacherl 2021 |

$^{225}$Ac has a radioactive half-life of 9.9 days and decays to produce four alpha particles with an energy of 5.8-8.4 MeV, with a tissue range of up to 85 μm. This alpha emitter has been labelled to PSMA ligands as $^{225}$Ac-PSMA for targeted alpha therapy (TAT). $^{225}$Ac deposits high energy resulting in irreparable double-strand DNA destruction whilst sparing surrounding normal tissue making it an attractive anti-tumor agent. Clinical application of $^{225}$Ac-PSMA TAT as last line of therapy in patients with mCRPC has demonstrated an excellent response, e.g., chemotherapy naive patients, although most clinical studies report it as third-line therapy or after a failure of $^{177}$Lu-PRLT. Widespread application of $^{225}$Ac-PSMA TAT is hampered by its salivary gland toxicity (xerostomia). The clinical studies listed above in Table 8, are described in a more detailed manner below.

In a study with the first-in-human use of $^{225}$Ac-PSMA-617 Kratochwil et al., which is herein incorporated by reference in its entirety, reported complete response in two patients with mCRPC who had failed multiple lines of previous therapy. Because of challenging clinical situations and extensive pretreatment, the patients were treated with 100 kBq/kg of $^{225}$Ac-PSMA-617 at every 8 weeks as salvage therapy after the presence of a PSMA-positive tumor phenotype had been validated by 68Ga-PSMA-11 PET/CT. The first patient was not suitable for $^{177}$Lu-PSMA-617 because of widespread marrow disease and the second one progressed from $^{177}$Lu-PSMA therapy presenting with diffuse abdominal and liver disease. Both patients showed a complete response on the 68Ga-PSMA-11 PET/CT scan, and PSA declined below the measurable level. Xerostomia was reported in both patients.

The second study with 14 mCRPC patients found that a treatment activity of 100 kBq/kg of body weight of $^{225}$Ac-PSMA-617 per cycle every 8 weeks was the most optimal when considering both efficacy (biochemical response) and tolerability. Severe xerostomia was the dose-limiting toxicity. The optimal dose is discussed in the dosimetry section.

Figures 3A, 3B:
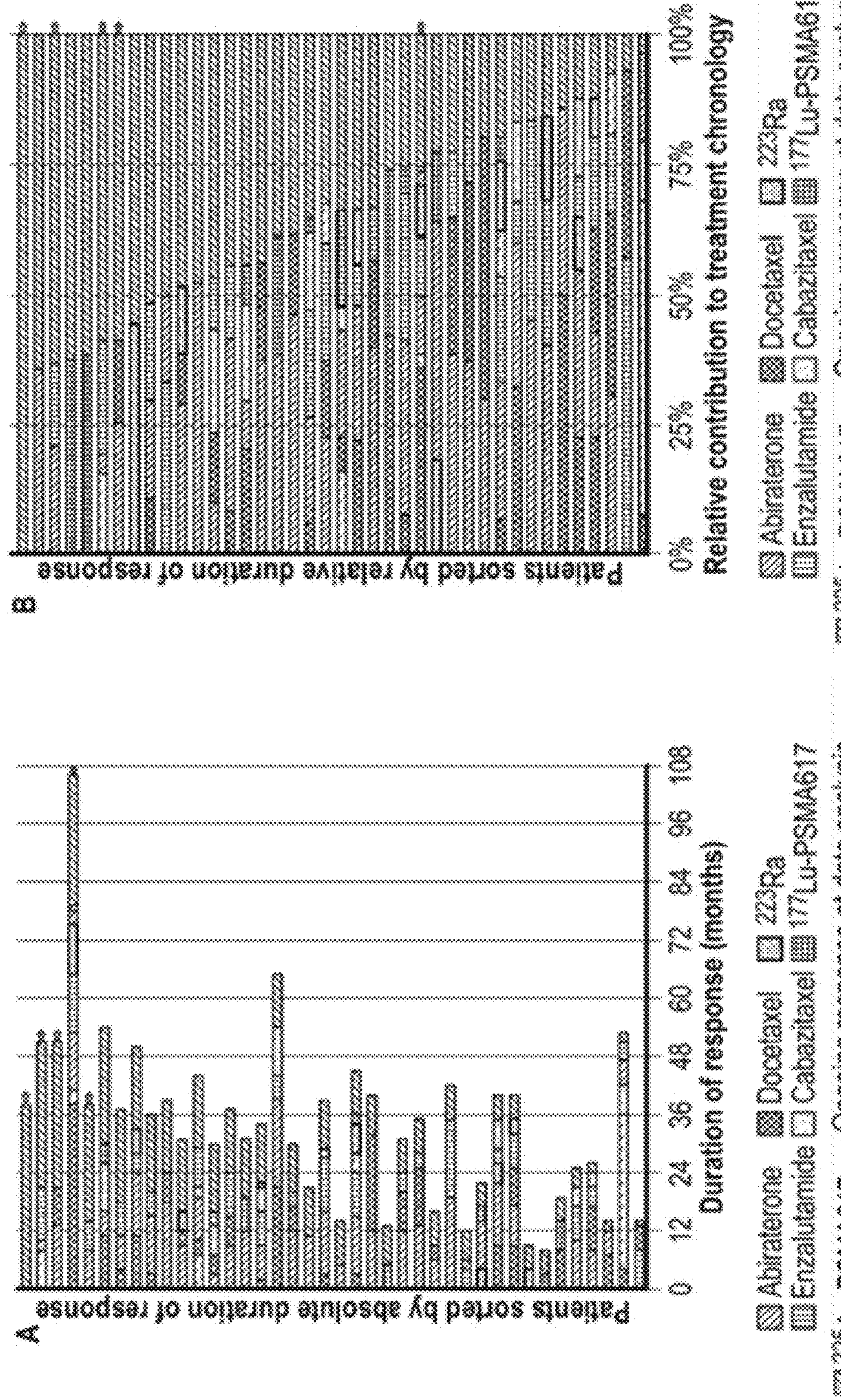
FIGS. 3A & 3B depict therapy sequences, lengths in an $^{225}$Ac-PSMA trial.

Kratochwil et al. also reviewed the efficacy of $^{225}$Ac-PSMA-617 in a large cohort of 40 patients with advanced disease. All patients had mCRPC and had failed or were ineligible for conventional therapy; 70%, 85% and 60% of the patient cohort had had prior docetaxel, abiraterone and enzalutamide, respectively. FIGS. 3A &3B demonstrate the therapy sequences and durations of effects in these patients on an absolute (FIG. 3A) and relative scale (FIG. 3B); the green color represents the 225Ac-PSMA-617 therapy (FIGS. 3A & 3B). 68Ga-PSMA PET/CT and $^{99m}$Tc-PSMA SPECT/CT imaging was used for patient selection with patients with limited disease selected for $^{177}$Lu-PSMA radioligand therapy whilst those with diffuse uptake on imaging were treated with $^{225}$Ac-PSMA, those patients who demonstrated no tumor uptake on imaging were declined TAT. An activity of 100 kBq/kg $^{225}$Ac-PSMA-617 was administered for 8 weeks for a minimum 3 and up to 5 cycles.

Figure 4:
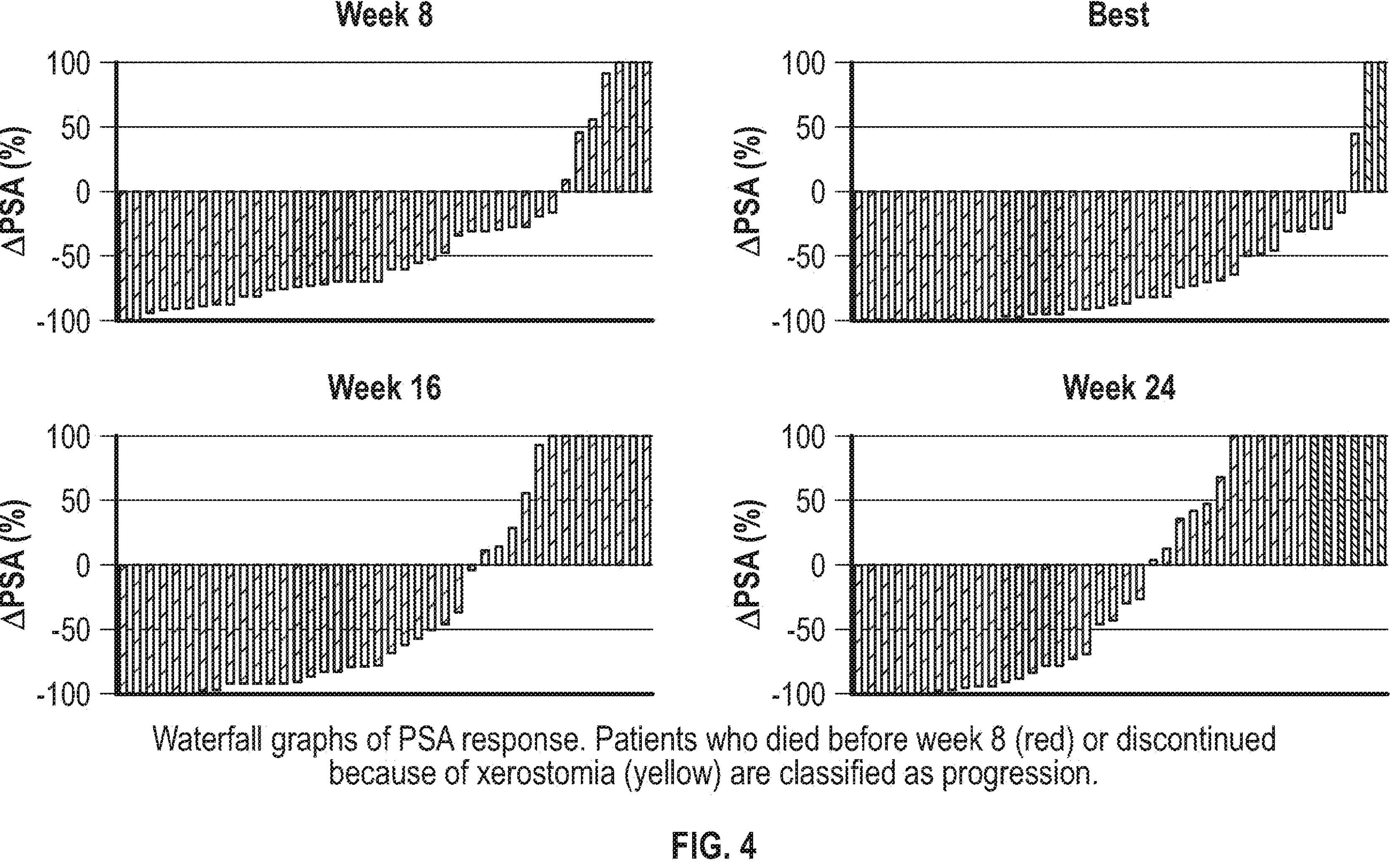
FIG. 4 depicts PSA responses in an $^{225}$Ac-PSMA trial.

This study demonstrated a PSA decline of more than 50% in 63% of patients, with a median duration of tumor control of 9 months. The median overall survival was more than 12 months. 38 patients out of 40 survived at least 8 weeks with 63% of these patients demonstrating a PSA response >50% and 87% demonstrating any PSA response, a median overall survival and progression free survival of >12 and 7.0 months was demonstrated. The PSA responses are shown as waterfall-plots at weeks 8, 16, 24 in FIG. 4.

This standardized treatment protocol for $^{225}$Ac-PSMA-617 is routinely applied for salvage therapy of end-stage mCRPC patients in many studies. Feuerecker et al. investigated $^{225}$Ac-PSMA-617 TAT in 26 patients who had failed a median of six lines of previous therapy for mCRPC, all had progressed after $^{177}$Lu-PSMA therapy. A PSA decline of >50% was demonstrated in 65% of the patients while 88% of the patients demonstrated any PSA reduction. However, no complete response was seen in the population. The median overall survival was 7.7 months (95% CI 4.5-12.1 months). Mild irreversible xerostomia was seen in all patients with 23% of patients refusing any further treatment due to severe xerostomia, 8% of the patients had to have their treatment discontinued to prevent further deterioration of marrow toxicity which had been pre-existing. Poor prognosis could be seen in the patients who had failed previous $^{177}$Lu-PSMA including the presence of liver metastases and higher ECOG status.

Similar findings were described by Yadav et al. where 28 patients with mCRPC were enrolled to receive $^{225}$Ac-PSMA-617 TAT, 54% of these patients had failed $^{177}$Lu-PSMA therapy whilst 46% were $^{177}$Lu-PSMA therapy naïve. A comparison of the two groups, previous $^{177}$Lu-PSMA and $^{177}$Lu PSMA naïve, demonstrated a PSA decline of >50% and progression rate of 26.6% and 46% vs 53.8% and 22.3% respectively. Interestingly, there was no difference in median survival and overall survival between the two groups, 10 vs. 12 months and 16 vs. 17 months, respectively.

Sathekge et al. investigated $^{225}$Ac-PSMA in 17 patients who were chemotherapy naive. $^{225}$Ac-PSMA-617 was administered in 2-monthly intervals. An initial activity of 8 MBq was administered with response assessments determined using PSA and $^{68}$Ga-PSMA PET/CT imaging prior to subsequent cycles of $^{225}$Ac-PSMA. A "dynamic dose-reduction" was used where the subsequent activity of $^{225}$Ac-PSMA was reduced in patients who had demonstrated a response to the previous cycle, the mean administered activity was 7.4±1.5 MBq, with 3 of the 17 patients only receiving 2 cycles of therapy after having demonstrated an excellent response. A PSA decline >90% was seen in 82% of the patients at end of therapy, at median follow up of 13 months post initiation of treatment 82% of the patients were still alive with 50% of these patients in remission demonstrating undetectable serum PSA levels and the other 50% with stable disease. Grade 1-2 xerostomia was the most frequently noted side-effect with no discontinuation in therapy reported due to severe symptoms. Grade 4 nephrotoxicity was noted in a patient with only a single functional kidney who had poor renal functioning from baseline.

Figure 5:
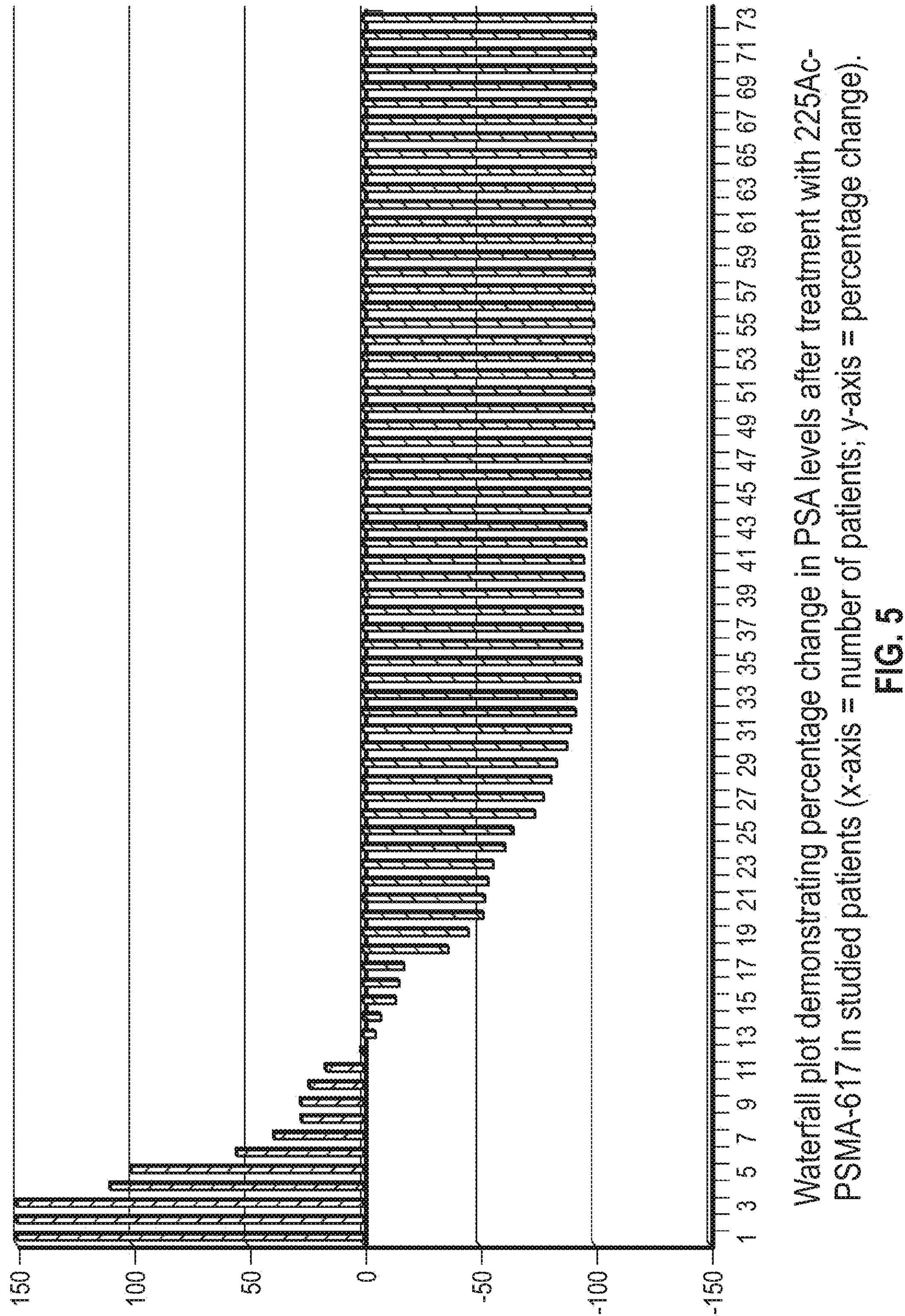
FIG. 5 depicts PSA responses in 73 patients in the largest $^{225}$Ac-PSMA trial.

Sathekge et al., in the largest study population to date, enrolled 73 men with mCRPC who failed standard therapy, 14 of these patients had prior $^{177}$Lu-PSMA therapy. At the end of $^{225}$Ac-PSMA-617 therapy, 70% of the patients demonstrated a ≥50% PSA decline while 82% had any decline in PSA, response shown in FIG. 5. Post therapy, 68Ga-PSMA PET/CT images were negative in 29% of the patients. Median OS and PFS were determined to be 18 months (95% CI, 16.2-19.9 months) and 15.2 months (95% CI, 13.1-17.4 months) respectively, 13 patients had passed away while 23 patients had demonstrated disease progression. Factors found to be associated with higher OS and PFS included baseline PSA, PSA decline ≥50%, prior chemotherapy, prior radiation therapy, and Hb at baseline, while prior radioligand therapy with $^{177}$Lu-PSMA was associated with a poorer PFS.

Since PSMA-617 crosses the blood-brain barrier and accumulates in cerebral metastases, a significant regression of cerebral metastases was demonstrated using $^{225}$Ac-PSMA-617. Prostate cancer patients with brain metastases have limited treatment options and poor survival, and TAT with $^{225}$Ac-PSMA-617 may have substantial therapeutic potential for these patients. Also, encouraging response to TAT in a patient with advanced mCRPC showing progression after long-term $^{177}$Lu-PSMA RLT (10 cycles) has been reported (see FIG. 6). Image of the first patient exceeding 5-year complete remission after $^{225}$Ac-PSMA-TAT are shown in FIG. 7.

Figure 6:
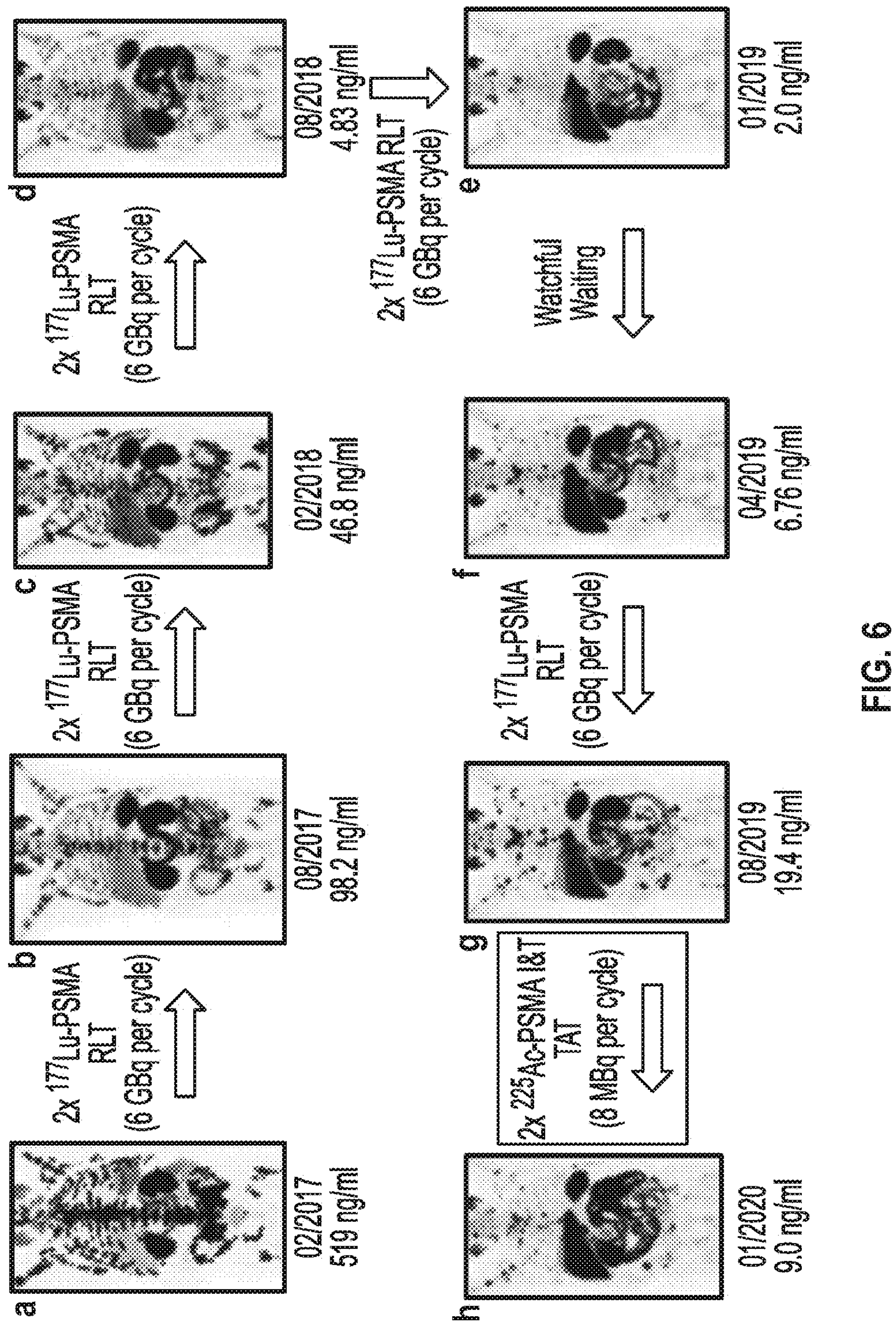
FIG. 6 depicts a response with $^{225}$Ac-PSMA after 10 cycles of $^{177}$Lu-PSMA.

The patient in FIG. 6 received two cycles of $^{225}$Ac-PSMA I&T after failure $^{177}$Lu-PSMA-617 and showed encouraging response (H). The main TAT-related side effect was grade 2 xerostomia (grade 2), which was already preexisting after 10 cycles of RLT. No TAT-related grade 3/4 hematological side effects were noted.

Figure 7:
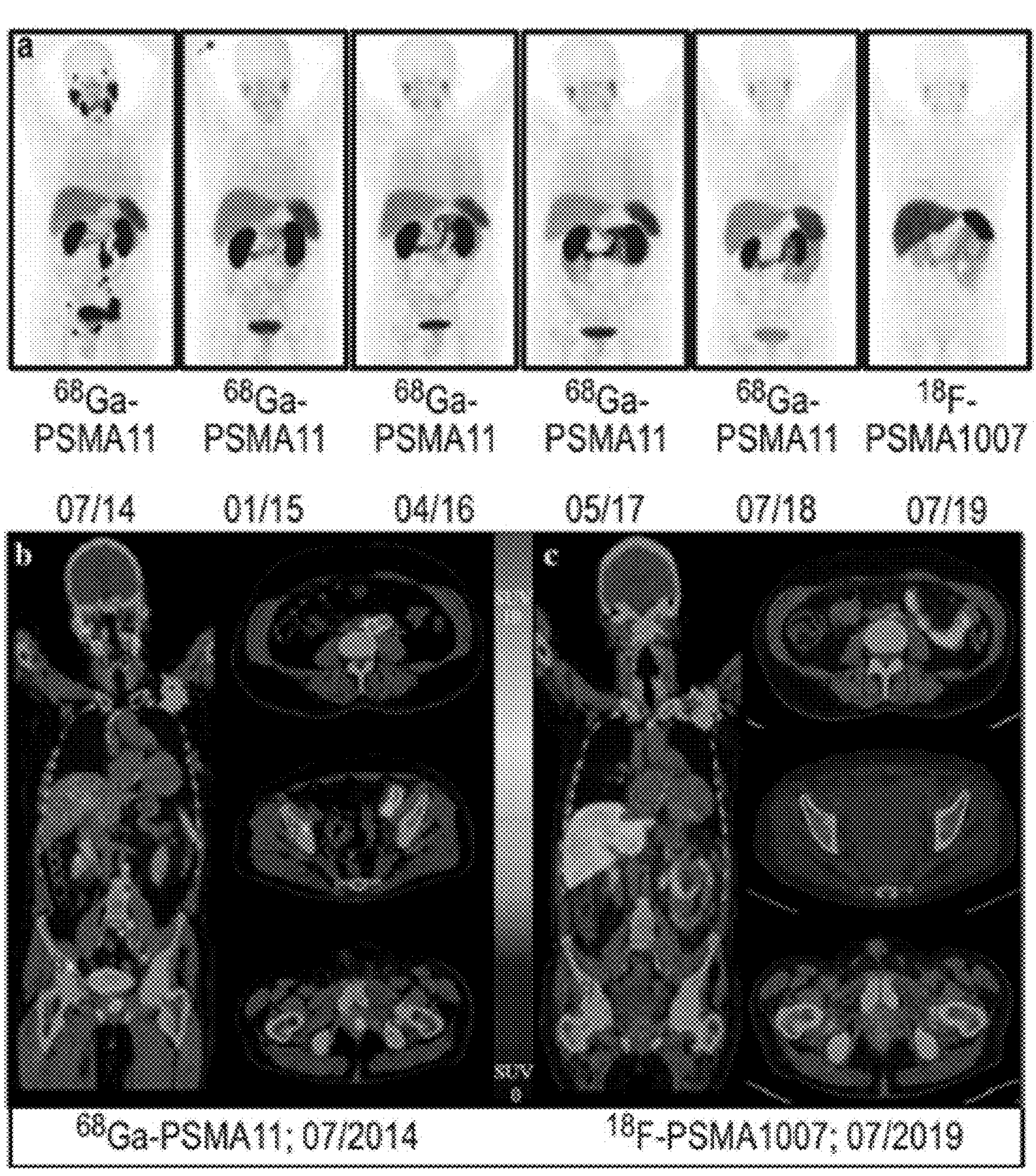
FIG. 7 depicts a 5-year complete response with $^{225}$Ac.

The patient in FIG. 7 in July/September/November 2014, received 3 cycles of mean 8.4-MBq $^{225}$Ac-PSMA-617 at PSA levels of 39.7, 7.7, and 0.32 ng/ml, respectively. This patient developed chronic xerostomia, and with some delay, creatinine increased from 1.3 in October 2015 to 3.3 mg/dl in January 2019. This could partially be related to the renal radiation exposure of PSMA therapy, but also with concomitant cardiorenal syndrome, diabetes, and arterial hypertension.

PMSA-617 has been a main theragnostic agent which has been under review in TAT in mCRPC, however PSMA I&T has been investigated in $^{177}$Lu-PSMA radioligand therapy and did not show any inferiority in the literature when compared to $^{177}$Lu-PSMA-617. The first clinical data using $^{225}$Ac-PSMA I&T showed highly comparable biochemical responses to those seen after $^{225}$Ac-PSMA-617 TAT.

Zacherl et al. were the first to study a clinical cohort with PSMA I&T in TAT. Fourteen patients who were either not eligible for or had failed conventional therapy were included in the study with 79% of these patients having had received prior $^{177}$Lu-PSMA radioligand therapy. 18F-PSMA-1007 PET/CT was used to assess suitability for therapy. This group demonstrated a PSA decline ≥50% of 45% and any PSA decline of 73% in the subgroup of patients who had received prior $^{177}$Lu-PSMA radioligand therapy which is comparable with other groups which have investigated $^{225}$Ac-PSMA therapy in patients who have failed $^{177}$Lu-PSMA radioligand therapy.

Figure 8:
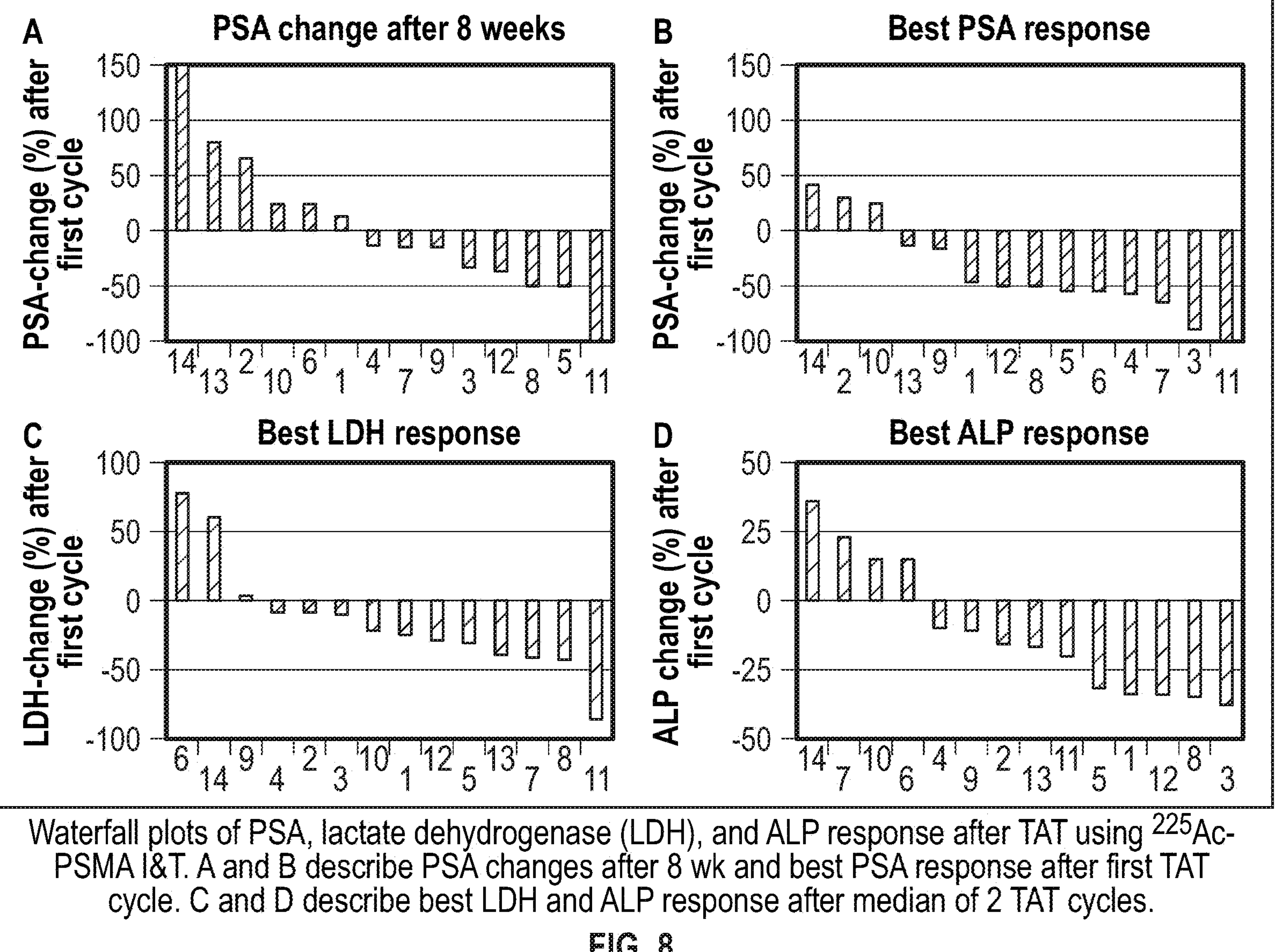
FIG. 8 depicts PSA-response with $^{225}$Ac-PSMA I&T.

Fourteen patients receiving $^{225}$Ac-PSMA I&T were included in this retrospective analysis: Eleven of the 14 had prior second-line antiandrogen treatment with abiraterone or enzalutamide, prior chemotherapy, and prior $^{177}$Lu-PSMA treatment. Patients were treated at bimonthly intervals until progression or intolerable side effects. Thirty-four cycles of $^{225}$Ac-PSMA I&T were applied (median dose, 7.8 MBq; range, 6.0-8.5), with 1 cycle in 3 patients, 2 cycles in 7 patients, 4 cycles in 3 patients, and 5 cycles in 1 patient. No acute toxicity was observed during hospitalization. Baseline PSA was 112 ng/ml (range, 20.5-818 ng/ml). The best PSA response after TAT (a PSA decline ≥50%) was observed in 7 patients, and a PSA decline of any amount was observed in 11 patients (FIG. 8). Three patients had no PSA decline at any time. A subgroup analysis of 11 patients with prior $^{177}$Lu-PSMA treatment showed any PSA decline in 8 patients and a decline of at least 50% in 5 patients; one patient is shown in FIG. 9. After TAT, grade 3 anemia was observed in 3 of the 14 patients, with 2 of them presenting with grade 2 anemia already at baseline. Grade 3 leukopenia was observed in 1 patient. Eight patients with preexisting xerostomia after $^{177}$Lu-PSMA showed no worsening after TAT. Newly diagnosed grade 1 or 2 xerostomia after TAT was observed in 5 patients. One patient reported no xerostomia at all.

Radioresistance as a result of mutations in the genes responsible for DNA repair has been thought to be the reason that some patients did not demonstrate a response to $^{225}$Ac-PSMA TAT despite demonstrating tumor PSMA expression as evidenced by intense tumor uptake of tracer on PSMA PET/CT imaging. A combination of $^{225}$Ac-PSMA TAT and poly (ADP-ribose)-polymerase (PARP) inhibitors, a DNA damage-repair-targeting molecule has been suggested for these patients to overcome the radioresistance.

Kratochwil et al. identified 10 patients out of 60 who presented with a poor response to $^{225}$Ac-PSMA-617, despite sufficient tumor uptake in PSMA PET/CT. CT-guided biopsies with histologic validation were taken of the nonresponding lesions in 7 of these nonresponding patients, their characteristics are shown in FIG. 10.

Specimens were analyzed by next generation sequencing (NGS) interrogating 37 DNA damage-repair-associated genes. 7 tumor samples analyzed, were found a total of 15 whole-gene deletions, deleterious or presumably deleterious mutations affecting TP53 (n=3), CHEK2 (n=2), ATM (n=2), and BRCA1, BRCA2, PALB2, MSH2, MSH6, NBN, FANCB, and PMS1 (n=1 each). The average number of deleterious or presumably deleterious mutations was 2.2 (range, 0-6) per patient. In addition, several variants of unknown significance in ATM, BRCA1, MSH2, SLX4, ERCC, and various FANC genes were detected. The summary of NGS data is shown in FIG. 11.

Patients with resistance to PSMA-TAT despite PSMA positivity frequently harbor mutations in DNA damage-repair and checkpoint genes findings encourage future studies combining PSMA-TAT and DNA damage-repair-targeting agents such as PARP inhibitors.

e. $^{225}$Ac-PSMA TAT Toxicity Profile

Regarding salivary glands, in the clinical setting, several studies reported toxicity related to TAT with $^{225}$Ac-PSMA-617/PSMA I&T (Table 9). FIG. 12 represents the toxicity profiles in the largest reported study with $^{225}$Ac-PSMA-617. Xerostomia is a common side effect that causes 10-25% of patients to stop TAT with $^{225}$Ac-PSMA. Xerostomia should, therefore, be prevented. Modification of the administered activity of $^{225}$Ac-PSMA-617 and the number of cycles of TAT may decrease the side effects while still achieving response. Sialendoscopy with dilatation, saline irrigation, and steroid injection (prednisolone) have been investigated in patients with some but limited success. Eleven men with metastatic castration-resistant prostate cancer underwent sialendoscopy, dilatation, saline irrigation and steroid injection of both submandibular and both parotid glands before or after every cycle of $^{225}$Ac-PSMA-617 TAT.

TABLE 9

Toxicities in 73 patients after $^{225}$Ac PSMA-617

| Toxic Effect | Grade I or II | Grade III | Grade IV |
|---|---|---|---|
| Dry Mouth | 62 (85) | 0 | 0 |
| Dry Eyes | 4 (5) | 0 | 0 |
| Anorexia | 23 (32) | 0 | 0 |
| Nausea | 15 (21) | 0 | 0 |
| Vomiting | 4 (5) | 0 | 0 |
| Constipation | 19 (26) | 0 | 0 |
| Fatigue | 37 (51) | 0 | 0 |
| Weight Loss | 28 (38) | 0 | 0 |
| Dyspepsia | 3 (4) | 0 | 0 |
| Dysgeusia | 4 (5) | 0 | 0 |
| Anemia | 22 (30) | 5 (7) | 0 |
| Leukopenia | 7 (10) | 2 (3) | 0 |
| Thrombocytopenia | 6 (8) | 1 (1) | 0 |
| Hypoalbuminemia | 14 (19) | 0 | 0 |
| Renal Failure | 18 (25) | 3 (4) | 2 (3) |
| Dysuria | 13 (18) | 0 | 0 |

*Data are reported as numbers of patients, with percentages of patients in parentheses.

Sialendoscopy and steroid injection were performed by a senior otolaryngologist. Quality of life (QoL) was evaluated by general quality of life and specific xerostomia questionnaires, before and 3 months after the intervention. In all 11 patients, both parotid and both submandibular glands were affected by radiation sialadenitis and sialendoscopy was performed. Sialendoscopy with dilatation, saline irrigation and steroid injection had beneficial effects on salivary gland function and QoL in patients undergoing $^{225}$Ac-PSMA-617 RLT. However, even with sialadenoscopic support after multiple cycles of TAT, salivary gland function was reduced and xerostomia was present. Therefore, not only inflammation, but also the direct effect of radiation is a putative cause of dry mouth.

A case report in one patient describes the potential beneficial effects of intraparenchymal injections of botulinum toxin before $^{225}$Ac-PSMA-617 TAT. External cooling of the salivary gland using ice packs from 30 min pre-infusion through 2 h post-infusion of radiopharmaceuticals was expected to reduce PSMA radioligand uptake due to vasoconstriction. However, the relative contributions of salivary gland cooling and the reduced $^{225}$Ac-PSMA-617 activity in minimizing xerostomia severity remain unclear. Therefore, effective methods to reduce salivary toxicity are needed.

Regarding the kidneys, due to the physiological expression of PSMA in kidneys and predominantly renal excretion of $^{225}$Ac-PSMA-617, there is concern about possible radiation toxicity to the kidneys that may cause acute and long-term effects. It has been reported that the kidney function deteriorated in a patient with one functional kidney after $^{225}$Ac-PSMA-617 and that chronic kidney disease was found in two patients with mCRPC after $^{225}$Ac-PSMA-617 therapy. Until now, retention times of PSMA ligands either in kidneys or in tumor cells have not yet been evaluated systematically. If PSMA on the surface of cancer cells is not sufficiently internalized after binding of the ligand, TAT with $^{225}$Ac with multiple unstable daughters might be suboptimal and toxic. It has also been speculated that the radioactive daughters of $^{225}$Ac, but not $^{225}$Ac-PSMA-617, can accumulate in the tubular cells and irradiate the kidneys, leading to renal injury. In FIG. 13 the toxicity data has been presented in 14 patients receiving $^{225}$Ac-PSMA I&T, in this cohort only one patient showed grade 1 nephrotoxicity.

Regarding hematologic toxicity, in FIG. 13 the hematologic toxicity in 14 patients receiving $^{225}$Ac-PSMA I&T is mild, with single patients demonstrating grade 3 anemia and grade 3 leucopenia. The short path length of alpha particles (47-85 μm) may explain the low hematological toxicity seen in patients treated with $^{225}$Ac-PSMA, even if the marrow is infiltrated by tumor cells. Baseline myelosuppression may be a contributor to increased severity of hematological toxicity. Baseline image findings of diffuse widespread marrow involvement has also been found to be a predictor for hematological toxicity Though PSMA is highly expressed prostate cancer cells, physiological expression of PSMA is seen in the lacrimal glands, salivary glands, gastrointestinal tract, and renal tubular cells. Binding to these non-malignant-tissue PSMA expressing sites is responsible for the side effects that are seen with $^{225}$Ac-PSMA therapy. Probably, therefore also xeropthalmia has been reported after $^{225}$Ac-PSMA-TAT. Safety measures that may be adopted to reduce the risk of developing nephrotoxicity include baseline screening, e.g., with $^{99m}$Tc-MAG3 scintigraphy for obstructive renal pathology and correction where feasible and co-administration of normal saline with the radioligand. Patients with poor baseline renal function may be at risk of developing severe nephrotoxicity. Most patients have demonstrated favorable nephrotoxicity to $^{225}$Ac-PSMA. However, it is known that with radionuclide therapy radiation induced renal injury may develop at a delayed stage, and thus, be missed in the reported cohorts.

Salivary gland toxicity is the most common toxicity from TAT with $^{225}$Ac-PSMA. Symptoms from xerostomia may range from mild symptoms to severe symptoms without requiring dietary changes to severe symptoms requiring nasogastric feeding or total parenteral nutrition. In a case series salivary gland toxicity was the dose limiting factor as patients refused any further treatment with $^{225}$Ac-PSMA due to intolerable xerostomia. Salivary gland toxicity is dose dependent, even irreversible severe xerostomia may develop when high cumulative activity is administered. To improve salivary gland toxicity, Sathekge et al. used a "dynamic de-escalation" where 8 MBq of $^{225}$Ac-PSMA was the initial activity. If the patient demonstrated a good response after the first cycle then the subsequent activity was reduced by 2 MBq, this process is then repeated again prior to the third cycle down to 4 MBq. This approach resulted in patients reporting only grade II xerostomia and no need for withdrawal of treatment due to salivary gland toxicity. Tandem administration of a reduced $^{225}$Ac-PMSA and full dose $^{177}$Lu-PMSA has also been used as an alternative approach to reduce the severity of salivary gland toxicity without compromising PSA response.

f. Dosimetry Aspects

Dosimetry studies have demonstrated that the salivary glands receive the highest absorbed dose of the non-target organs. The mechanism of PSMA uptake in the salivary glands has not been fully understood. To date, several interventions have been reviewed to improve patient quality of life, however these attempts at preventing salivary gland toxicity have been unsuccessful. These strategies have been discussed earlier and in order to predict the grade of salivary gland toxicity the absorbed radiation dose should be measured.

The basis for clinical dosimetry calculations has been the relative biological effectiveness (RBE=5) found in an experimental study in a mouse model using immunohistochemical γH2AX-foci formation as an indicator for the amount of DNA double-strand breaks. The response to internal radiotherapy between α- and β-emission ($^{225}$Ac/$^{177}$Lu) as a biological consequence of different ionization-densities along a particle-track was measured in somatostatin expressing AR42J cells which were incubated with octreotate analogs $^{225}$Ac-DOTATOC and $^{177}$Lu-DOTATOC up to 48 h. The cell viability was analyzed using the common MTT assay. DNA double-strand breaks were quantified by immunofluorescence staining of γH2AX-foci and cell cycle was analyzed by flow cytometry. In vivo uptake of both radiolabelled somatostatin-analogues into subcutaneously growing AR42J tumors and the number of cells displaying γH2AX-foci were measured.

$^{225}$Ac-DOTATOC resulted in $ED_{50}$ values of 14 kBq/ml after 48 h, whereas $^{177}$Lu-DOTATOC displayed $ED_{50}$ values of 10 MBq/ml. The number of DNA double-strand breaks grew with increasing concentration of $^{225}$Ac-DOTATOC and similarly with $^{177}$Lu-DOTATOC when applying a factor of 700-fold higher activity compared to $^{225}$Ac.

The clinical dosimetry basis and dose finding study was performed by using the isotopes $^{225}$Ac and $^{177}$Lu by Kratochwil et al. A dosimetry estimate was calculated on the basis of time-activity curves derived from serially obtained $^{177}$Lu-PSMA-617 scans extrapolated to the physical half-life of $^{225}$Ac, assuming instant decay of unstable daughter nuclides. Salvage therapies empirically conducted with 50 (n=4), 100 (n=4), 150 (n=2), and 200 kBq/kg (n=4) of $^{225}$Ac-PSMA-617 were evaluated retrospectively regarding toxicity and treatment response. Eight of 14 patients received further cycles in either 2- or 4-mo intervals with identical or de-escalated activities. The patient characteristics are shown in FIG. 14.

From this prior study, the following dosimetry estimates were observed for 1 MBq of $^{225}$Ac-PSMA-617 assuming a relative biologic effectiveness of 5:2.3 Sv for salivary glands, 0.7 Sv for kidneys, and 0.05 Sv for red marrow that are composed of 99.4% α-, 0.5% β-, and 0.1% photon radiation, respectively. In FIG. 15, the absorbed radiation dose estimates for $^{225}$Ac-PSMA-617 are shown together with I-131-"PSMA" and $^{177}$Lu-PSMA-617 doses. It can be seen that the mean dose for salivary glands is approximately 70% higher with $^{225}$Ac-PSMA-617 than with $^{177}$Lu-PSMA-617, and red marrow dose 85% higher, respectively.

In clinical application, severe xerostomia became the dose-limiting toxicity if treatment activity exceeded 100 kBq/kg per cycle. At 100 kBq/kg, the duration of prostate-specific antigen decline was less than 4 months, but if therapy was repeated every 2 months patients experienced additive antitumor effects. Treatment activities of 50 kBq/kg were without toxicity but induced insufficient antitumor response in these high-tumor-burden patients. Remarkable antitumor activity by means of objective radiologic response or tumor marker decline was observed in 9 of 11 evaluable patients.

For advanced-stage patients, a treatment activity of 100 kBq/kg of $^{225}$Ac-PSMA-617 per cycle repeated every 8 weeks presents a reasonable trade-off between toxicity and biochemical response. This rationale is shown in FIG. 16.

The clinical dosimetry for $^{225}$Ac is cumbersome as discussed earlier. Even though dosimetry in clinical radionuclide therapy practice is mandatory according to EU guidelines, there are no tools available for clinical practice. One attempt has been shown in the literature using single-photon emission computed tomography (SPECT); as the $^{225}$Ac decay chain shows a noticeable gamma emission (440 keV, 25.9%; 218 keV, 11.4%). However, recommended low therapeutic activities (4-8 MBq) limit the clinical applicability of SPECT, although initial attempts for $^{225}$Ac imaging exist. Gosewisch et al. reported a mCRPC patient (65 years), whose imaging of the abdomen was performed at 24 h p. i. after therapeutic activity of 8.1 MBq $^{225}$Ac-PSMA I&T on a SPECT/CT camera (γ-energy 440 keV; window 20%).

Figure 17:
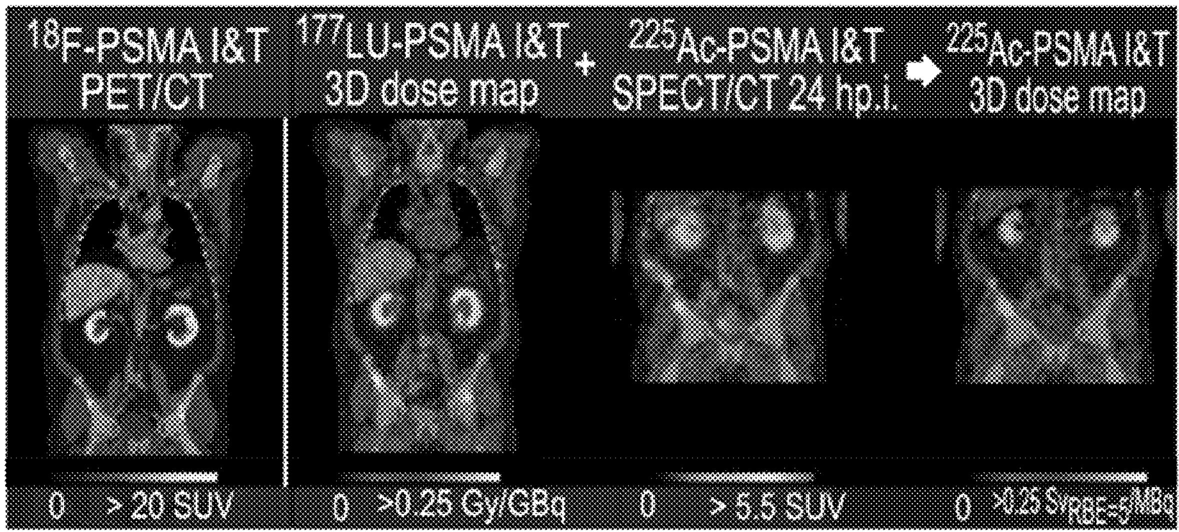
FIG. 17 depicts a summary of dosimetric γ-imaging for $^{225}$Ac-PSMA with Lu-177.

Final absorbed dose assessment was performed by Kratochwil et al. by combining the single $^{225}$Ac image with the effective half-life information determined from a previous $^{177}$Lu-PSMA I&T imaging sequence. This resulted in an absorbed dose of 0.18 and 0.17 $S_{V_{(RBE=5)}}$MBq for the left and right kidney, respectively, compared with 0.27 and 0.24 Gy/GBq for the preceding $^{177}$Lu cycle (6.2 GBq). A comparison with the pre-therapy $^{18}$F-PSMA I&T PET/CT demonstrates that $^{225}$Ac SPECT imaging for this patient was able to locate a small lesion in the right hip. The $^{225}$Ac-absorbed dose was determined as 0.26 $S_{V_{(RBE=5)}}$MBq, compared with 0.35 Gy/GBq for $^{177}$Lu-PSMA I&T. The imaging data is shown in FIG. 17.

III. Manufacturing Process and Formulation of $^{225}$Ac-PMSA I&T Injection

Optimal radiolabeling conditions were identified, improving the manufacturing process yield, and extending the drug product shelf life (radiochemical stability) through refining the final drug formulation of the $^{225}$Ac-PSMA I&T injection. In addition, the manufacturing process was scaled to a starting radioactivity of around 1 mCi.

Through the developed manufacturing process and formulation for $^{225}$Ac-PSMA I&T disclosed herein, improved conditions for radiolabeling and a new more stable formulation for the $^{225}$Ac-PSMA I&T injection were discovered. The overall process yield of around 90% was achieved in the improved process and the revised formulation demonstrated at least 120-hour radiochemical stability under the conditions tested. The improvements in the labeling process and formulation were confirmed for batch scale of around 1 mCi.

a. Radiolabeling

Optimization of the mole ratio of hydrochloric acid (HCl) to sodium ascorbate (Na-Asc.) was achieved through the study of radiolabeling of $^{225}$Ac-PSMA I&T in reaction mixtures containing different molar rations of HCl and Na-Asc. In a typical procedure, 6-8 MBq of $^{225}$Ac $(NO_3)_3$ dissolved in 1 ml of 0.04 M HCl was transferred to a reactor containing 110-120 μg of PSMA I&T in approximately 2 ml of sodium ascorbate solution at varying concentrations. The $^{225}$Ac $(NO_3)_3$ vial was then rinsed into the reactor with 1 ml of solution containing 100 μl of 0.04 M HCl and 900 μl of WFI (0.004 M HCl). Heating of the mixture was set to 110° C. for the radiolabeling and progress of the radiolabeling was monitored by taking samples from the reaction mixtures at different time points and performing a radio-TLC immediately after sample was taken.

Figure 18:
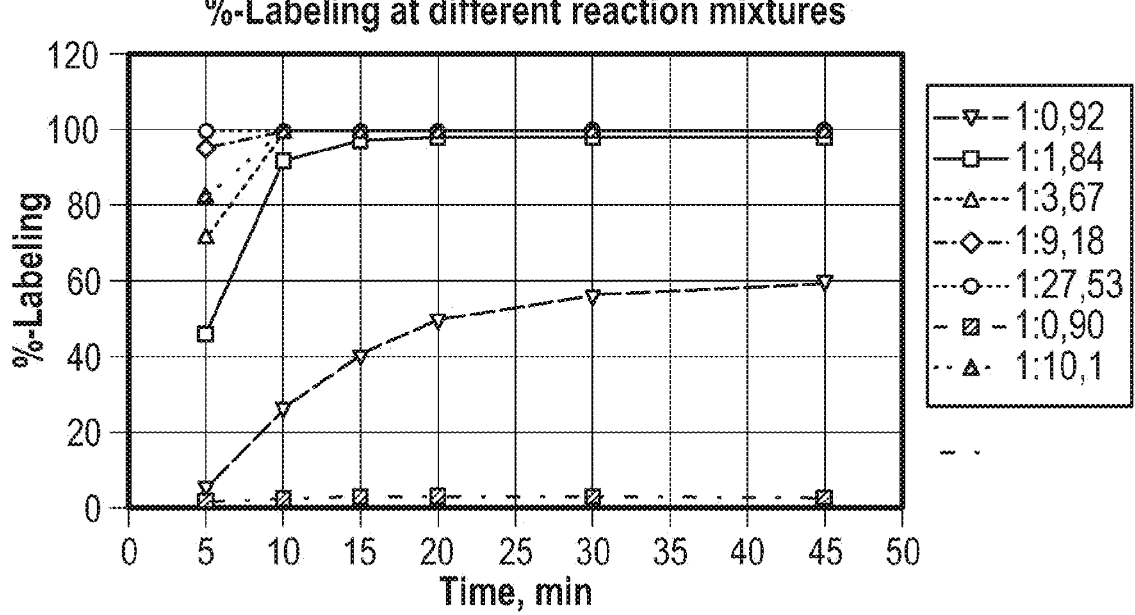
FIG. 18 depicts radiolabeling kinetics of $^{225}$Ac-PSMA I&T in different reaction mixtures.

The radio-TLC method was performed as follows: 5 μl or 10 μl of the sample was spotted onto the application line (1.5 cm from the lower edge of the plate) of a TLC plate (Merck Silica Gel 60 F254, plate size 20×100 mm). The TLC plate was developed in a TLC chamber using 0.1 M citric acid (adjusted to pH 5) as mobile phase. The plate was removed from the chamber when the eluent front reached 7.5 cm distance from the application line. The plates were analyzed with a radio-TLC scanner after secular equilibrium between $^{225}$Ac and daughter nuclides was reached (minimum of 7 hours). The results are provided in Table 10 and FIG. 18.

TABLE 10

Radiolabeling of $^{225}$Ac-PSMA I&T in reaction mixtures containing different molar ratio of hydrochloric acid and sodium ascorbate.

| Mole ratio | Sodium ascorbate | Labeling-% | | | | | | |
|---|---|---|---|---|---|---|---|---|
| HCl:Na-Asc. | content (% (w/w)) | 5 min | 10 min | 15 min | 20 min | 30 min | 45 min | 60 min |
| 1:0.90 | 0.94 | 1.32 | 2.39 | 3.02 | 3.03 | 3.02 | 2.72 | N/A |
| 1:0.92, | 0.09 | 5.52 | 25.93 | 40.27 | 49.70 | 55.90 | 58.97 | N/A |
| 1:1.84 | 0.19 | 45.95 | 91.88 | 97.09 | 98.04 | 98.15 | 98.04 | N/A |
| 1:3.67 | 0.38 | 71.54 | 91.88 | 97.09 | 99.44 | 99.82 | 99.50 | N/A |
| 1:9.18 | 0.94 | 95.13 | 99.56 | 99.76 | 99.79 | 99.71 | 99.82 | N/A |
| 1:10.1 * | 0.13 | 82.28 | 99.53 | 99.47 | 99.34 | 99.60 | 99.68 | N/A |
| 1:27.53 | 2.83 | 99.55 | 99.78 | 99.81 | 99.77 | 99.86 | 99.85 | N/A |
| 1:425 ** | 0.8 | 2.65 | 13.71 | N/A | N/A | 36.91 | 44.54 | 48.77 |

* Volume of the reaction mixture 3.24 ml,

** Volume of reaction mixture 7.14 ml.

Labeling percentage was found to improve by increasing the sodium ascorbate content in relation to hydrochloric acid. The molar ratio of 1:27.53 proved to be the most favorable of the conditions tested. However, even with a ratio of 1:3.67, the radiolabeling was nearly complete within 10 minutes. On the contrary, the highest molar ratio of 1:425 tested (not shown in FIG. 18) proved to be too high for radiolabeling, although in this case the effect of a larger reaction volume is not known.

After finding out the optimal conditions, tests were done in order to investigate if also the absolute mole amounts were significant for the labeling process in addition to the optimal molar ratio. The process at around 1:10 molar ratio conditions (row 5 in table 10) were shown to fail by adding extra hydrochloric acid to the reaction to reach 1:0.90 molar ratio (first row in Table 10). On the contrary, using the non-optimal conditions in the 1:0.92 molar ratio test (second row in Table 10), the radiolabeling process was shown to succeed by reducing the amount of hydrochloric acid in the reaction to achieve molar ratio of 1:10 (row 6 in table 10).

Due to the absence of buffering agent, the radiolabeling process was proven sensitive to small changes in the amount of hydrochloric acid. Hence the less hydrochloric acid in the reaction, the faster the radiolabeling will progress. However, at the same time it was discovered that a higher amount of hydrochloric acid is required for the dissolution and transfer of $^{225}$Ac $(NO_3)_3$ and lesser amounts can result in a poor overall yield.

Looking to the effect of HCl neutralization and temperature, radiolabeling of $^{225}$Ac-PSMA I&T was further studied in a reaction mixture containing 11.3 mg/ml of sodium ascorbate. In the reactions, hydrochloric acid was neutralized by adding equivalent mole amount of sodium hydroxide prior to the heating of the mixture. To study the effect of temperature, the radiolabeling was performed at temperature set points of 110° C., 75° C. and 23° C. (no heating).

In the procedure, around 8 MBq of $^{225}$Ac $(NO_3)_3$, dissolved in 0.04 M HCl, was transferred to a reactor containing 110-120 μg of PSMA I&T dissolved in 1.08 ml of 45.2 mg/ml sodium ascorbate. 225Ac $(NO_3)_3$ vial was then rinsed in a reactor with 1 ml of 0.004 M HCl. Hydrochloric acid transferred into the reactor was then neutralized by adding 1 ml of 0.04 M NaOH solution to the reactor prior to the start of heating.

Progress of the radiolabeling was monitored by the radio-TLC, as described previously, at different time points. The results are provided in Table 11 and FIG. 19.

TABLE 11

Radiolabeling of $^{225}$Ac-PSMA I&T in a reaction mixture neutralized with NaOH at different temperature set points.

| Temperature | Labeling-% | | | | | |
|---|---|---|---|---|---|---|
| Set Point (° C.) | 0 min | 3 min | 6 min | 9 min | 12 min | 15 min |
| 110 | 9.93 | 95.24 | 99.62 | 100.0 | 100.0 | 100.0 |
| 75 | 8.69 | 49.01 | 97.73 | 99.37 | 99.57 | 99.46 |
| 23 | 5.09 | 7.32 | 7.69 | 10.62 | 12.23 | 13.26 |

The results show that temperature is an important factor in the reaction. The fastest labeling was achieved at the highest temperature set point where radiolabeling was complete after only 9 minutes. At set point of 75° C. the radiolabeling was slower, but it was still nearly complete in under 9 minutes. Without heating, the reaction was not found to proceed to completion within 15 minutes. Therefore, the results suggest that temperature set point of at least 75° C. is required to ensure reaction is complete in a set time.

Furthermore, the results provided in Tables 10 and 11 above allowed for length of heating time of the reaction mixture to be assessed. The reaction was found to be complete in well under 15 minutes near the optimal conditions. It was therefore considered unnecessary to extend the heating time from 15 minutes. At the same time, reduction of the heating time to less than 15 minutes was not carried out since the benefits of saving time were considered insignificant compared to the risks of incomplete labeling process.

b. Purification

Regarding the purification step of the manufacturing process, the effect of C18 SPE purification was studied simultaneously with the radiolabeling studies disclosed above. After the last radio-TLC samples were taken from the reaction mixtures, the mixtures were passed through a C18 cartridge, and the cartridge was rinsed with WFI. $^{225}$Ac-PSMA I&T was eluted from the cartridge using 1.5 ml of 50% ethanol solution and diluted to a desired volume and composition of final formulation. The radio-TLC method was then performed from the final formulation to determine the radiochemical purity of $^{225}$Ac-PSMA I&T.

The purity of $^{225}$Ac-PSMA I&T in the final formulation was compared to the purity in the sample taken at the end of radiolabeling. The results are provided in Table 12 below.

TABLE 12

Effect of C18 Sep Pak purification on the radiochemical purity of $^{225}$Ac-PSMA I&T.

| # | RCP. Prior to purification (%) | RCP. After purification (%) |
|---|---|---|
| 1 | 47.77 | 87.14 |
| 2 | 98.04 | 96.78 |
| 3 | 99.50 | 97.87 |
| 4 | 58.97 | 93.11 |
| 5 | 99.82 | 98.67 |
| 6 | 99.85 | 99.30 |
| 7 | 2.72 | 60.91 |
| 8 | 99.68 | 98.14 |

The results suggest that contrary to what was expected, the C18 SPE purification step can in some cases reduce the radiochemical purity of the final product (runs 2, 3, 5, 6 and 8 in Table 12). On the other hand, when the radiolabeling was clearly inadequate, the purification step was found to improve the radiochemical purity of the final product (runs 1 and 7 in Table 12). However, even then, the radiochemical purity remained relatively low and desirable radiochemical purity was not achieved.

c. Formulation Excipients Screening

In order to extend the shelf life of the product, stability (radiochemical purity) of $^{225}$Ac-PSMA I&T was also investigated in various formulation compositions. In a typical radiolabeling procedure, the reaction mixtures were passed through a C18 SPE cartridge and the cartridge was rinsed with WFI. $^{225}$Ac-PSMA I&T was eluted from the cartridge using 1.5 ml of 50% ethanol solution. The concentrated solution was divided into three 0.5 ml fractions, each of which were then diluted to desired formulation composition obtaining a total volume of 3 ml for each sample.

The formulations with different ascorbic acid concentrations were prepared from commercial ascorbic acid solution (ASCOR L injection, McGuff) containing EDTA as a preservative. In other formulations 9 mg/ml sodium chloride injection or WFI was used.

For the pH 4.5 and 7 formulations, pH of the ascorbic acid solution was adjusted prior to dilution.

The $^{225}$Ac-PSMA I&T formulations prepared were stored at room temperature (23° C.). Radiochemical purity of $^{225}$Ac-PSMA I&T was determined at different time points by the radio-TLC method. Results are provided in Table 13 and FIG. 20.

TABLE 13

Radiochemical purity of $^{225}$Ac-PSMA I&T by the radio-TLC method at different formulatic compositions

| Formulation composition | RAC (kBq/ml) | RCP (%) Initial | 24 h | 48 h | 72 h | 96 h | 120 h | 168 h |
|---|---|---|---|---|---|---|---|---|
| Ascorbic Acid 42.5 mg/ml 7.5% (v/v) EtOH (pH = 5.5) | 526 | 96.8 | 97.0 | — | 96.4 | — | 96.4 | 95.5 |
| Ascorbic Acid 42.5 mg/ml 7.5% (v/v) EtOH (pH 4.5) | 526 | 96.8 | 94.4 | — | 90.2 | — | 86.3 | 82.7 |
| Ascorbic Acid 42.5 mg/ml 7.5% (v/v) EtOH (pH 7.0) | 526 | 96.8 | 96.3 | — | 96.1 | — | 96.0 | 95.7 |
| Sodium Chloride 9 mg/ml 7.5% (v/v) EtOH | 227 | 94.8 | 93.5 | — | 93.2 | — | 92.8 | 93.1 |
| WFI 7.5% (v/v) EtOH | 227 | 94.8 | 94.4 | — | 91.9 | — | 88.9 | 88.2 |

TABLE 13-continued

Radiochemical purity of $^{225}$Ac-PSMA I&T by the radio-TLC method at different formulatic compositions

| Formulation composition | RAC (kBq/ml) | RCP (%) Initial | 24 h | 48 h | 72 h | 96 h | 120 h | 168 h |
|---|---|---|---|---|---|---|---|---|
| Ascorbic Acid 21 mg/ml 7.5% (v/v) EtOH | 227 | 94.8 | 94.1 | — | 93.9 | — | 93.8 | 93.8 |

The results show that the stability is significantly reduced at pH 4.5, but there was no difference in stability in the pH range from about 5.5 to about 7.0. An illustrative graph is shown in FIG. 20.

The results also showed signs of lower concentration of ascorbic acid being beneficial for the stability, while complete absence of it seemed to decrease stability. Suggesting ideal concentration of ascorbic acid being somewhere in the range of 0 mg/ml-42.5 mg/ml. However, the difference was not found significant.

d. Formulation Screening at 40° C.

Due to the lack of significant differences in the stability at 23° C., the test series was renewed at elevated temperature (40° C.), which was known to have a negative impact on the stability. In the series, the effect of individual and possible formulation components was investigated more comprehensively.

The formulations containing ascorbic acid were prepared by using the ASCOR L injection, containing EDTA as a preservative. The other formulations were prepared from sodium ascorbate.

After radiolabeling, the 225Ac-PSMA I&T was separated from the reaction mixture using the C18 cartridge procedure as outlined above, or alternatively the reaction mixtures were transferred directly to final vial after radiolabeling. Finally, the product solution was divided in fractions and each fraction was diluted to a desired formulation. Final volume of the samples prepared were around 3 ml for all samples.

Radioactivity concentration of each sample was measured using HPGe gamma spectrometer. Measurement samples were prepared by pipetting 20 µl of product solution into a vial containing 980 µl of water. Radioactive concentration was calculated from the results on the day of production. Radioactivity concentration of each product sample on the day of production was calculated based on the measurement results.

Radiochemical purity of $^{225}$Ac-PSMA I&T, in relation to unbound $^{225}$Ac, was determined at different time points by the radio-TLC method as described previously. The results are provided and discussed below.

Figure 21:
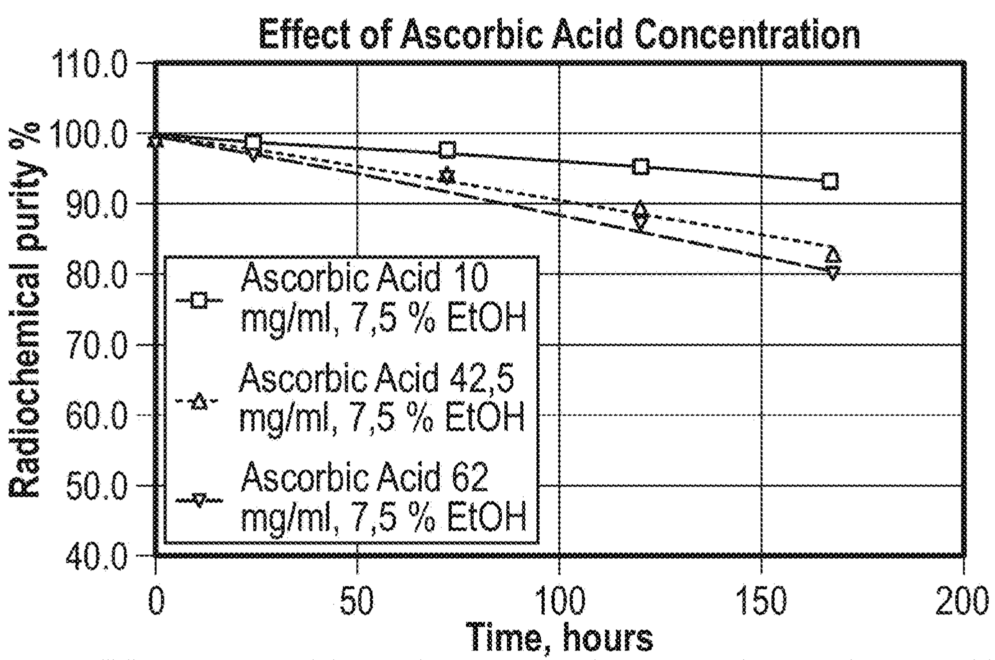
FIG. 21 depicts the effect of ascorbic acid concentration on $^{225}$Ac-PSMA I&T stability.

Table 14 and FIG. 21 show the results of formulations that contained ascorbic acid in three different concentrations.

TABLE 14

Radiochemical stability of $^{225}$Ac-PSMA I&T by the radio-TLC method in different ascorbic acid formulation compositions stored at 40° C.

| Formulation composition | RAC (kBq/ml) | RCP (%) Initial | 24 h | 48 h | 72 h | 96 h | 120 h | 168 h |
|---|---|---|---|---|---|---|---|---|
| Ascorbic Acid 10 mg/ml 7.5% (v/v) EtOH | 657 | 98.7 | 98.5 | — | 97.5 | — | 95.2 | 92.7 |
| Ascorbic Acid 42.5 mg/ml 7.5% (v/v) EtOH | 702 | 98.7 | 97.4 | — | 94.1 | — | 88.9 | 83.0 |
| Ascorbic Acid 62 mg/ml 7.5% (v/v) EtOH | 748 | 98.7 | 97.0 | — | 93.5 | — | 87.4 | 78.4 |

As seen from the results, 10 mg/ml ascorbic acid formulation showed higher radiochemical stability compared to the other two formulations containing higher concentrations of ascorbic acid. In some embodiments, the compositions described herein comprise about 0 mg/ml to about 100 mg/ml ascorbic acid, about 5 mg/ml to about 100 mg/ml ascorbic acid, about 5 mg/ml to about 90 mg/ml ascorbic acid, about 5 mg/ml to about 80 mg/ml ascorbic acid, about 5 mg/ml to about 70 mg/ml ascorbic acid, about 5 mg/ml to about 60 mg/ml ascorbic acid, about 5 mg/ml to about 50 mg/ml ascorbic acid, about 5 mg/ml to about 40 mg/ml ascorbic acid, about 5 mg/ml to about 30 mg/ml ascorbic acid, about 5 mg/ml to about 20 mg/ml ascorbic acid, about 5 mg/ml to about 10 mg/ml ascorbic acid, about 10 mg/ml to about 100 mg/ml ascorbic acid, about 10 mg/ml to about 90 mg/ml ascorbic acid, about 10 mg/ml to about 80 mg/ml ascorbic acid, about 10 mg/ml to about 70 mg/ml ascorbic acid, about 10 mg/ml to about 60 mg/ml ascorbic acid, about 10 mg/ml to about 50 mg/ml ascorbic acid, about 10 mg/ml to about 40 mg/ml ascorbic acid, about 10 mg/ml to about 30 mg/ml ascorbic acid, about 10 mg/ml to about 20 mg/ml ascorbic acid, about 15 mg/ml to about 100 mg/ml ascorbic acid, about 15 mg/ml to about 90 mg/ml ascorbic acid, about 15 mg/ml to about 80 mg/ml ascorbic acid, about 15 mg/ml to about 70 mg/ml ascorbic acid, about 15 mg/ml to about 60 mg/ml ascorbic acid, about 15 mg/ml to about 50 mg/ml ascorbic acid, about 15 mg/ml to about 45 mg/ml ascorbic acid, about 15 mg/ml to about 40 mg/ml ascorbic acid, about 15 mg/ml to about 30 mg/ml ascorbic acid, about 15 mg/ml to about 20 mg/ml ascorbic acid, about 20 mg/ml to about 100 mg/ml ascorbic acid, about 20 mg/ml to about 90 mg/ml ascorbic acid, about 20 mg/ml to about 80 mg/ml ascorbic acid, about 20 mg/ml to about 70 mg/ml ascorbic acid, about 20 mg/ml to about 60 mg/ml ascorbic acid, about 20 mg/ml to about 50 mg/ml ascorbic acid, about 20 mg/ml to about 40 mg/ml ascorbic acid, about 20 mg/ml to about 30 mg/ml ascorbic acid, about 20 mg/ml to about 25 mg/ml ascorbic acid, about 25 mg/ml to about 100 mg/ml ascorbic acid, about 25 mg/ml to about 90 mg/ml ascorbic acid, about 25 mg/ml to about 80 mg/ml ascorbic acid, about 25 mg/ml to about 70 mg/ml ascorbic acid, about 25 mg/ml to about 60 mg/ml ascorbic acid, about 25 mg/ml to about 50 mg/ml ascorbic acid, about 25 mg/ml to about 40 mg/ml ascorbic acid, about 25 mg/ml to about 30 mg/ml ascorbic acid, about 25 mg/ml to about 70 mg/ml ascorbic acid, about 30 mg/ml to about 100 mg/ml ascorbic acid, about 30 mg/ml to about 90 mg/ml ascorbic acid, about 30 mg/ml to about 80 mg/ml ascorbic acid, about 30 mg/ml to about 70 mg/ml ascorbic acid, about 30 mg/ml to about 60 mg/ml ascorbic acid, or about 30 mg/ml to about 50 mg/ml ascorbic acid.

Figure 22:
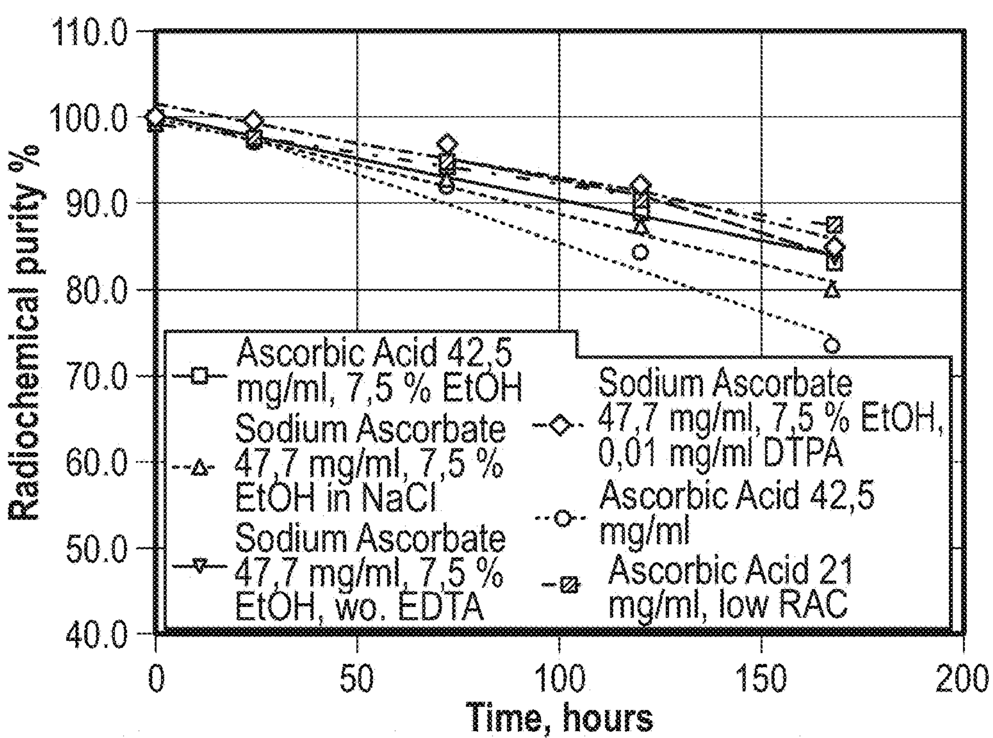
FIG. 22 depicts a summary of the formulation composition findings for $^{225}$Ac-PSMA I&T.

To examine the effect of different excipients more extensively, $^{225}$Ac-PSMA I&T stability in different formulation compositions was investigated. The different formulation compositions and results are provided in Table 15 and FIG. 22. The results of 42.5 mg/ml ascorbic acid, 7.5% ethanol formulation from Table 14 are also added to the Table 15 and FIG. 22 to allow comparison between all results. The formulation represents the previous formulation in the $^{225}$Ac-PSMA I&T manufacturing process (baseline).

TABLE 15

Screening of different formulation compositions at 40° C.

| Formulation composition | RAC (kBq/ml) | RCP (%) Initial | 24 h | 48 h | 72 h | 96 h | 120 h | 168 h |
|---|---|---|---|---|---|---|---|---|
| Ascorbic Acid 42.5 mg/ml 7.5% (v/v) EtOH (baseline) | 702 | 98.7 | 97.4 | — | 94.1 | — | 88.9 | 83.0 |
| Sodium Ascorbate 47.7 mg/ml 7.5% (v/v) EtOH in 9 mg/ml NaCl | 523 | 99.7 | 99.1 | — | 96.7 | — | 91.3 | 84.2 |
| Sodium Ascorbate 47.7 mg/ml 7.5% (v/v) EtOH wo. EDTA | 650 | 99.7 | 99.1 | — | 96.7 | — | 91.4 | 84.1 |
| Sodium Ascorbate 47.7 mg/ml 7.5% (v/v) EtOH 0.01 mg/ml DTPA | 636 | 99.7 | 99.3 | — | 96.6 | — | 92.0 | 84.5 |
| Ascorbic Acid 42.5 mg/ml high RAC | 769 | 99.1 | 97.1 | — | 91.9 | — | 84.2 | 72.2 |
| Ascorbic Acid 21 mg/ml low RAC | 418 | 99.1 | 97.4 | — | 94.6 | — | 90.1 | 87.3 |
| Ascorbic Acid 42.5 mg/ml low RAC | 364 | 99.1 | 96.9 | — | 92.4 | — | 87.3 | 80.5 |

The results show that the ascorbic acid solution without ethanol had the lowest stability, and in line with previous results, the lower ascorbic acid concentration had an improving effect on stability. On the other hand, no significant effect was observed for NaCl, EDTA or DTPA in the formulation.

Figure 23:
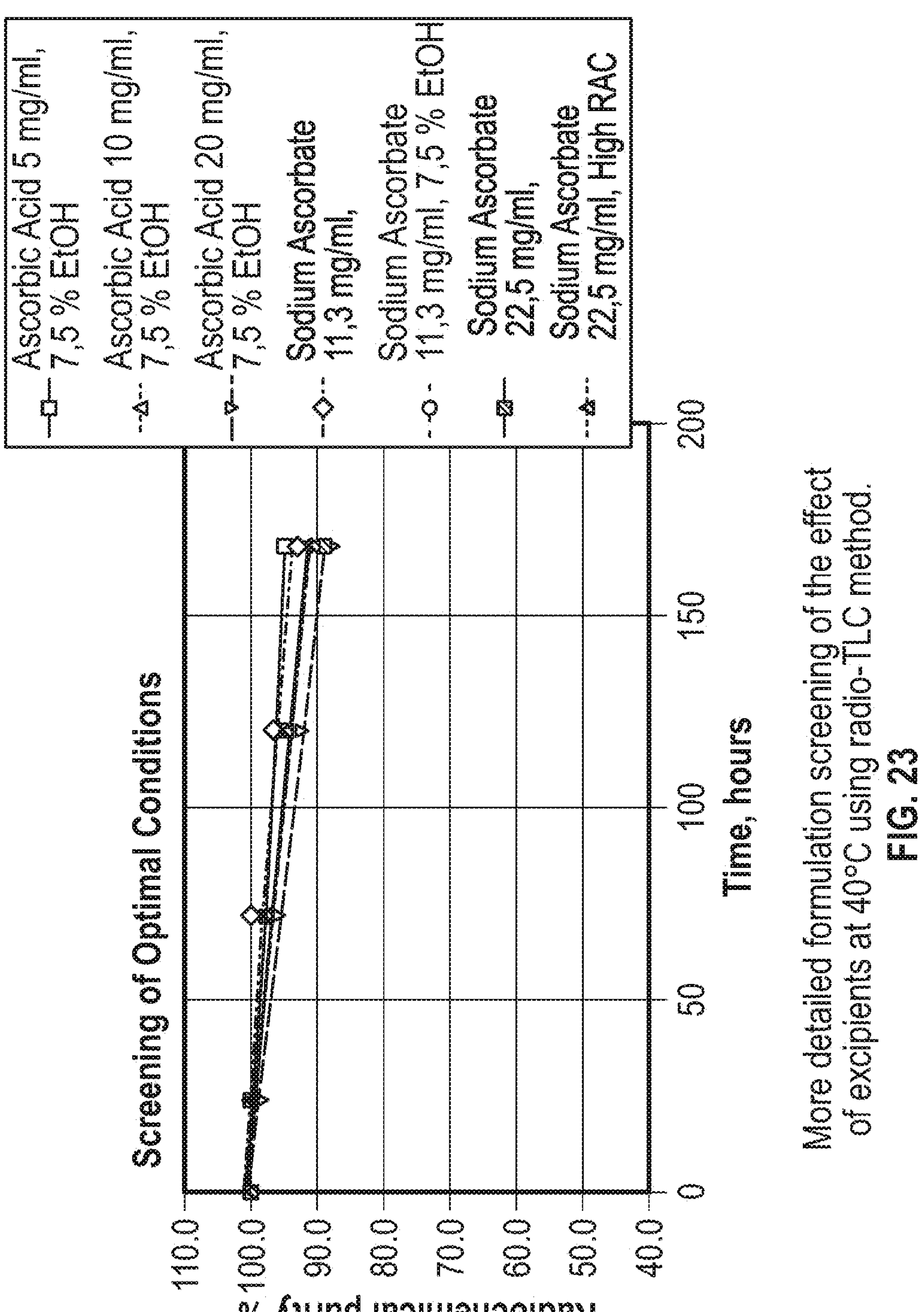
FIG. 23 depicts a detailed summary of the formulation composition findings for $^{225}$Ac-PSMA I&T.

Next, the effect of the concentration of ascorbic acid and sodium ascorbate was investigated and compared more thoroughly near the favorable concentration area. Also, the potential stability enhancing effect of ethanol was further investigated near the optimal ascorbic acid concentration. In addition, the effect of radioactivity concentration on the stability of $^{225}$Ac-PSMA I&T was investigated. The results are shown in Table 16 and FIG. 23.

TABLE 16

More detailed screening of the effect of excipients at 40° C.

| Formulation composition | RAC (kBq/ml) | RCP (%) Initial | 24 h | 48 h | 72 h | 96 h | 120 h | 168 h |
|---|---|---|---|---|---|---|---|---|
| Ascorbic Acid 5 mg/ml 7.5% (v/v) EtOH | 758 | — | 99.1 | — | 98.2 | — | 96.2 | 95.0 |

TABLE 16-continued

More detailed screening of the effect of excipients at 40° C.

| Formulation composition | RAC (kBq/ml) | RCP (%) Initial | 24 h | 48 h | 72 h | 96 h | 120 h | 168 h |
|---|---|---|---|---|---|---|---|---|
| Ascorbic Acid 10 mg/ml 7.5% (v/v) EtOH | 930 | — | 98.8 | — | 97.0 | — | 94.3 | 91.3 |
| Ascorbic Acid 20 mg/ml 7.5% (v/v) EtOH | 967 | — | 98.7 | 97.1 | 96.3 | — | 92.7 | 87.9 |
| Sodium Ascorbate 11.3 mg/ml | 534 | 100 | 100 | — | 100 | — | 96.4 | 92.6 |
| Sodium Ascorbate 11.3 mg/ml 7.5% (v/v) EtOH | 523 | — | 100 | — | 100 | — | 96.7 | 93.0 |
| Sodium Ascorbate 22.5 mg/ml | 514 | — | 100 | — | 97.7 | — | 95.7 | 89.2 |
| Sodium Ascorbate 22.5 mg/ml high RAC | 1033 | — | 100 | — | 97.5 | — | 94.5 | 90.5 |

The best stability of $^{225}$Ac-PSMA I&T was observed in the 5 mg/ml ascorbic acid, 7.5% ethanol formulation. However, the differences between the formulations were relatively small and the stability of $^{225}$Ac-PSMA I&T in both 11.3 mg/ml sodium ascorbate formulations, with or without ethanol, was found nearly as good as in the 5 mg/ml ascorbic acid, 7.5% ethanol formulation. The results also suggest that radioactivity concentration in the range 514-1033 kBq/ml does not have a significant effect on the stability of $^{225}$Ac-PSMA I&T in 22.5 mg/ml sodium ascorbate formulation.

e. Metal Scavenger

Due to the process change of removing C-18 purification, ascorbic acid solution containing metal scavenger (EDTA) was changed into pure sodium ascorbate coming directly from the labeling process. The use of metal scavenger (DTPA) was considered as an alternative to EDTA, and it was investigated in 11.3 mg/ml sodium ascorbate formulation.

Figure 24:
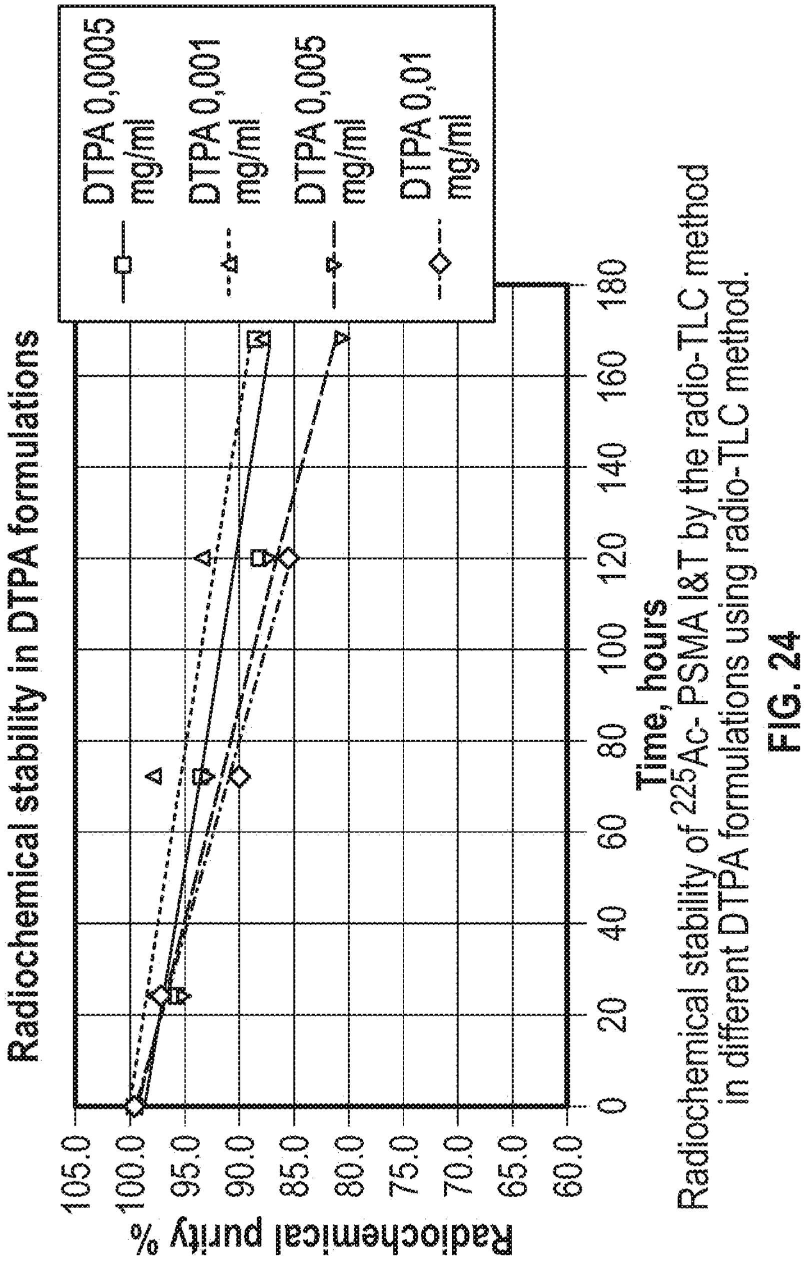
FIG. 24 depicts radiochemical stability of $^{225}$Ac-PSMA I&T in various DTPA formulations.

After radiolabeling the $^{225}$Ac-PSMA I&T reaction mixture was transferred to a final vial. The mixture was then divided into four samples which were diluted with suitable amount WFI and DTPA solution to achieve concentrations of 0.0005 mg/ml, 0.001 mg/ml, 0.005 mg/ml, and 0.01 mg/ml of DTPA in the final formulations. The total volume of samples was 3.3 ml and the measured radioactive concentrations was around 450 kBq/ml in all samples. The samples were kept at 40° C. Purity of $^{225}$Ac-PSMA I&T was determined at different time points by the radio-TLC method. Results are provided in Table 17 and FIG. 24.

TABLE 17

Radiochemical stability of $^{225}$Ac-PSMA I&T by the radio-TLC method in formulations containing different concentration of DTPA.

| DTPA conc. in formulation (mg/ml) | RAC (kBq/ml) | RCP (%) Initial | 24 h | 48 h | 72 h | 96 h | 120 h | 168 h |
|---|---|---|---|---|---|---|---|---|
| 0.0005 | 462 | 99.6 | 95.7 | — | 93.5 | — | 88.1 | 88.4 |
| 0.001 | 520 | 99.6 | 97.6 | — | 93.2 | — | 87.6 | 78.5 |
| 0.005 | 479 | 99.6 | 95.3 | — | 93.0 | — | 87.4 | 80.5 |
| 0.01 | 483 | 99.6 | 97.1 | — | 90.1 | — | 85.5 | — |

Based on the results, DTPA was found to significantly reduce the stability of the $^{225}$Ac-PSMA I&T. A search of literature suggested that DTPA may not form stable chelates with $^{225}Ac^{3\pm}$, so it is unlikely that DTPA would be competing in coordination of $^{225}Ac^{3\pm}$ with DOTAGA. Instead, the decreased stability could be due to some other mechanism in which DTPA is involved that results in a weaker complex of $^{225}$Ac-DOTAGA. Therefore, in the presence of DTPA radiochemical stability of $^{225}$Ac-PSMA I&T is reduced.

As a conclusion, adding DTPA in the formulation was not found beneficial for the stability of $^{225}$Ac-PSMA I&T and it was decided not to include it in the formulation. In addition, the excess PSMA I&T itself can function as a metal scavenger in the formulation, which in some embodiments, can make the addition of other metal scavengers not essential.

f. Sodium Ascorbate Concentration Range

Figure 25:
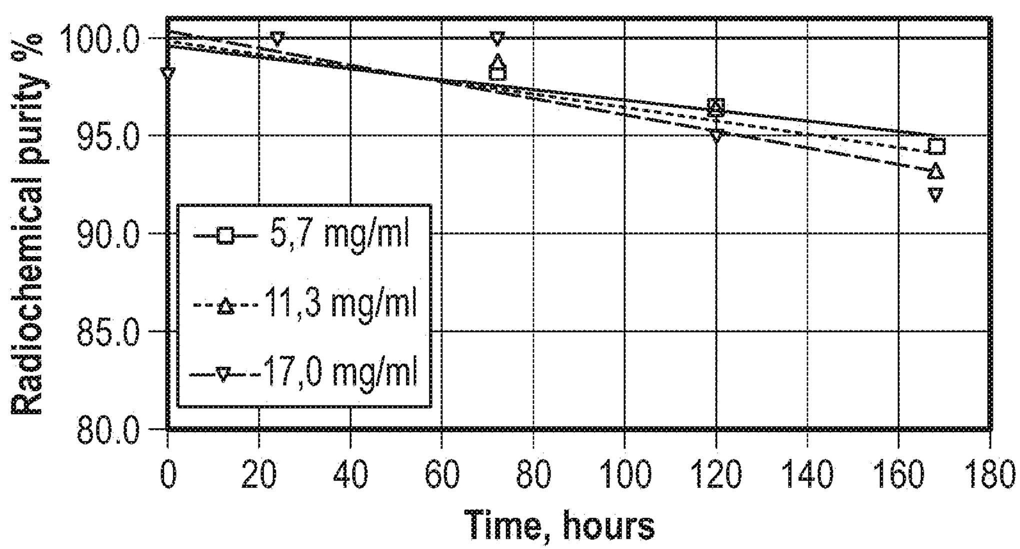
FIG. 25 depicts radiochemical stability of $^{225}$Ac-PSMA I&T in formulations containing various concentrations of sodium ascorbate.

To determine suitable range of sodium ascorbate concentration in the formulation, three formulation samples of 3.3 ml volume were prepared from $^{225}$Ac-PSMA I&T reaction mixture containing 5.7 mg/ml, 11.3 mg/ml, and 17.0 mg/ml of sodium ascorbate. The samples were prepared immediately after radiolabeling by diluting with suitable amount of WFI and sodium ascorbate. Radioactive concentration of the samples was measured using the gamma spectrometer method as described previously. The samples were stored at 40° C. and purity of $^{225}$Ac-PSMA I&T was determined at different time points by the radio-TLC method. The results are provided in table 18 and FIG. 25 below.

Figure 26:
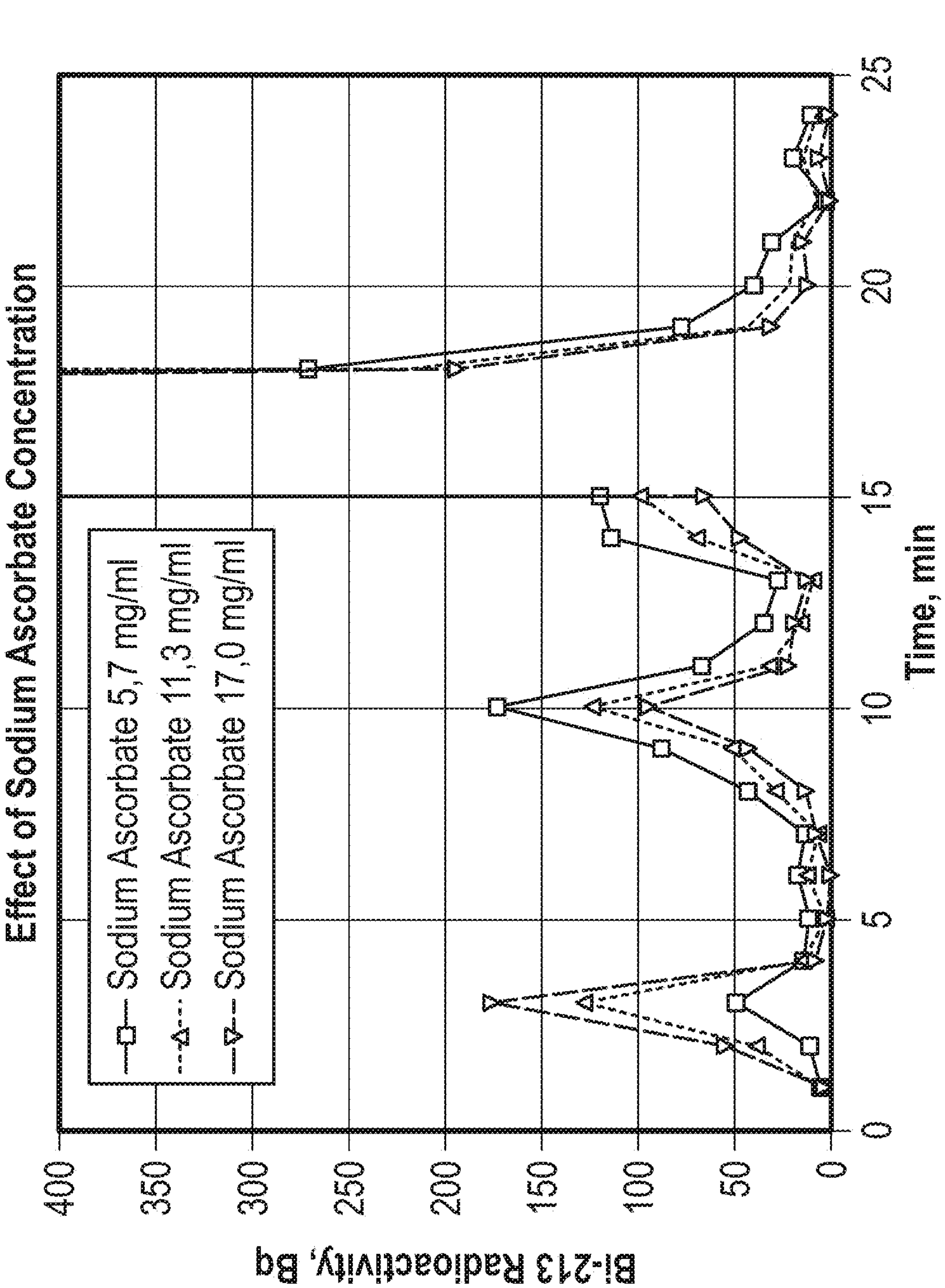
FIG. 26 depicts the effect of sodium ascorbate concentration on the radiochemical purity of $^{225}$Ac-PSMA I&T.

In addition to the radio-TLC method, radiochemical purity of $^{225}$Ac-PSMA I&T at 120-hour time point was examined by HPLC fraction collection method, FIG. 26. The fraction collection method was performed as follows:

Column: Waters XBridge Peptide BEH C18 (3.5 μm, 150 mm×4.6 mm), mobile phase A: 50 mM $NH_4OAc$, mobile phase B: ACN, flow rate: 1 ml/min, temperature 23° C., injection volume: 80 μl, wavelength: 280 nm and collection time: 24 min.

The HPLC program was as follows: 0 min-2 min, hold 9% B Conc.; 2 min-22 min, 9% to 20% B Conc.; 22 min-23 min, 20% to 80% B Conc.; 23 min-28 min, hold 80% B Conc.; 28 min-29 min, 80% to 9% B Conc.; 29 min-33 min, hold 9% B Conc.

The 0 min-24 min volume was collected into 1 ml fractions. Radioactivity in each fraction was measured using HPGe gamma spectrometer after secular equilibrium was reached between $^{213}$Bi and $^{225}$Ac. Radiochemical purity was calculated based on the sum of radioactivity in fractions containing $^{225}$Ac-PSMA I&T in relation to total radioactivity in all fractions.

The method allowed for the first-time detection of radiolysis fragment of $^{225}$Ac-PSMA I&T, that is not visible in the TLC-method. The results of HPLC-fractions are shown in FIG. 26 and the RCP results are shown in Table 19.

TABLE 18

Radiochemical stability of $^{225}$Ac-PSMA I&T determined by the radio-TLC method in formulations containing different concentrations of sodium ascorbate.

| Sodium ascorbate in formulation | RCP (%) | | | | | | |
|---|---|---|---|---|---|---|---|
| (mg/ml) | Initial | 24 h | 48 h | 72 h | 96 h | 120 h | 168 h |
| 5.7 | 98.2 | 100 | — | 98.3 | — | 96.5 | 94.4 |
| 11.3 | 98.2 | 100 | — | 98.7 | — | 96.3 | 93.1 |
| 17.0 | 98.2 | 100 | — | 100 | — | 95.0 | 92.0 |

TABLE 19

Radiochemical stability of $^{225}$Ac-PSMA I&T determined by the HPLC-fraction collecting method in formulations containing different concentrations of sodium ascorbate at 120-hour time point.

| Sodium ascorbate in formulation (mg/ml) | Free $^{225}$Ac (%) | Radiolysis fragment of $^{225}$Ac-PSMA I&T (%) | RCP of $^{225}$Ac-PSMA I&T (%) | Background/ tail (%) |
|---|---|---|---|---|
| 5.7 | 0.5 | 2.1 | 96.5 | 0.9 |
| 11.3 | 1.0 | 1.2 | 97.3 | 0.5 |
| 17.0 | 1.2 | 1.0 | 97.4 | 0.4 |

The measured radioactivity concentration of the samples was around 300 kBq/ml. The radiochemical stability of $^{225}$Ac-PSMA I&T in relation to unbound $^{225}$Ac was found to be 95% or higher in all formulations tested.

Based on the HPLC results shown in FIG. 26, in 5.7 mg/ml sodium ascorbate formulation the amount of unbound $^{225}$Ac was the lowest, but at the same time the relative amount of unknown radiochemical impurity eluting at around 10 minutes was highest. In 17 mg/ml sodium ascorbate formulation, the results were the opposite.

The results show that the 11.3 mg/ml sodium ascorbate formulation is optimal for the radiochemical stability of $^{225}$Ac-PSMA I&T. Taking into account the radiochemical impurity found in the HPLC run, the sodium ascorbate concentration range 5-17 mg/ml is considered optimal in terms of the stability of $^{225}$Ac-PSMA I&T.

g. Process Scale

Figure 27:
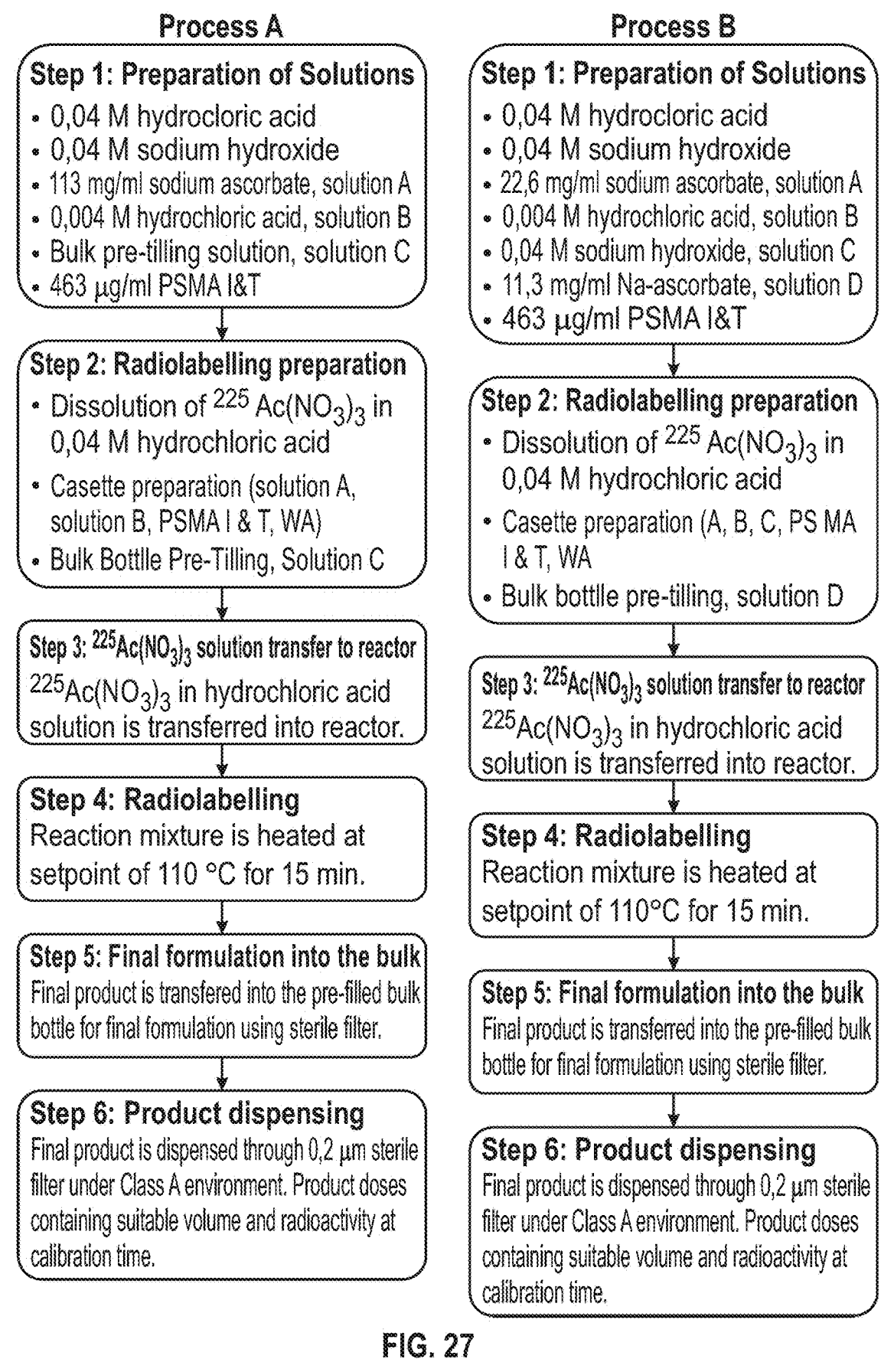

Two embodiments for the manufacturing process of $^{225}$Ac-PSMA I&T injection were considered based upon the results of the previous sections and are disclosed herein. Both embodiments, referred to as process A and process B, and their key steps are outlined in FIG. 27.

In process A, the sodium ascorbate concentration in the radiolabeling solution is around 56.5 mg/ml in order to obtain 11.3 mg/ml sodium ascorbate concentration in the final formulation of volume 20 ml. 1 ml of 0.04 M NaOH solution is added to the final formulation to neutralize 0.04 M HCl in the solution transferred from the reactor.

In process B, radiolabeling is performed in 11.3 mg/ml sodium ascorbate solution and the 0.04 M HCl is neutralized by adding 1 ml of 0.04 M NaOH solution into the reactor prior to labeling. The final formulation in process B is prepared to an intended radioactivity concentration by diluting with 11.3 mg/ml sodium ascorbate solution.

To compare the processes, $^{225}$Ac-PSMA I&T injection was prepared at around 1 mCi scale using both processes. The results are provided in Table 20 below. The final formulations were prepared to a total volume of 63.6 ml in process A and 31.8 ml in process B. In process B, final formulation radioactivity concentration was intentionally prepared twice as high compared to process A to study its effect on the initial radiochemical purity of $^{225}$Ac-PSMA I&T. Radioactivity concentrations were measured using HPGe gamma spectrometer method as described above. Radioactivity concentration was 468 kBq/ml in process A and 969 kBq/ml in process B.

Process yields (%) were calculated for both processes based on the initial radioactivity of $^{225}Ac(NO_3)_3$ used in the process and the final radioactivity concentrations of the product. The calculated yield in process A was 92.6% and in process B was 96.0%.

The final product solutions were dispensed to 15 ml (process A) or 7 ml (process B) samples representing a typical intended dose volume. 20 ml vials were used for samples in the process A and 15 ml vials in the process B. The samples were stored at following temperatures: 5° C., 22.5° C., 32.5° C., and 40° C.

The purity of $^{225}$Ac-PSMA I&T samples was analyzed by the radio-TLC and HPLC fraction collection methods described previously at different time points.

Figure 28:
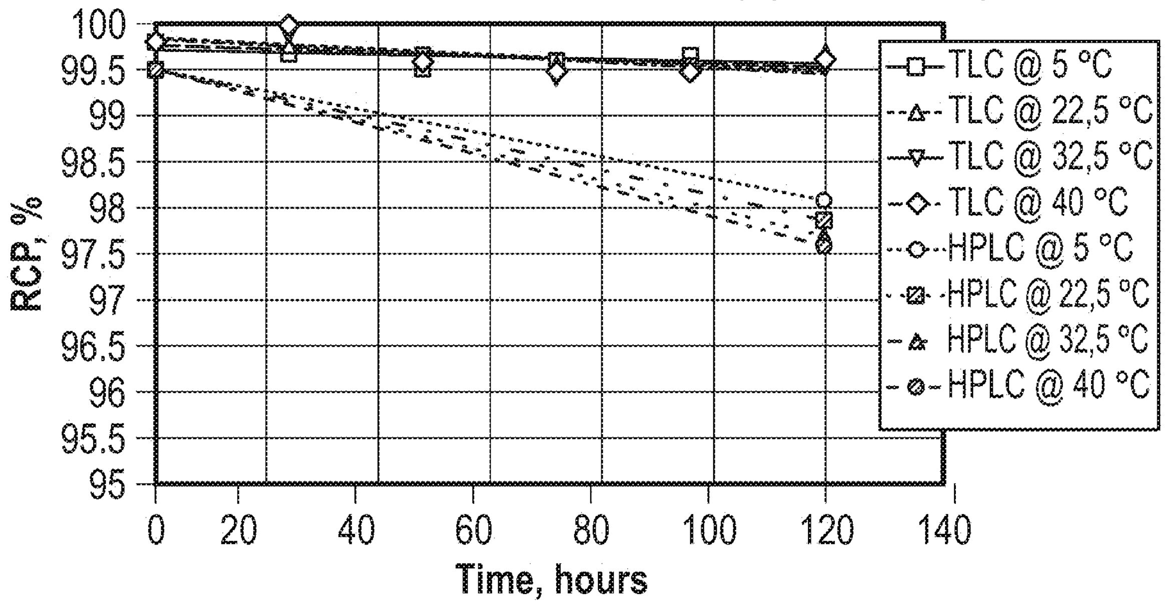
FIG. 28 depicts the radiochemical purity of $^{225}$Ac-PSMA I&T prepared using Process A.
Figure 29:
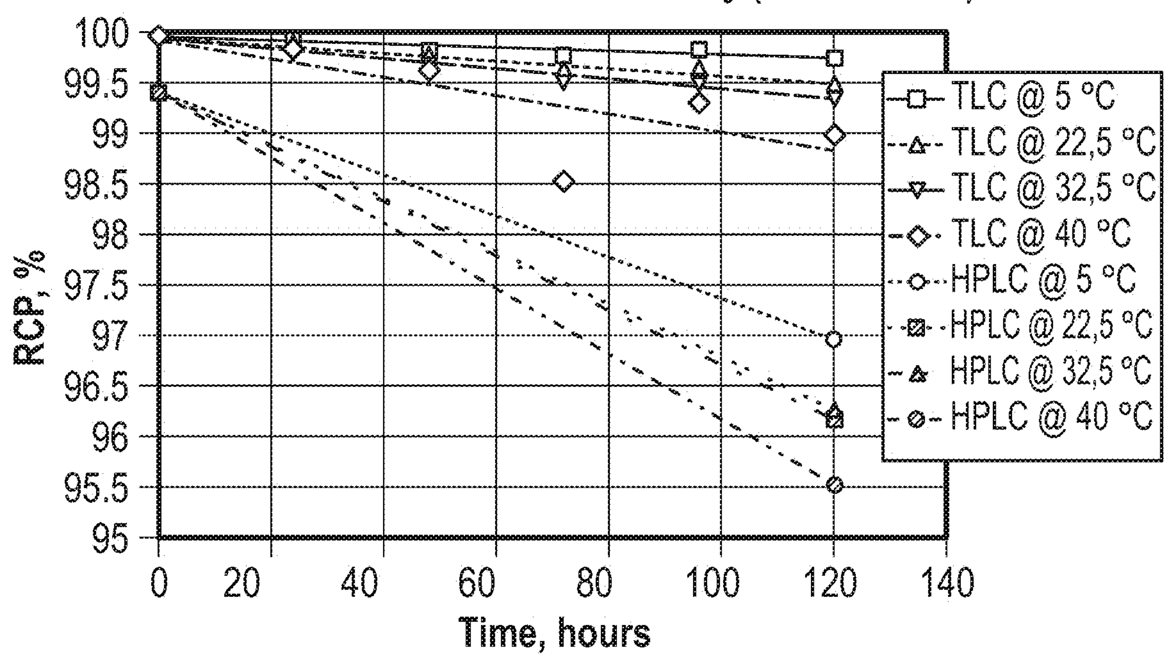
FIG. 29 depicts the radiochemical purity of $^{225}$Ac-PSMA I&T prepared using Process B.
Figure 30:
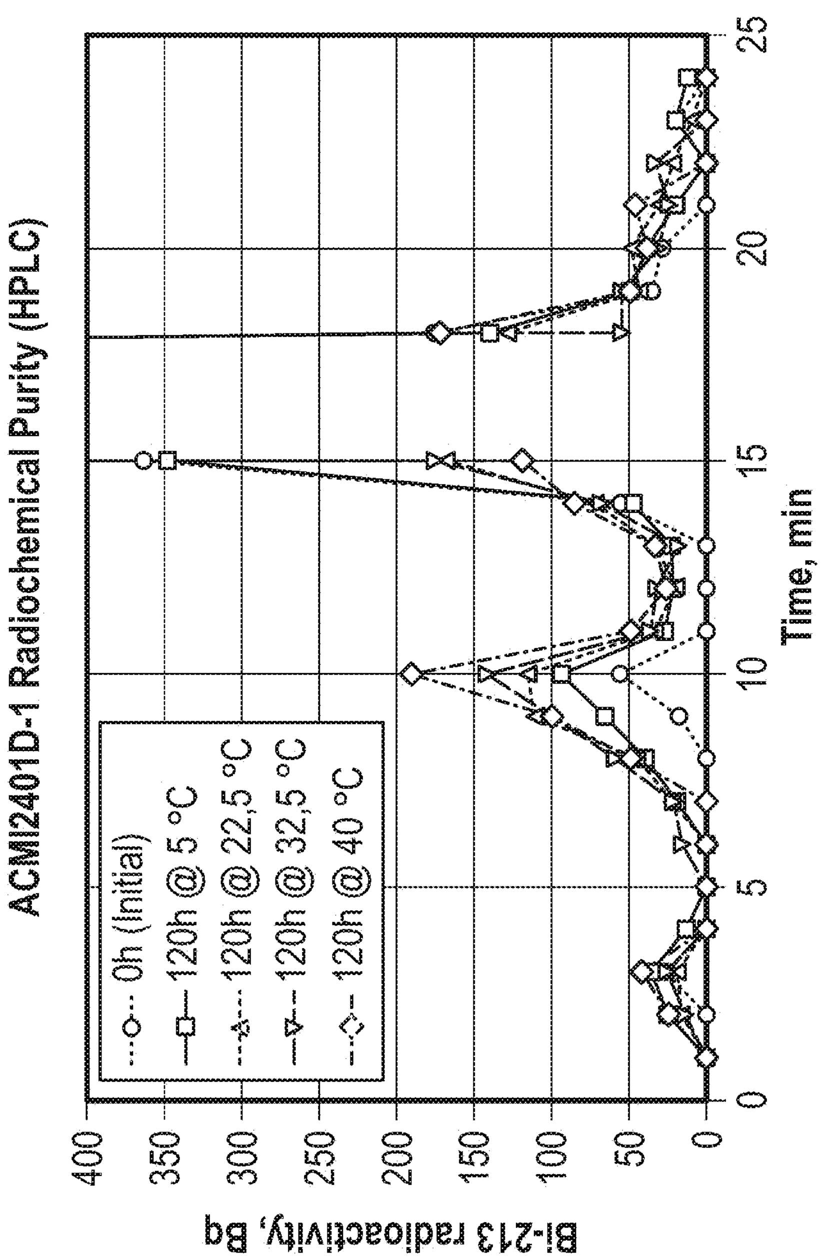
FIG. 30 depicts the radioactivity of HPLC fractions in the Process A formulation.
Figure 31:
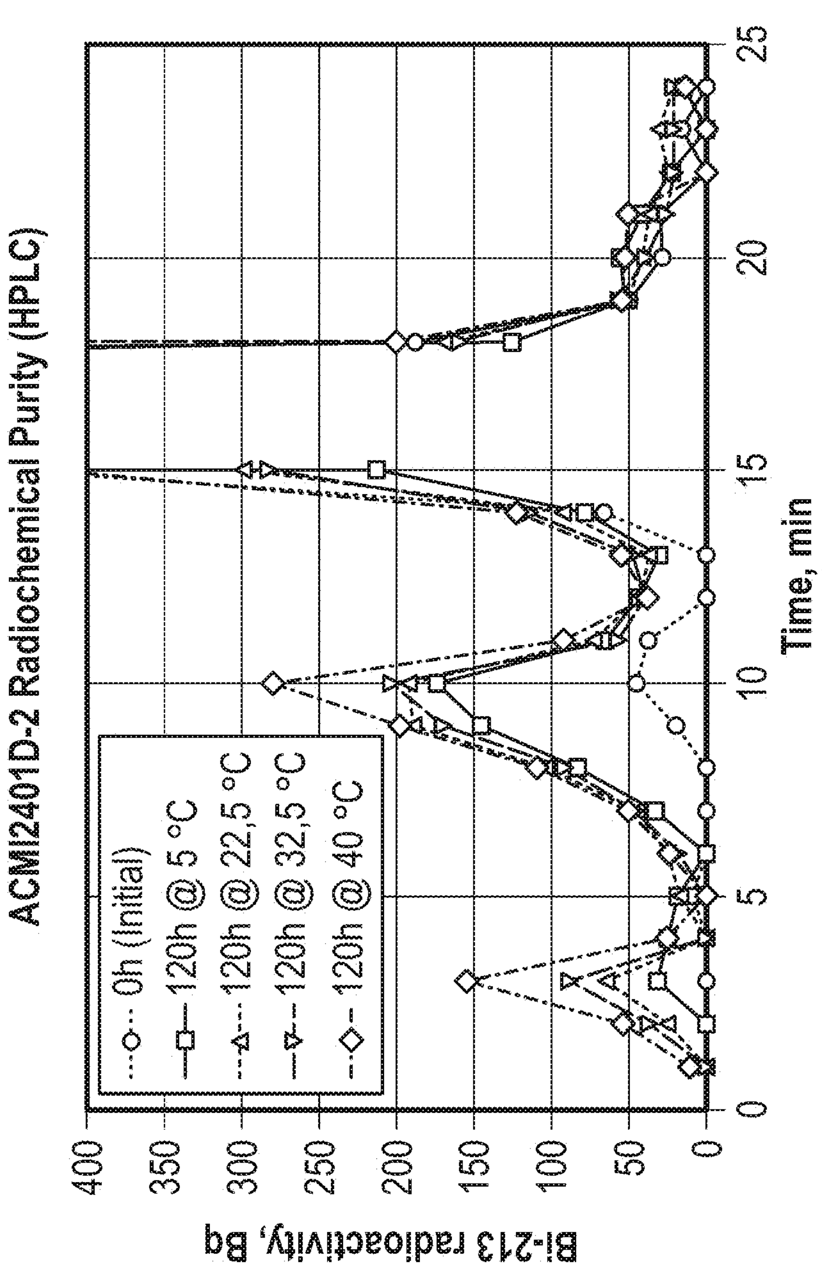
FIG. 31 depicts the radioactivity of HPLC fractions in the Process B formulation.

The results are provided in Tables 20-22 below. Radiochemical purity of $^{225}$Ac-PSMA I&T by the radio-TLC and HPLC methods for processes A and B are summarized in FIGS. 28 and 29. Radiochromatograms created based on the HPLC results from both processes are provided in FIGS. 30 and 31.

TABLE 20

Results of $^{225}$Ac-PSMA I&T injection manufacturing processes.

| Process | $^{225}Ac(NO_3)_3$•(mCi (MBq)) | Bulk volume (ml) | Radio-activity Concentration (MBq/ml) | Process Yield (%) | RCP. Initial (%) TLC | HPLC |
|---|---|---|---|---|---|---|
| A | 0.93 (34.41) | 63.6 | 0.501 | 92.6 | 99.81 | 99.50 |
| B | 0.93 (34.41) | 31.8 | 1.039 | 96.0 | 99.96 | 99.40 |

TABLE 21

Radiochemical purity of $^{225}$Ac-PSMA I&T injection prepared using process A stored at different temperatures.

| Temperature (° C.) | Method | RCP (%) 24 h | 48 h | 72 h | 96 h | 120 h |
|---|---|---|---|---|---|---|
| 5 | TLC | 99.69 | 99.52 | 99.59 | 99.66 | 99.60 |
| | HPLC | — | — | — | — | 98.07 |
| 22.5 | TLC | 99.77 | 99.64 | 99.52 | 99.49 | 99.67 |
| | HPLC | — | — | — | — | 97.86 |
| 32.5 | TLC | 99.93 | 99.63 | 99.44 | 99.51 | 99.57 |
| | HPLC | — | — | — | — | 97.67 |
| 40 | TLC | 100.00 | 99.59 | 99.48 | 99.48 | 99.63 |
| | HPLC | — | — | — | — | 97.58 |

TABLE 22

Radiochemical purity of $^{225}$Ac-PSMA I&T injection prepared using process B stored at different temperatures.

| Temperature (° C.) | Method | RCP (%) 24 h | 48 h | 72 h | 96 h | 120 h |
|---|---|---|---|---|---|---|
| 5 | TLC | 99.94 | 99.81 | 99.76 | 99.83 | 99.75 |
| | HPLC | — | — | — | — | 96.96 |
| 22.5 | TLC | 99.85 | 99.74 | 99.61 | 99.63 | 99.47 |
| | HPLC | — | — | — | — | 96.18 |
| 32.5 | TLC | 99.81 | 99.66 | 99.52 | 99.49 | 99.36 |
| | HPLC | — | — | — | — | 96.27 |
| 40 | TLC | 99.83 | 99.62 | 98.53 | 99.30 | 98.98 |
| | HPLC | — | — | — | — | 95.53 |

In both processes, the calculated yields were above 90%. In process A slightly more material remained in the $^{225}Ac(NO_3)_3$ vial and therefore the yield was slightly lower than in process B.

The initial radiochemical purity of $^{225}$Ac-PSMA I&T product was above 99% in both processes. However, the radiochemical stability was worse in process B, especially according to the HPLC results. This is thought to be due to the higher radioactivity concentration in the final formulation. It should be noted that process B allows the dilution of the product to radioactivity concentration of choice.

Manufacturing Process and Formulation Comparison

In order to compare the different options for manufacturing process and formulation, the differences between the options as well as the previous manufacturing process and formulation are summarized in Tables 23 and 24.

TABLE 23

Comparison of the $^{225}$Ac-PSMA I&T manufacturing processes.

| Process Parameter | Previous Process | Process A | Process B |
|---|---|---|---|
| Process Scale | 0.4 mCi | 1 mCi | 1 mCi |
| Radiolabeling Buffer | 0.02M sodium ascorbate | 56.5 mg/ml sodium ascorbate | 11.3 mg/ml sodium ascorbate |
| Radiolabeling Conditions | Set point 110° C. for 15 min | Set point 110° C. for 15 min | Set point 110° C. for 15 min |
| Purification | C18 Sep Pak | No purification | No purification |
| Process Yield | ≤70% | ≥90% | ≥90% |
| Radiochemical Purity (initial) | ≥95% | ≥99% | ≥99% |

TABLE 24

Comparison of the $^{225}$Ac-PSMA I&T formulations.

| Description | Previous Formulation | Process A Formulation | Process B Formulation |
|---|---|---|---|
| Dose Volume | NMT 10 ml | NMT 20 ml | NMT 10-20 ml |
| Radioactive Concentration | ~700 kBq/ml | ~500 kBq/ml | ~500 to ~1 000 kBq/ml |
| Total PSMA I&T Content | 120 μg/ Dose | NMT 0.1 mg/ Dose | NMT 0.1 mg/ Dose |
| Excipients | Ascorbic Acid 42.5 mg/ml Ethanol 7.5% (v/v) | Sodium Ascorbate 11.3 mg/ml | Sodium Ascorbate 11.3 mg/ml |
| Metal Scavenger | EDTA (Preservative in ASCOR L injection) | N/A | N/A |
| pH | 5.5-6 | 6 | 6 |
| Stability | 48 hours at RT | 120 hours at 5-40° C. | 120 hours at 5-40° C. |

As can be seen from the comparisons shown in Tables 23 and 24, both processes A and B, showed significant improvement in process yield and radiochemical purity compared to the previous process.

In the stability testing, $^{225}$Ac-PSMA I&T showed greater than 98% radiochemical purity by the radio-TLC method after 120-hour time point. Initial radiochemical purity by the HPLC fraction collection method was found comparable between the products manufactured using process A and B. In both cases the radiochemical purity was above 99%. However, at 120-hour time point the process A formulation showed greater radiochemical purity determined by the radio-TLC and HPLC fraction collection methods which is likely due to lower radioactivity concentration compared to the process B formulation. All samples from process A had radiochemical purity of 97.5% or greater at the time point, whereas the process B formulation showed only 95.5% radiochemical purity in the sample stored at 40° C. Radiochemical purity in other samples in process B were at or below 97.0% as well.

The effect of a higher activity concentration on the radiolysis of $^{255}$Ac-PSMA I&T in the process B formulation was not evident from the earlier formulation optimization screening. However, this was discovered by the HPLC-method that allowed for the determination of radiolysis fragments in the formulation. Thus, based on the results the 20 ml was decided as an optimal formulation which both processes could achieve.

In conclusion, around 1 mCi batch scale tested in both processes enable products for 3 to 4 patients to be produced in a single batch. From the two, process A is considered as the preferred option for the final process for validation. For future scaling up (potentially up to 2 mCi batch scale or more), process A has an advantage of a greater sodium ascorbate concentration in the reactor which may also provide additional protection from radiolysis during heating.

If deemed necessary, it is later possible to develop a process that is a combination of processes A and B. It would have the advantage of enabling acid neutralization prior to labeling and the process would therefore be less dependent on the amount and concentration of hydrochloric acid in the $^{225}Ac\ (NO_3)_3$ solution.

All references cited herein are hereby incorporated by reference. The foregoing is offered primarily for purposes of illustration. It will be readily apparent to those skilled in the art that further drugs can be included, and that the components, additives, proportions, methods of formulation, methods of use, and other parameters described herein can be modified further or substituted in various ways without departing from the spirit and scope of the invention.

IV. Statements

Statement 1: A radiopharmaceutical composition comprising: $^{225}$Actinium-PSMA I&T in an amount that provides a radioactivity concentration of about 250 kBq/mL to about 1100 kBq/mL; and sodium ascorbate in an amount of about of about 0.1 mg/mL to about 100 mg/mL; and, optionally hydrochloric acid; wherein the pharmaceutical composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100%; and wherein the pharmaceutical composition has a radiochemical stability of greater than 72-hours from production when stored at about 5° C. to about 40° C.

Statement 2: The radiopharmaceutical composition of statement 1, further comprising ethanol in an amount of about 1% to about 20% (v/v).

Statement 3: The radiopharmaceutical composition of statement 2, wherein the composition comprises ethanol in an amount of about 1% (v/v), about 2% (v/v), about 3% (v/v), about 3.5% (v/v), about 4% (v/v), about 4.5% (v/v), about 5% (v/v), about 5.5% (v/v), about 6% (v/v), about 6.5% (v/v), about 7% (v/v), about 7.5% (v/v), about 8% (v/v), about 8.5% (v/v), about 9% (v/v), about 9.5% (v/v), or about 10% (v/v).

Statement 4: The radiopharmaceutical composition of statement 2, wherein the amount of ethanol is about 7.5% (v/v).

Statement 5: The radiopharmaceutical composition of statement 1, wherein pH of the composition is from about 5.5 to about 7.5.

Statement 6: The radiopharmaceutical composition of statement 5, wherein the pH is 5.5 to 7.0.

Statement 7: The radiopharmaceutical composition of statement 5, wherein the pH is 6.0 to 7.0.

Statement 8: The radiopharmaceutical composition of statement 1, wherein the pharmaceutical composition has no metal scavengers.

Statement 9: The radiopharmaceutical composition of statement 1, wherein the sodium ascorbate is present at 22.5 mg/mL±15%.

Statement 10: The radiopharmaceutical composition of statement 1, wherein the sodium ascorbate is present at 11.3 mg/mL±15%.

Statement 11: The radiopharmaceutical composition of statement 1, wherein the sodium ascorbate is present at 5.0 mg/mL±15%.

Statement 12: The radiopharmaceutical composition of statement 1, wherein the pharmaceutical composition has a radiochemical stability of greater than 96-hours at about 5° C. to about 40° C.

Statement 13: The radiopharmaceutical composition of statement 1, wherein the pharmaceutical composition has a radiochemical stability of greater than 120-hours at about 5° C. to about 40° C.

Statement 14: The radiopharmaceutical composition of statement 1, wherein the pharmaceutical composition has a radiochemical stability of greater than 168-hours at about 5° C. to about 40° C.

Statement 15: The radiopharmaceutical composition of statement 1, wherein the radiochemical purity is greater than 91%.

Statement 16: The radiopharmaceutical composition of statement 1, wherein the radiochemical purity is greater than 92%.

Statement 17: The radiopharmaceutical composition of statement 1, wherein the radiochemical purity is greater than 93%.

Statement 18: The radiopharmaceutical composition of statement 1, wherein the radiochemical purity is greater than 94%.

Statement 19: The radiopharmaceutical composition of statement 1, wherein the radiochemical purity is greater than 95%.

Statement 20: The radiopharmaceutical composition of statement 1, wherein the radiochemical purity is greater than 96%.

Statement 21: The radiopharmaceutical composition of statement 1, wherein the radiochemical purity is greater than 97%.

Statement 22: The radiopharmaceutical composition of statement 1, wherein the radiochemical purity is greater than 98%

Statement 23: The radiopharmaceutical composition of statement 1, wherein the radiochemical purity is greater than 99%.

Statement 24: The radiopharmaceutical composition of statement 1, wherein the radiochemical purity is greater than 99.1%.

Statement 25: The radiopharmaceutical composition of statement 1, wherein the radiochemical purity is greater than 99.2%.

Statement 26: The radiopharmaceutical composition of statement 1, wherein the radiochemical purity is greater than 99.3%.

Statement 27: The radiopharmaceutical composition of statement 1, wherein the radiochemical purity is greater than 99.4%.

Statement 28: The radiopharmaceutical composition of statement 1, wherein the radiochemical purity is greater than 99.5%.

Statement 29: The radiopharmaceutical composition of statement 1, wherein the radiochemical purity is greater than 99.6%.

Statement 30: The radiopharmaceutical composition of statement 1, wherein the radiochemical purity is greater than 99.7%.

Statement 31: The radiopharmaceutical composition of statement 1, wherein the radiochemical purity is greater than 99.8%.

Statement 32: The radiopharmaceutical composition of statement 1, wherein the radiochemical purity is greater than 99.9%.

Statement 33: The radiopharmaceutical composition of statement 1, wherein the radioactivity concentration is about 400 kBq/mL to about 600 kBq/mL.

Statement 34: The radiopharmaceutical composition of statement 1, wherein the radioactivity concentration is about 450 kBq/mL to about 550 kBq/mL.

Statement 35: The radiopharmaceutical composition of statement 1, wherein the radioactivity concentration is about 500 kBq/mL to about 525 kBq/mL.

Statement 36: A radiopharmaceutical composition suitable for administration to a patient in need thereof, the composition comprising: $^{225}$Ac-PSMA I&T in an amount that provides a radioactivity concentration of about 250 kBq/mL to about 1100 kBq/mL; and sodium ascorbate in an amount of about of about 0.1 mg/mL to about 100 mg/mL; wherein the pharmaceutical composition has a radiochemical purity of between 90% to 100%; and wherein the pharmaceutical composition has a radiochemical stability of greater than 72-hours at about 5° C. to about 40° C.

Statement 37: A radiopharmaceutical comprising $^{225}$Ac-PSMA I&T in a single dose vial suitable for administration to a human patient in need thereof, wherein the composition is aliquoted from the composition of any of the previous statements.

Statement 38: A pharmaceutical composition comprising: $^{225}$Ac-PSMA I&T in an amount that provides a radioactivity concentration of about 0.3 MBq to about 1.4 MBq per mL of the pharmaceutical composition; ascorbic acid in an amount of about of about 20 mg to about 90 mg; and ethanol in an amount of about 40 mg to about 120 mg; wherein the pharmaceutical composition has a radiochemical purity greater than 96.5%; wherein the pharmaceutical composition has a radiochemical stability of greater than 48-hours; and wherein the pharmaceutical composition has no metal scavengers.

Statement 39: A radiopharmaceutical composition comprising $^{225}$Ac-PSMA I&T and sodium ascorbate at a pH of 5.5 to 7.5 in solution, wherein the composition is suitable for administration to a human patient in need thereof; wherein the composition has a radiochemical purity of between 90% to 100% at administration; and wherein the pharmaceutical composition has a radiochemical stability of greater than 72-hours at about 5° C. to about 40° C.

Statement 40: The radiopharmaceutical composition of statement 39, wherein dose volume of the composition is between about 10 to about 20 mL.

Statement: 41: A radiopharmaceutical composition comprising: $^{225}$Ac-PSMA I&T in an amount that provides a radioactivity concentration of about 500 kBq/mL to about 1000 kBq/mL; and sodium ascorbate in an amount of about 11.3 mg/mL; wherein the pH of the radiopharmaceutical composition is 6; wherein the radiopharmaceutical composition has a PSMA I&T content of no more than 0.1 mg per dose; wherein the radiopharmaceutical composition is administered at a dose volume of between 10 mL to 20 mL; wherein radiopharmaceutical composition has a radiochemical purity of between 90% to 100%; and wherein the radiopharmaceutical composition has a radiochemical stability of greater than 72-hours at about 5° C. to about 40° C.

Statement 42: A radiopharmaceutical precursor comprising: $^{225}$Ac-PSMA I&T in an amount that provides a radioactivity concentration of about 500 kBq/mL to about 800 kBq/mL; 1 mg/mL to 70 mg/mL of ascorbic acid; and ethanol; wherein radiochemical purity of the radiopharmaceutical precursor is greater than 90%.

Statement 43: A radiopharmaceutical precursor comprising: $^{225}$Ac-PSMA I&T in an amount that provides a radioactivity concentration of about 500 kBq/mL to about 800 kBq/mL; sodium chloride; 1 mg/mL to 70 mg/mL of sodium ascorbate; and ethanol; wherein radiochemical purity of the radiopharmaceutical precursor is greater than 90%.

Statement 44: A radiopharmaceutical precursor comprising: $^{225}$Ac-PSMA I&T in an amount that provides a radioactivity concentration of about 500 kBq/mL to about 800 kBq/mL; DTPA; 1 mg/mL to 70 mg/mL of sodium ascorbate; and ethanol; wherein radiochemical purity of the radiopharmaceutical precursor is greater than 90%.

Statement 45: A method of administering a radiopharmaceutical composition, the method comprising injecting the radiopharmaceutical composition into a patient in need thereof, the radiopharmaceutical composition comprising $^{225}$Ac-PSMA I&T and sodium acetate in a solution having a pH of 5.5 to 7.5, wherein the solution has a radiochemical purity of more than 90% when administered.

Statement 46: A method comprising radiolabeling $^{225}$Ac-PSMA I&T in a reaction mixture with a molar ratio of hydrochloric acid to sodium ascorbate of 1:0 to 1:500.

Statement 47: The method of statement 46, wherein the molar ratio of hydrochloric acid to sodium ascorbate is between 1:1 to 1:30.

Statement 48: The method of statement 46, wherein the molar ratio of hydrochloric acid to sodium ascorbate is between 1:1 to 1:10.

Statement 49: The method of statement 46, wherein the molar ratio of hydrochloric acid to sodium ascorbate is between 1:1 to 1:200.

Statement 50: A method comprising radiolabeling $^{225}$Ac-PSMA I&T in a reaction mixture with a molar ratio of hydrochloric acid to sodium ascorbate of 1:0 to 1:500 and labeling percent from between 1% to 99.99%.

Statement 51: A method comprising radiolabeling $^{225}$Ac-PSMA I&T in a reaction mixture without a buffering agent.

Statement 52: A method comprising radiolabeling $^{225}$Ac-PSMA I&T in a reaction mixture neutralized with a base at a temperature of ≥20° C., ≥25° C., ≥30° C., ≥35° C., ≥40° C., ≥45° C., ≥50° C., ≥55° C., ≥60° C., ≥65° C., ≥70° C., ≥75° C., ≥80° C., ≥85° C., ≥90° C., ≥95° C., ≥100° C., ≥105° C., ≥110° C., ≥115° C., or ≥120° C.

Statement 53: A method comprising radiolabeling $^{225}$Ac-PSMA I&T in a reaction mixture neutralized with NaOH at a temperature of ≥20° C., ≥25° C., ≥30° C., ≥35° C., ≥40° C., ≥45° C., ≥50° C., ≥55° C., ≥60° C., ≥65° C., ≥70° C., ≥75° C., ≥80° C., ≥85° C., ≥90° C., ≥95° C., ≥100° C., ≥105° C., ≥110° C., ≥115° C., or ≥120° C.

Statement 54: A method comprising radiolabeling $^{225}$Ac-PSMA I&T in a reaction mixture neutralized with NaOH at a temperature of ≥20° C., ≥25° C., ≥30° C., ≥35° C., ≥40° C., ≥45° C., ≥50° C., ≥55° C., ≥60° C., ≥65° C., ≥70° C., ≥75° C., ≥80° C., ≥85° C., ≥90° C., ≥95° C., ≥100° C., ≥105° C., ≥110° C., ≥115° C., or ≥120° C. for a period of 30 minutes or less.

Statement 55: A method comprising radiolabeling $^{225}$Ac-PSMA I&T in a reaction mixture neutralized with NaOH at a temperature of ≥20° C., ≥25° C., ≥30° C., ≥35° C., ≥40° C., ≥45° C., ≥50° C., ≥55° C., ≥60° C., ≥65° C., ≥70° C., ≥75° C., ≥80° C., ≥85° C., ≥90° C., ≥95° C., ≥100° C., ≥105° C., ≥110° C., ≥115° C., or ≥120° C. for a period of 15 minutes or less.

Statement 56: A method comprising radiolabeling $^{225}$Ac-PSMA I&T in a reaction mixture neutralized with NaOH at a temperature of ≥20° C., ≥25° C., ≥30° C., ≥35° C., ≥40° C., ≥45° C., ≥50° C., ≥55° C., ≥60° C., ≥65° C., ≥70° C., ≥75° C., ≥80° C., ≥85° C., ≥90° C., ≥95° C., ≥100° C., ≥105° C., ≥110° C., ≥115° C., or >120° C., wherein the resulting $^{225}$Ac-PSMA I&T composition radiolabels ≥95% in 3 minutes when radiolabeling is monitored by radio-TLC.

Statement 57: A method comprising radiolabeling $^{225}$Ac-PSMA I&T in a reaction mixture neutralized with NaOH at a temperature of ≥20° C., ≥25° C., ≥30° C., ≥35° C., ≥40° C., ≥45° C., ≥50° C., ≥55° C., ≥60° C., ≥65° C., ≥70° C., ≥75° C., ≥80° C., ≥85° C., ≥90° C., ≥95° C., ≥100° C., ≥105° C., ≥110° C., ≥115° C., or ≥120° C., wherein the resulting $^{225}$Ac-PSMA I&T composition radiolabels ≥95%, ≥96%, ≥97%, ≥98%, or ≥99% in 6 minutes when radiolabeling is monitored by radio-TLC.

Statement 58: A method comprising radiolabeling $^{225}$Ac-PSMA I&T in a reaction mixture neutralized with NaOH at a temperature of ≥20° C., ≥25° C., ≥30° C., ≥35° C., ≥40° C., ≥45° C., ≥50° C., ≥55° C., ≥60° C., ≥65° C., ≥70° C., ≥75° C., ≥80° C., ≥85° C., ≥90° C., ≥95° C., ≥100° C., ≥105° C., ≥110° C., ≥115° C., or ≥120° C., wherein the resulting $^{225}$Ac-PSMA I&T composition radiolabels ≥95%, ≥96%, ≥97%, ≥98%, or ≥99% in 9 minutes when radiolabeling is monitored by radio-TLC.

Statement 59: A radiopharmaceutical composition comprising: $^{225}$Ac-PSMA I&T in an amount that provides a radioactivity concentration of about 250 kBq/mL to about 1100 kBq/mL; and sodium ascorbate in an amount of about of about 0.1 mg/mL to about 100 mg/mL; and wherein the pharmaceutical composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at 72-hours after storage at a temperature of 5° C. to 40° C.

Statement 60: The radiopharmaceutical composition of statement 59, further comprising ethanol in an amount of about 1% to about 20% (v/v).

Statement 61: The radiopharmaceutical composition of statement 60, wherein the composition comprises ethanol in an amount of about 1% (v/v), about 2% (v/v), about 3% (v/v), about 3.5% (v/v), about 4% (v/v), about 4.5% (v/v), about 5% (v/v), about 5.5% (v/v), about 6% (v/v), about 6.5% (v/v), about 7% (v/v), about 7.5% (v/v), about 8% (v/v), about 8.5% (v/v), about 9% (v/v), about 9.5% (v/v), or about 10% (v/v).

Statement 62: The radiopharmaceutical composition of statement 60, wherein the amount of ethanol is about 7.5% (v/v).

Statement 63: The radiopharmaceutical composition of statement 59, wherein pH of the composition is from about 5.5 to about 7.5.

Statement 64: The radiopharmaceutical composition of statement 63, wherein the pH is 5.5 to 7.0.

Statement 65: The radiopharmaceutical composition of statement 64, wherein the pH is 6.0 to 7.0.

Statement 66: The radiopharmaceutical composition of statement 59, wherein the pharmaceutical composition has no metal scavengers.

Statement 67: The radiopharmaceutical composition of statement 59, wherein the sodium ascorbate is present at 22.5 mg/mL±15%.

Statement 68: The radiopharmaceutical composition of statement 59, wherein the sodium ascorbate is present at 11.3 mg/mL±15%.

Statement 69: The radiopharmaceutical composition of statement 59, wherein the sodium ascorbate is present at 5.0 mg/mL±15%.

Statement 70: The radiopharmaceutical composition of statement 59, wherein the pharmaceutical composition has a radiochemical stability of greater than 96-hours at about 5° C. to about 40° C.

Statement 71: The radiopharmaceutical composition of statement 59, wherein the pharmaceutical composition has a radiochemical stability of greater than 120-hours at about 5° C. to about 40° C.

Statement 72: The radiopharmaceutical composition of statement 59, wherein the pharmaceutical composition has a radiochemical stability of greater than 168-hours at about 5° C. to about 40° C.

Statement 73: A radiopharmaceutical composition comprising: $^{225}$Ac-PSMA I&T in an amount that provides a radioactivity concentration of about 250 kBq/mL to about 1100 kBq/mL; and sodium ascorbate in an amount of about of about 0.1 mg/mL to about 100 mg/mL; and wherein the pharmaceutical composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at 96-hours after storage at a temperature of 5° C. to 40° C.

Statement 74: A radiopharmaceutical composition comprising: $^{225}$Ac-PSMA I&T in an amount that provides a radioactivity concentration of about 250 kBq/mL to about 1100 kBq/mL; and sodium ascorbate in an amount of about of about 0.1 mg/mL to about 100 mg/mL; and wherein the pharmaceutical composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at 120-hours after storage at a temperature of 5° C. to 40° C.

Statement 75: The radiopharmaceutical composition according to any of the previous statements, wherein the composition is suitable for administration to a patient in need thereof.

Statement 76: The radiopharmaceutical composition according to any of the previous statements, wherein the radiochemical purity is greater than 91% at production and 72 hours later.

Statement 77: The radiopharmaceutical composition according to any of the previous statements, wherein the radiochemical purity is greater than 92% at production and 72 hours later.

Statement 78: The radiopharmaceutical composition according to any of the previous statements, wherein the radiochemical purity is greater than 93% at production and 72 hours later.

Statement 79: The radiopharmaceutical composition according to any of the previous statements, wherein the radiochemical purity is greater than 94% at production and 72 hours later.

Statement 80: The radiopharmaceutical composition according to any of the previous statements, wherein the radiochemical purity is greater than 95% at production and 72 hours later.

Statement 81: The radiopharmaceutical composition according to any of the previous statements, wherein the radiochemical purity is greater than 96% at production and 72 hours later.

Statement 82: The radiopharmaceutical composition according to any of the previous statements, wherein the radiochemical purity is greater than 97% at production and 72 hours later.

Statement 82: The radiopharmaceutical composition according to any of the previous statements, wherein the radiochemical purity is greater than 98% at production and 72 hours later.

Statement 84: The radiopharmaceutical composition according to any of the previous statements, wherein the radiochemical purity is greater than 99% at production and 72 hours later.

Statement 85: The radiopharmaceutical composition according to any of the previous statements, wherein the radiochemical purity is greater than 99.1% at production and 72 hours later.

Statement 86: The radiopharmaceutical composition according to any of the previous statements, wherein the radiochemical purity is greater than 99.2% at production and 72 hours later.

Statement 87: The radiopharmaceutical composition according to any of the previous statements, wherein the radiochemical purity is greater than 99.3% at production and 72 hours later.

Statement 88: The radiopharmaceutical composition according to any of the previous statements, wherein the radiochemical purity is greater than 99.4% at production and 72 hours later.

Statement 89: The radiopharmaceutical composition according to any of the previous statements, wherein the radiochemical purity is greater than 99.5% at production and 72 hours later.

Statement 90: The radiopharmaceutical composition according to any of the previous statements, wherein the radiochemical purity is greater than 99.6% at production and 72 hours later.

Statement 91: The radiopharmaceutical composition according to any of the previous statements, wherein the radiochemical purity is greater than 99.7% at production and 72 hours later.

Statement 92: The radiopharmaceutical composition according to any of the previous statements, wherein the radiochemical purity is greater than 99.8% at production and 72 hours later.

Statement 92: The radiopharmaceutical composition according to any of the previous statements, wherein the radiochemical purity is greater than 99.9% at production and 72 hours later.

Statement 94: The radiopharmaceutical composition according to any of the previous statements, wherein the radiochemical purity is greater than 91% at production and 120 hours later.

Statement 95: The radiopharmaceutical composition according to any of the previous statements, wherein the radiochemical purity is greater than 92% at production and 120 hours later.

Statement 96: The radiopharmaceutical composition according to any of the previous statements, wherein the radiochemical purity is greater than 93% at production and 120 hours later.

Statement 97: The radiopharmaceutical composition according to any of the previous statements, wherein the radiochemical purity is greater than 94% at production and 120 hours later.

Statement 98: The radiopharmaceutical composition according to any of the previous statements, wherein the radiochemical purity is greater than 95% at production and 120 hours later.

Statement 99: The radiopharmaceutical composition according to any of the previous statements, wherein the radiochemical purity is greater than 96% at production and 120 hours later.

Statement 100: The radiopharmaceutical composition according to any of the previous statements, wherein the radiochemical purity is greater than 97% at production and 120 hours later.

Statement 101: The radiopharmaceutical composition according to any of the previous statements, wherein the radiochemical purity is greater than 98% at production and 120 hours later.

Statement 102: The radiopharmaceutical composition according to any of the previous statements, wherein the radiochemical purity is greater than 99% at production and 120 hours later.

Statement 103: The radiopharmaceutical composition according to any of the previous statements, wherein the radiochemical purity is greater than 99.1% at production and 120 hours later.

Statement 104: The radiopharmaceutical composition according to any of the previous statements, wherein the radiochemical purity is greater than 99.2% at production and 120 hours later.

Statement 105: The radiopharmaceutical composition according to any of the previous statements, wherein the radiochemical purity is greater than 99.3% at production and 120 hours later.

Statement 106: The radiopharmaceutical composition according to any of the previous statements, wherein the radiochemical purity is greater than 99.4% at production and 120 hours later.

Statement 107: The radiopharmaceutical composition according to any of the previous statements, wherein the radiochemical purity is greater than 99.5% at production and 120 hours later.

Statement 108: The radiopharmaceutical composition according to any of the previous statements, wherein the radiochemical purity is greater than 99.6% at production and 120 hours later.

Statement 109: The radiopharmaceutical composition according to any of the previous statements, wherein the radiochemical purity is greater than 99.7% at production and 120 hours later.

Statement 110: The radiopharmaceutical composition according to any of the previous statements, wherein the radiochemical purity is greater than 99.8% at production and 120 hours later.

Statement 111: The radiopharmaceutical composition according to any of the previous statements, wherein the radiochemical purity is greater than 99.9% at production and 120 hours later.

Statement 112: A radiopharmaceutical comprising $^{225}$Ac-PSMA I&T in a single dose vial suitable for administration to a human patient in need thereof, wherein the composition is aliquoted from the composition of any of the previous statements.

Statement 113: A radiopharmaceutical composition comprising: $^{225}$Ac-PSMA I&T in an amount that provides a radioactivity concentration of about 250 kBq/mL to about 1100 kBq/mL; and sodium ascorbate in an amount of about of about 0.1 mg/mL to about 100 mg/mL; optionally hydrochloric acid; and wherein the pharmaceutical composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at 72-hours after storage, 96-hours after storage, or 120 hours after storage at a temperature of 5° C. to 40° C.

Statement 114: The radiopharmaceutical composition according to any of the previous statements, wherein there is a molar ratio of hydrochloric acid to sodium ascorbate of 1:0 to 1:500.

Statement 115: The radiopharmaceutical composition according to any of the previous statements, wherein the molar ratio of hydrochloric acid to sodium ascorbate is between 1:1 to 1:30.

Statement 116: The radiopharmaceutical composition according to any of the previous statements, wherein the molar ratio of hydrochloric acid to sodium ascorbate is between 1:1 to 1:10.

Statement 117: The radiopharmaceutical composition according to any of the previous statements, wherein the molar ratio of hydrochloric acid to sodium ascorbate is between 1:1 to 1:200.

Statement 118: The radiopharmaceutical composition according to any of the previous statements, wherein the composition is suitable for administration to a human patient in need thereof.

Statement 119: A composition comprising $^{225}$Ac-PSMA I&T with a radioactivity amount of 1 mCi±5%, 10%, or 15%.

Statement 120: The composition of statement 119, wherein the composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at production.

Statement 121: The composition of statement 119, wherein the composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at 72-hours after storage, 96-hours after storage, or 120 hours after storage at a temperature of 5° C. to 40° C.

Statement 122: The composition of statement 119, wherein the composition comprises about 0.9 mg/ml to about 100.0 mg/ml sodium ascorbate.

Statement 123: The composition of statement 119, wherein the composition comprises 11.3 mg/ml sodium ascorbate±5%, 10%, or 15%.

Statement 124: The composition of statement 119, wherein the composition comprises 56.5 mg/ml sodium ascorbate±5%, 10%, or 15%.

Statement 125: The composition of statement 119, wherein the composition has been heated to a temperature ≥75° C., ≥80° C., ≥85° C., ≥90° C., ≥95° C., ≥100° C., ≥105° C., ≥110° C., ≥115° C., or ≥120° C.

Statement 126: The composition of statement 119, wherein the composition has been heated to a temperature ≥75° C., ≥80° C., ≥85° C., ≥90° C., ≥95° C., ≥100° C., ≥105° C., ≥110° C., ≥115° C., or ≥120° C. for at least 15 minutes.

Statement 127: The composition of statement 119, wherein the composition has been heated to a temperature ≥75° C., ≥80° C., ≥85° C., ≥90° C., ≥95° C., ≥100° C., ≥105° C., ≥110° C., ≥115° C., or ≥120° C. for at least 15 minutes in the presence of a base.

Statement 128: The composition of statement 119, wherein the composition has been heated to a temperature ≥110° C. for at least 15 minutes in the presence of a base.

Statement 129: The composition of statement 119, wherein the composition has been heated to a temperature ≥110° C. for at least 15 minutes in the presence of NaOH.

Statement 130: The composition of statement 119, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C.

Statement 131: The composition of statement 119, wherein the composition has been radiolabelled at a temperature >75° C., ≥80° C., ≥85° C., ≥90° C., ≥95° C., ≥100° C., ≥105° C., ≥110° C., ≥115° C., or ≥120° C. for at least 5 minutes.

Statement 132: The composition of statement 119, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 9 minutes.

Statement 133: The composition of statement 119, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 15 minutes.

Statement 134: The composition of statement 119, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 5 minutes in the presence of a base.

Statement 135: The composition of statement 119, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 9 minutes in the presence of a base.

Statement 136: The composition of statement 119, wherein the composition has been radiolabelled at a temperature ≥110° C. for at least 5 minutes in the presence of a base.

Statement 137: The composition of statement 119, wherein the composition has been radiolabelled at a temperature ≥110° C. for at least 9 minutes in the presence of a base.

Statement 138: The composition of statement 119, wherein the composition has been radiolabelled at a temperature ≥110° C. for at least 15 minutes in the presence of a base.

Statement 139: The composition of statement 118, wherein the composition has been heated to a temperature ≥110° C. for at least 5 minutes, at least 9 minutes, or at least 15 minutes in the presence of NaOH.

Statement 140: A composition comprising $^{225}$Ac-PSMA I&T with an amount of no more than (NMT) 0.1 mg of PSMA I&T per dose.

Statement 141: The composition of statement 140, wherein the composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at production.

Statement 142: The composition of statement 140, wherein the composition has a radiochemical purity of about 90% to about 100%, about 90% to about 95%, about 95% to about 100%, about 98% to about 100%, about 98.5% to about 100%, about 99.0% to about 100%, about 99.5% to about 100%, about 99.6% to about 100%, about 99.7% to about 100%, about 99.8% to about 100%, or about 99.9% to about 100% at 72-hours after storage, 96-hours after storage, or 120 hours after storage at a temperature of 5° C. to 40° C.

Statement 143: The composition of statement 140, wherein the composition comprises about 0.9 mg/ml to about 100.0 mg/ml sodium ascorbate.

Statement 144: The composition of statement 140, wherein the composition comprises 11.3 mg/ml sodium ascorbate±5%, 10%, or 15%.

Statement 145: The composition of statement 140, wherein the composition comprises 56.5 mg/ml sodium ascorbate±5%, 10%, or 15%.

Statement 146: The composition of statement 140, wherein the composition has been heated to a temperature ≥75° C., ≥80° C., ≥85° C., ≥90° C., ≥95° C., ≥100° C., ≥105° C., ≥110° C., ≥115° C., or ≥120° C.

Statement 147: The composition of statement 140, wherein the composition has been heated to a temperature >75° C., ≥80° C., ≥85° C., ≥90° C., ≥95° C., ≥100° C., ≥105° C., ≥110° C., ≥115° C., or ≥120° C. for at least 15 minutes.

Statement 148: The composition of statement 140, wherein the composition has been heated to a temperature ≥75° C., ≥80° C., ≥85° C., ≥90° C., ≥95° C., ≥100° C., ≥105° C., ≥110° C., ≥115° C., or ≥120° C. for at least 15 minutes in the presence of a base.

Statement 149: The composition of statement 140, wherein the composition has been heated to a temperature ≥110° C. for at least 15 minutes in the presence of a base.

Statement 150: The composition of statement 140, wherein the composition has been heated to a temperature ≥110° C. for at least 15 minutes in the presence of NaOH.

Statement 151: The composition of statement 140, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C.

Statement 152: The composition of statement 140, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 5 minutes.

Statement 153: The composition of statement 140, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 9 minutes.

Statement 154: The composition of statement 140, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 15 minutes.

Statement 155: The composition of statement 140, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 5 minutes in the presence of a base.

Statement 156: The composition of statement 140, wherein the composition has been radiolabelled at a temperature ≥75° C., ≥80° C., ≥85° C., ≥90° C., ≥95° C., ≥100° C., ≥105° C., ≥110° C., ≥115° C., or ≥120° C. for at least 9 minutes in the presence of a base.

Statement 157: The composition of statement 140, wherein the composition has been radiolabelled at a temperature ≥110° C. for at least 5 minutes in the presence of a base.

Statement 158: The composition of statement 140, wherein the composition has been radiolabelled at a temperature ≥110° C. for at least 9 minutes in the presence of a base.

Statement 159: The composition of statement 140, wherein the composition has been radiolabelled at a temperature ≥110° C. for at least 15 minutes in the presence of a base.

Statement 160: The composition of statement 140, wherein the composition has been heated to a temperature ≥110° C. for at least 5 minutes, at least 9 minutes, or at least 15 minutes in the presence of NaOH.

Statement 161: The composition according to any of the previous statements, further comprising an acid.

Statement 162: The composition according to any of the previous statements, further comprising hydrochloric acid.

Statement 163: The composition according to any of the previous statements, further comprising ethanol.

Statement 164: The composition according to any of the previous statements, comprising 0.01 to 42.5 mg/ml sodium ascorbate or ascorbic acid.

Statement 165: The composition according to any of the previous statements, comprising 0.01 to 100.0 mg/ml sodium ascorbate or ascorbic acid.

Statement 166: The composition according to any of the previous statements, wherein the radioactivity concentration of the composition is between 250 kBq/mL to 500 kBq/mL.

Statement 167: The composition according to any of the previous statements, wherein the radioactivity concentration of the composition is between 500 kBq/mL to 800 kBq/mL.

Statement 168: The composition according to any of the previous statements, wherein the radioactivity concentration of the composition is between 500 kBq/mL to 1,000 kBq/mL.

Statement 169: The composition according to any of the previous statements, wherein the radioactivity concentration of the composition is between 500 kBq/mL to 1,100 kBq/mL.

Statement 170: The composition according to any of the previous statements, wherein the radioactivity concentration of the composition is between comprises 500 kBq/mL to 1,250 kBq/mL RAC (kBq/ml).

Statement 171: The composition according to any of the previous statements, wherein the radioactivity concentration of the composition is between comprises 500 kBq/mL to 1,500 kBq/mL RAC (kBq/ml).

Statement 172: The composition according to any of the previous statements, wherein the composition comprises an absence of DTPA.

Statement 173: The composition according to any of the previous statements, wherein the composition comprises an absence of metal scavengers other than PSMA I&T.

Statement 174: The composition according to any of the previous statements, wherein there is a molar ratio of hydrochloric acid to sodium ascorbate of 1:0 to 1:500.

Statement 175: The composition according to any of the previous statements, wherein the molar ratio of hydrochloric acid to sodium ascorbate is between 1:1 to 1:30

Statement 176: The composition according to any of the previous statements, wherein the molar ratio of hydrochloric acid to sodium ascorbate is between 1:1 to 1:10.

Statement 177: The composition according to any of the previous statements, wherein the molar ratio of hydrochloric acid to sodium ascorbate is between 1:1 to 1:200.

Statement 178: The composition according to any of the previous statements, wherein the pH is between 5.5 and 7.

Statement 179: The composition according to any of the previous statements, wherein there is an absence of buffering agent.

Statement 180: The radiopharmaceutical composition according to any of the previous statements, wherein the composition is suitable for administration to a human patient in need thereof.

Statement 181: A composition comprising $^{225}$Ac-PSMA I&T, wherein the molar ratio of the PSMA I&T to $^{225}$Ac is from ≥50:1.0, ≥100:1.0, ≥500:1.0, ≥1,000:1.0, ≥2,000:1.0, ≥3,000:1.0, or ≥4,000:1.0, and the composition is suitable for administration to a human patient in need thereof.

Statement 182: A composition comprising $^{225}$Ac-PSMA I&T, wherein the molar ratio of the PSMA I&T to $^{225}$Ac is from 1,000:1.0 to 5,000:1.0, 2,000:1.0 to 4,000:1.0, or 2,500:1.0 to 3,500:1.0, and the composition is suitable for administration to a human patient in need thereof.

Statement 183: A composition comprising $^{225}$Ac-PSMA I&T, wherein the molar ratio of the PSMA I&T to $^{225}$Ac is from 3,000:1.0 to 3,500:1.0, 3,050:1.0 to 3,450:1.0, 3,100:1.0 to 3,400:1.0, 3,150:1.0 to 3,350:1.0, or 3,200:1.0 to 3,300:1.0, and the composition is suitable for administration to a human patient in need thereof.

Statement 184: The composition according to any of the previous statements, wherein the composition has a total administered dose of about 10 ml to about 20 ml, about 10 ml to about 30 ml, about 10 ml to about 40 ml, or 10 ml to about 50 ml.

Statement 185: The composition according to any of the previous statements, wherein the composition has a total administered dose of about 20 ml to about 30 ml.

Statement 186: The composition according to any of the previous statements, wherein the composition has a total administered dose of about 25 ml to about 26 ml.

Statement 187: The composition according to any of the previous statements, wherein the composition has a radiochemical purity (RCP) of 95% or greater.

Statement 188: The composition according to any of the previous statements, wherein the composition has a radiochemical purity (RCP) of 95% or greater for at least 120 hours.

Statement 189: The composition according to any of the previous statements, wherein the composition has a radiochemical purity (RCP) of 95% or greater for at least 72 hours after formulation, at least 84 hours after formulation, at least 96 hours after formulation, or at least 108 hours after formulation when stored at about 5° C. to about 40° C.

Statement 190: The composition according to any of the previous statements, wherein the composition has a radiochemical purity (RCP) of 97.5% or greater for at least 72 hours after formulation, at least 84 hours after formulation, at least 96 hours after formulation, or at least 108 hours after formulation when stored at about 5° C. to about 40° C.

Statement 191: The composition according to any of the previous statements, wherein the composition has a radiochemical purity (RCP) of 98% or greater for at least 72 hours after formulation, at least 84 hours after formulation, at least 96 hours after formulation, or at least 108 hours after formulation when stored at about 5° C. to about 40° C.

Statement 192: The composition according to any of the previous statements, wherein the composition has a radiochemical purity (RCP) of 99% or greater for at least 72 hours after formulation, at least 84 hours after formulation, at least 96 hours after formulation, or at least 108 hours after formulation when stored at about 5° C. to about 40° C.

Statement 193: The composition according to any of the previous statements, wherein the molar ratio of the PSMA I&T to $^{225}$Ac is from 3,225:1.0±25%, 3,225:1.0±20%, 3,225:1.0±15%, 3,225:1.0±10%, or 3,225:1.0±5%.

Statement 194: The composition according to any of the previous statements, wherein the composition comprises 8.0±25% MBq of $^{225}$Ac-PSMA I&T, 8.0±20% MBq of $^{225}$Ac-PSMA I&T, 8.0±15% MBq of $^{225}$Ac-PSMA I&T, 8.0±10% MBq of $^{225}$Ac-PSMA I&T, or 8.0±5% MBq of $^{225}$Ac-PSMA I&T.

Statement 195: The composition according to any of the previous statements, wherein the composition comprises 0.395 MBq/ml±25% of $^{225}$Ac-PSMA I&T, 0.495 MBq/ml±25% of $^{225}$Ac-PSMA I&T, 0.595 MBq/ml±25% of $^{225}$Ac-PSMA I&T, 0.695 MBq/ml±25% of $^{225}$Ac-PSMA I&T, or 0.795 MBq/ml±25% of $^{225}$Ac-PSMA I&T.

Statement 196: The composition according to any of the previous statements, wherein the composition comprises 0.895 MBq/ml±25% of $^{225}$Ac-PSMA I&T, 0.995 MBq/mL±25% of $^{225}$Ac-PSMA I&T, 1.095 MBq/mL±25% of $^{225}$Ac-PSMA I&T, 1.195 MBq/mL±25% of $^{225}$Ac-PSMA I&T, 1.295 MBq/mL±25% of $^{225}$Ac-PSMA I&T, 1.395 MBq/mL±25% of $^{225}$Ac-PSMA I&T, or 1.495 MBq/mL±25% of $^{225}$Ac-PSMA I&T.

Statement 197: The composition according to any of the previous statements, wherein the composition comprises 0.216±25% mCi of $^{225}$Ac-PSMA I&T, 0.216±20% mCi of $^{225}$Ac-PSMA I&T, 0.216±15% mCi of $^{225}$Ac-PSMA I&T, 0.216±10% mCi of $^{225}$Ac-PSMA I&T, or 0.216±5% mCi of $^{225}$Ac-PSMA I&T.

Statement 198: The composition according to any of the previous statements, wherein the composition has a relative biological effectiveness (RBE) of ≥4.0, ≥4.1, ≥4.2, ≥4.3, ≥4.4, ≥4.5, ≥4.6, ≥4.7, ≥4.8, ≥4.9, ≥5.0, ≥5.1, ≥5.2, ≥5.3, ≥5.4, ≥5.5, ≥5.6, ≥5.7, ≥5.8, ≥5.9, or ≥6.0 for $^{225}$Ac compared to $^{177}$Lu.

Statement 199: The composition according to any of the previous statements, wherein the PSMA I&T content is 95 μg/dose #15%, ±10%, or ±5%, 90 μg/dose ±15%, ±10%, or ±5%, 85 μg/dose±15%, ±10%, or ±5%, 80 μg/dose±15%, ±10%, or ±5%, 75 μg/dose±15%, ±10%, or ±5%, 70 μg/dose±15%, ±10%, or ±5%, 60 μg/dose±15%, ±10%, or ±5%, 55 μg/dose±15%, ±10%, or ±5%, 50 μg/dose±15%, ±10%, or ±5%, 45 μg/dose±15%, ±10%, or ±5%, or 40 μg/dose±15%, ±10%.

Statement 200: The composition according to any of the previous statements, wherein the total PSMA I&T and M-PSMA I&T content is 95 μg/dose±15%, ±10%, or ±5%, 90 μg/dose±15%, ±10%, or ±5%, 85 μg/dose±15%, ±10%, or ±5%, 80 μg/dose±15%, ±10%, or ±5%, 75 μg/dose±15%, ±10%, or ±5%, 70 μg/dose±15%, ±10%, or ±5%, 60 μg/dose±15%, ±10%, or ±5%, 55 μg/dose±15%, ±10%, or ±5%, 50 μg/dose±15%, ±10%, or ±5%, 45 μg/dose±15%, ±10%, or ±5%, or 40 μg/dose±15%, ±10%.

Statement 201: The composition according to any of the previous statements, wherein the composition comprises about 2 μg/mL to about 12 μg/mL PSMA I&T, about 4 μg/mL to about 12 μg/mL PSMA I&T, about 6 μg/mL to about 12 μg/mL PSMA I&T, about 4 μg/mL to about 6 μg/mL PSMA I&T, about 8 μg/mL PSMA I&T to about 12 μg/mL PSMA I&T, or about 10 μg/mL to about 12 μg/mL PSMA I&T.

Statement 202: The composition according to any of the previous statements, wherein the pH of the composition is from 3.5 to 8.0, 3.5 to 7.5, 3.5 to 7.0, 3.5 to 6.0, 3.5 to 5.5, 3.5 to 5.0, or 3.5 to 4.5.

Statement 203: The composition according to any of the previous statements, wherein the pH of the composition is from 5.0 to 8.0, 5.0 to 7.5, 5.0 to 7.0, 5.0 to 6.0, or 5.0 to 5.5.

Statement 204: The composition according to any of the previous statements, wherein Fe metal content is ≤0.05 μg/GBq, ≤0.03 μg/GBq, ≤0.01 μg/GBq, or below the detectable limit.

Statement 205: The composition according to any of the previous statements, wherein Cu metal content is ≤0.05 μg/GBq, ≤0.03 μg/GBq, ≤0.01 μg/GBq, or below the detectable limit.

Statement 206: The composition according to any of the previous statements, wherein Zn metal content is ≤0.05 μg/GBq, ≤0.03 μg/GBq, ≤0.01 μg/GBq, or below the detectable limit.

Statement 207: The composition according to any of the previous statements, wherein Pb metal content is ≤0.05 μg/GBq, ≤0.03 μg/GBq, ≤0.01 μg/GBq, or below the detectable limit.

Statement 208: The composition according to any of the previous statements, wherein the composition is suitable for human administration for 1 or more cycles of treatment, 3 or more cycles of treatment, 6 or more cycles of treatment, 9 or more cycles of treatment, or 12 or more cycles of treatment.

Statement 209: The composition according to any of the previous statements, wherein the composition is suitable for human administration for 1 to about 6 cycles of treatment.

Statement 210: The composition according to any of the previous statements, wherein the composition is suitable for human administration for 5 or more cycles of treatment, 10 or more cycles of treatment, 15 or more cycles of treatment, 20 or more cycles of treatment, 25 or more cycles of treatment, or 30 or more cycles of treatment, or 35 or more cycles of treatment, or 40 or more cycles of treatment.

Statement 211: The composition according to any of the previous statements, wherein the composition is suitable for human administration for 7 or more cycles of treatment, 14 or more cycles of treatment, 21 or more cycles of treatment, 28 or more cycles of treatment, or 35 or more cycles of treatment.

Statement 212: The composition according to any of the previous statements, wherein the solution comprises about 0 mg/ml to about 100 mg/ml ascorbic acid, about 5 mg/ml to about 100 mg/ml ascorbic acid, about 5 mg/ml to about 90 mg/ml ascorbic acid, about 5 mg/ml to about 80 mg/ml ascorbic acid, about 5 mg/ml to about 70 mg/ml ascorbic acid, about 5 mg/ml to about 60 mg/ml ascorbic acid, about 5 mg/ml to about 50 mg/ml ascorbic acid, about 5 mg/ml to about 40 mg/ml ascorbic acid, about 5 mg/ml to about 30 mg/ml ascorbic acid, about 5 mg/ml to about 20 mg/ml ascorbic acid, about 5 mg/ml to about 10 mg/ml ascorbic acid, about 10 mg/ml to about 100 mg/ml ascorbic acid, about 10 mg/ml to about 90 mg/ml ascorbic acid, about 10 mg/ml to about 80 mg/ml ascorbic acid, about 10 mg/ml to about 70 mg/ml ascorbic acid, about 10 mg/ml to about 60 mg/ml ascorbic acid, about 10 mg/ml to about 50 mg/ml ascorbic acid, about 10 mg/ml to about 40 mg/ml ascorbic acid, about 10 mg/ml to about 30 mg/ml ascorbic acid, about 10 mg/ml to about 20 mg/ml ascorbic acid, about 15 mg/ml to about 100 mg/ml ascorbic acid, about 15 mg/ml to about 90 mg/ml ascorbic acid, about 15 mg/ml to about 80 mg/ml ascorbic acid, about 15 mg/ml to about 70 mg/ml ascorbic acid, about 15 mg/ml to about 60 mg/ml ascorbic acid, about 15 mg/ml to about 50 mg/ml ascorbic acid, about 15 mg/ml to about 45 mg/ml ascorbic acid, about 15 mg/ml to about 40 mg/ml ascorbic acid, about 15 mg/ml to about 30 mg/ml ascorbic acid, about 15 mg/ml to about 20 mg/ml ascorbic acid, about 20 mg/ml to about 100 mg/ml ascorbic acid, about 20 mg/ml to about 90 mg/ml ascorbic acid, about 20 mg/ml to about 80 mg/ml ascorbic acid, about 20 mg/ml to about 70 mg/ml ascorbic acid, about 20 mg/ml to about 60 mg/ml ascorbic acid, about 20 mg/ml to about 50 mg/ml ascorbic acid, about 20 mg/ml to about 40 mg/ml ascorbic acid, about 20 mg/ml to about 30 mg/ml ascorbic acid, about 20 mg/ml to about 25 mg/ml ascorbic acid, about 25 mg/ml to about 100 mg/ml ascorbic acid, about 25 mg/ml to about 90 mg/ml ascorbic acid, about 25 mg/ml to about 80 mg/ml ascorbic acid, about 25 mg/ml to about 70 mg/ml ascorbic acid, about 25 mg/ml to about 60 mg/ml ascorbic acid, about 25 mg/ml to about 50 mg/ml ascorbic acid, about 25 mg/ml to about 40 mg/ml ascorbic acid, about 25 mg/ml to about 30 mg/ml ascorbic acid, about 25 mg/ml to about 70 mg/ml ascorbic acid, about 30 mg/ml to about 100 mg/ml ascorbic acid, about 30 mg/ml to about 90 mg/ml ascorbic acid, about 30 mg/ml to about 80 mg/ml ascorbic acid, about 30 mg/ml to about 70 mg/ml ascorbic acid, about 30 mg/ml to about 60 mg/ml ascorbic acid, or about 30 mg/ml to about 50 mg/ml ascorbic acid.

Statement 213: The composition according to any of the previous statements, wherein the solution comprises about 5 mg/ml to about 10 mg/ml ascorbic acid, about 5 mg/ml to about 15 mg/ml ascorbic acid, about 5 mg/ml to about 20 mg/ml ascorbic acid, or about 5 mg/ml to about 25 mg/ml ascorbic acid.

Statement 214: The composition according to any of the previous statements, wherein the solution comprises at least 5 mg/ml ascorbic acid, at least 10 mg/ml ascorbic acid, at least 15 mg/ml ascorbic acid, at least 20 mg/ml ascorbic acid, at least 25 mg/ml ascorbic acid, at least 30 mg/ml ascorbic acid, at least 35 mg/ml ascorbic acid, at least 40 mg/ml ascorbic acid.

Statement 215: The composition according to any of the previous statements, wherein the solution comprises about 5 mg/ml to about 100 mg/ml ethanol, about 10 mg/ml to about 100 mg/ml ethanol, about 15 mg/ml to about 100 mg/ml ethanol, about 20 mg/ml to about 100 mg/ml ethanol, about 25 mg/ml to about 100 mg/ml ethanol, about 30 mg/ml to about 100 mg/ml ethanol, about 35 mg/ml to about 100 mg/ml ethanol, about 40 mg/ml to about 100 mg/ml ethanol, about 45 mg/ml to about 100 mg/ml ethanol, about 50 mg/ml to about 100 mg/ml ethanol, about 55 mg/ml to about 100 mg/ml ethanol, about 60 mg/ml to about 100 mg/ml ethanol, about 65 mg/ml to about 100 mg/ml ethanol, or about 70 mg/ml to about 100 mg/ml ethanol.

Statement 216: The composition according to any of the previous statements, wherein the solution comprises at least 5 mg/ml ethanol, at least 10 mg/ml ethanol, at least 15 mg/ml ethanol, at least 20 mg/ml ethanol, at least 25 mg/ml ethanol, at least 30 mg/ml ethanol, at least 35 mg/ml ethanol, at least 40 mg/ml ethanol, at least 45 mg/ml ethanol, at least 50 mg/ml ethanol, at least 55 mg/ml ethanol, at least 60 mg/ml ethanol, at least 65 mg/ml ethanol, or at least 70 mg/ml ethanol.

Statement 217: The composition according to any of the previous statements, wherein the composition further comprises EDTA or disodium EDTA.

Statement 218: The composition according to any of the previous statements, wherein the solution comprises about 5 mg/ml to about 70 mg/ml EDTA, about 10 mg/ml to about 70 mg/ml EDTA, about 15 mg/ml to about 70 mg/ml EDTA, or about 20 mg/ml to about 70 mg/ml EDTA.

Statement 219: The composition according to any of the previous statements, wherein the solution comprises at least 5 mg/ml EDTA, at least 10 mg/ml EDTA, at least 15 mg/ml EDTA, or at least 20 mg/ml EDTA.

Statement 220: The composition according to any of the previous statements, wherein the composition further comprises DTPA.

Statement 221: The composition according to any of the previous statements, wherein the composition comprises a specific activity of 0.112 MBq/nmol=0.025 MBq/nmol. 0.112 MBq/nmol±0.020 MBq/nmol, 0.112 MBq/nmol=0.015 MBq/nmol, 0.112 MBq/nmol #0.010 MBq/nmol, or 0.112 MBq/nmol±0.005 MBq/nmol.

Statement 222: The composition according to any of the previous statements, further comprising $^{221}$Fr and $^{213}$Bi.

Statement 223: A radiopharmaceutical kit comprising the composition according to any of the previous statements.

Statement 224: A radiopharmaceutical kit, comprising a vial comprising a composition according to any of the previous statements, and wherein $^{225}$Ac-PSMA I&T treatment with 1, 2, 3, 4, 5, 6, or 7 cycles at a dose is possible without the risk of kidney toxicities and/or wherein $^{225}$Ac-PSMA I&T treatment with 1, 2, 3, 4, 5, 6, or 7 cycles provides a mean projected dose that is below a cumulative absorbed dose to the kidney of 7 Gy, below 6.9 Gy, below 6.8 Gy, below 6.7 Gy, below 6.6 Gy, below 6.5 Gy, below 6.4 Gy, below 6.3 Gy, below 6.2 Gy, below 6.2 Gy, below 6.1 Gy, below 6 Gy, below 5.9 Gy, below 5.8 Gy, below 5.7 Gy, below 5.6 Gy, below 5.5 Gy, below 5.4 Gy, below 5.3 Gy, below 5.2 Gy, below 5.2 Gy, below 5.1 Gy, below 5 Gy, below 4.9 Gy, below 4.8 Gy, below 4.7 Gy, below 4.6 Gy, or below 4.5 Gy and/or the projected or actual cumulative absorbed dose to the kidneys at 1, 2, 3, 4, 5, 6, or 7 cycles is less than 7 Gy, 6.9 Gy, 6.8 Gy, 6.7 Gy, 6.6 Gy, 6.5 Gy, 6.4 Gy, 6.3 Gy, 6.2 Gy, 6.2 Gy, 6.1 Gy, 6 Gy, 5.9 Gy, 5.8 Gy, 5.7 Gy, 5.6 Gy, 5.5 Gy, 5.4 Gy, 5.3 Gy, 5.2 Gy, 5.2 Gy, 5.1 Gy, 5 Gy, 4.9 Gy, 4.8 Gy, 4.7 Gy, 4.6 Gy, or 4.5 Gy and no renal toxicities are observed.

Statement 225: A method comprising administering to a human patient in need thereof a composition radiopharmaceutical composition according to any of the previous statements.

Statement 226: A method comprising administering to a human patient in need thereof a composition radiopharmaceutical composition according to any of the previous statements, wherein administration of $^{225}$Ac-PSMA I&T treatment with 1, 2, 3, 4, 5, 6, or 7 cycles at a dose is possible without the risk of kidney toxicities and/or wherein $^{225}$Ac-PSMA I&T treatment with 1, 2, 3, 4, 5, 6, or 7 cycles provides a mean projected dose that is below a cumulative absorbed dose to the kidney of 7 Gy, below 6.9 Gy, below 6.8 Gy, below 6.7 Gy, below 6.6 Gy, below 6.5 Gy, below 6.4 Gy, below 6.3 Gy, below 6.2 Gy, below 6.2 Gy, below 6.1 Gy, below 6 Gy, below 5.9 Gy, below 5.8 Gy, below 5.7 Gy, below 5.6 Gy, below 5.5 Gy, below 5.4 Gy, below 5.3 Gy, below 5.2 Gy, below 5.2 Gy, below 5.1 Gy, below 5 Gy, below 4.9 Gy, below 4.8 Gy, below 4.7 Gy, below 4.6 Gy, or below 4.5 Gy and/or the projected or actual cumulative absorbed dose to the kidneys at 1, 2, 3, 4, 5, 6, or 7 cycles is less than 7 Gy, 6.9 Gy, 6.8 Gy, 6.7 Gy, 6.6 Gy, 6.5 Gy, 6.4 Gy, 6.3 Gy, 6.2 Gy, 6.2 Gy, 6.1 Gy, 6 Gy, 5.9 Gy, 5.8 Gy, 5.7 Gy, 5.6 Gy, 5.5 Gy, 5.4 Gy, 5.3 Gy, 5.2 Gy, 5.2 Gy, 5.1 Gy, 5 Gy, 4.9 Gy, 4.8 Gy, 4.7 Gy, 4.6 Gy, or 4.5 Gy and no renal toxicities are observed.

Statement 227: A method comprising administering to a human patient in need thereof a radiopharmaceutical composition according to any of the previous statements, wherein the absorbed radiation dose is determined via SPECT imaging, planar imaging, or a combination thereof.

Statement 228: A method comprising administering to a human patient in need thereof a radiopharmaceutical composition according to any of the previous statements, wherein the radiopharmaceutical composition has a radiochemical purity of about 90% to about 100%, at 120-hours after storage at a temperature of 5° C. to 40° C.

Statement 229: The composition according to any of the previous statements, wherein sodium ascorbate is present at 5.7 mg/ml±15%.

Statement 230: The composition according to any of the previous statements, wherein sodium ascorbate is present at 17 mg/ml±15%.

What is claimed is:

1. A method comprising:

administering a radiopharmaceutical composition to a patient in need thereof, wherein the composition comprises:

$^{225}$Ac-PSMA I&T in an amount that provides a radioactivity concentration of 250 kBq/mL to 1100 kBq/mL; and sodium ascorbate in an amount of 0.1 mg/mL to 100 mg/mL;

wherein the composition has a radiochemical purity of 90% to 100% when administered; and wherein the composition has a radiochemical purity of ≥90% at least 72 hours from production when stored at about 5° C. to about 40° C.

2. The method of claim 1, wherein the composition comprises $^{225}$Ac-PSMA I&T in an amount that provides a radioactivity concentration of 500 kBq/mL to 1000 kBq/mL.

3. The method of claim 1, wherein the composition comprises $^{225}$Ac-PSMA I&T in an amount that provides a radioactivity concentration of 250 kBq/mL to 500 kBq/mL.

4. The method of claim 1, wherein the composition comprises $^{225}$Ac-PSMA I&T in an amount that provides a radioactivity concentration of 500 kBq/mL to 800 kBq/mL.

5. The method of claim 1, wherein the composition has a radiochemical purity of about 90% to about 100% at 96 hours after storage at a temperature of 5° C. to 40° C.

6. The method of claim 1, wherein the composition has a radiochemical purity of about 90% to about 100% at 120 hours after storage at a temperature of 5° C. to 40° C.

7. The method of claim 1, wherein the composition further comprises hydrochloric acid and wherein the molar ratio of hydrochloric acid to sodium ascorbate is from 1:0 to 1:500.

8. The method of claim 1, wherein the composition has a pH from about 5.5 to about 7.5.

9. The method of claim 1, wherein the composition further comprises ethanol in an amount of about 1% to about 20% (v/v).

10. The method of claim 1, wherein the composition further comprises EDTA or disodium EDTA.

11. The method of claim 1, wherein the composition further comprises DTPA.

12. The method of claim 1, wherein the composition is administered to the patient for 1 or more cycles of treatment.

13. The method of claim 1, wherein the composition is administered to the patient for 3 or more cycles of treatment.

14. The method of claim 1, wherein the composition is administered to the patient for 9 or more cycles of treatment.

15. The method of claim 1, wherein the composition is administered to the patient for 12 or more cycles of treatment.

16. The method of claim 1, wherein the composition has a total administered volume between 10 mL to 50 mL.

17. The method of claim 1, wherein the composition has a total administered volume between 20 mL to 100 mL.

18. The method of claim 1, wherein the composition comprises about 2 μg/mL to about 12 μg/mL PSMA I&T.

19. The method of claim 1, wherein the composition comprises a specific activity of 0.112 MBq/nmol±0.025 MBq/nmol, 0.112 MBq/nmol±0.020 MBq/nmol, 0.112 MBq/nmol±0.015 MBq/nmol, 0.112 MBq/nmol±0.010 MBq/nmol, or 0.112 MBq/nmol±0.005 MBq/nmol.

20. The method of claim 1, wherein the composition comprises no more than (NMT) 0.1 mg of PSMA I&T per administered dose.

21. A method comprising:

administering a radiopharmaceutical composition to a patient in need thereof, wherein the composition comprises $^{225}$Ac-PSMA I&T in an amount that provides a radioactivity concentration of 250 kBq/mL to 1100 kBq/mL, wherein the composition has a radiochemical purity of 95% to 100% when administered, and wherein the composition has a radiochemical purity of ≥95% at least 72 hours from production when stored at about 5° C. to about 40° C.

22. The method of claim 21, wherein the composition has a radiochemical purity of ≥95% at least 96 hours from production when stored at about 5° C. to about 40° C.

23. The method of claim 21, wherein the composition has a radiochemical purity of ≥95% at least 120 hours from production when stored at about 5° C. to about 40° C.

24. A method of administering a radiopharmaceutical composition, the method comprising injecting the composition into a patient in need thereof, the composition comprising $^{225}$Ac-PSMA I&T and sodium ascorbate in a solution having a pH of 5.5 to 7.5, wherein the solution has a radiochemical purity of more than 90% when administered.

* * * * *